United States Patent
Xue et al.

(10) Patent No.: US 10,987,422 B2
(45) Date of Patent: Apr. 27, 2021

(54) FUNGAL VACCINE COMPOSITIONS AND METHODS OF USE THEREOF

(71) Applicant: Rutgers, The State University of New Jersey, New Brunswick, NJ (US)

(72) Inventors: Chaoyang Xue, Newark, NJ (US); Amariliz Rivera, Newark, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/317,186

(22) PCT Filed: Jul. 11, 2017

(86) PCT No.: PCT/US2017/041506
§ 371 (c)(1),
(2) Date: Jan. 11, 2019

(87) PCT Pub. No.: WO2018/013548
PCT Pub. Date: Jan. 18, 2018

(65) Prior Publication Data
US 2019/0290760 A1    Sep. 26, 2019

Related U.S. Application Data

(60) Provisional application No. 62/360,588, filed on Jul. 11, 2016.

(51) Int. Cl.
| | | |
|---|---|---|
| A61K 39/00 | (2006.01) | |
| A61K 39/395 | (2006.01) | |
| A61P 37/00 | (2006.01) | |
| A61P 31/10 | (2006.01) | |
| A61K 39/39 | (2006.01) | |
| C07K 14/37 | (2006.01) | |

(52) U.S. Cl.
CPC .... *A61K 39/39575* (2013.01); *A61K 39/0002* (2013.01); *A61K 39/39* (2013.01); *A61P 31/10* (2018.01); *A61P 37/00* (2018.01); *C07K 14/37* (2013.01); *A61K 2039/52* (2013.01); *A61K 2039/521* (2013.01); *A61K 2039/522* (2013.01); *A61K 2039/58* (2013.01)

(58) Field of Classification Search
None
See application file for complete search history.

(56) References Cited

U.S. PATENT DOCUMENTS

2007/0172503 A1    7/2007   Selitrennikoff et al.
2015/0328295 A1*   11/2015  Lodge .................. A61K 9/0073
                                                          424/274.1

OTHER PUBLICATIONS

Liu et al. 2011 (The F-Box protein Fpb-1 regulates Sexual Reproduction and Virulence in Cryptococcus neoformans; Eukaryotic Cell 10(6):791-802) (Year: 2011).*
Serrato et al. 2009 (cpFPaseI I, a novel redox-independent chloroplastic isoform of fructose-1,6-bisphosphatase; Plant, Cell and Environment (2009) 32, 811-827) (Year: 2009).*
Liu et al. 2011 (The F-Box protein Fbp-1 regulates sexual reproduction and virulence in Cryptococcus neoformans; Eukaryotic Cell 10(6): 791-802). (Year: 2011).*
Kozel et al. 1974 (Induction of Humoral Antibody Response by Soluble Polysaccharide of Cryptococcus neoformans; Mycopathologia et Mycologia applicata 54(1):21-30). (Year: 1974).*
Fromtling et al. 1979 (Immunization of mice with an avirulent pseudohypha) form of Cryptococcus neoformans; Mycopathologia; Sep. 28;68(3):179-81) (Year: 1979).*
Buchanan et al. 1998 (What makes Cryptococcus neoformans a Pathogen? Emerging Infectious Diseases; 4(1): 71-83). (Year: 1998).*
Liu et al., "The F-Box Protein Fbp1 Regulates Sexual Reproduction and Virulence in Cryptococcus neoformans," Eukaryotic Cell (Jun. 2011); 10(6):791-802.
Upadhya et al: "Induction of Protective Immunity to Cryptococcal Infection in Mice by a Heat-Killed, Chitosan-Deficient Strain of Cryptococcus Neoformans", MBIO, vol. 7, No. 3, May 10, 2016, pp. e00547-16, XP055664538, DOI: 10.1128/mBio.00547-16.
Rella, et al: "Role of Sterylglucosidase 1 (Sgl1) on the Pathogenicity of Cryptococcus Neoformans: Potential Applications for Vaccine Development", Frontiers in Microbiology, vol. 6, Aug. 11, 2015, p. 836, XP055664541, DOI: 10.3389/fmicb.2015.00836.
Medici, et al: "New Insights on the Development of Fungal Vaccines: From Immunity to Recent Challenges", Memorias Do Instituto Oswaldo Cruz, vol. 110, No. 8, Nov. 24, 2015, pp. 966-973, XP055664588, BR ISSN: 0074-0276, DOI: 10.1590/0074-02760150335.
Leopold Wager et al: "Is Development of a Vaccine Against Cryptococcus Neoformans Feasible?", PLOS Pathogens, vol. 11, No. 6, Jun. 18, 2015, p. e1004843, XP055664584, DOI: 10.1371/journal.ppat.1004843.

* cited by examiner

*Primary Examiner* — Mary Maille Lyons
(74) *Attorney, Agent, or Firm* — Fox Rothschild LLP

(57) ABSTRACT

This invention describes vaccine compositions and their methods of use utilizing inactivated fbp1Δ deletion mutant fungal cells.

18 Claims, 34 Drawing Sheets
Specification includes a Sequence Listing.

CD4
BALs_B6 Naive.fcs
Event Count: 114

CD4
BALs_Tube_001.fcs
Event Count: 24497

CD4
BALs_Tube_006.fcs
Event Count: 75206

CD4
BALs_Tube_004.fcs
Event Count: 8041

CD4
BALs_Tube_005.fcs
Event Count: 10563

CD4
BALs_Tube_003.fcs
Event Count: 42198

CD4
BALs_Tube_008.fcs
Event Count: 18126

CD4
BALs_Tube_002.fcs
Event Count: 28829

CD4
BALs_Tube_007.fcs
Event Count: 2482

FUNGAL VACCINE COMPOSITIONS AND METHODS OF USE THEREOF

CROSS-REFERENCE TO RELATED APPLICATIONS

The present application is a U.S. National Phase of International Patent Application No. PCT/US2017/041506, filed Jul. 11, 2017, which claims priority to U.S. Provisional Patent Application Ser. No. 62/360,588, filed Jul. 11, 2016, the disclosures of which are incorporated by reference in their entirety.

STATEMENT REGARDING FEDERAL FUNDING

This invention was made with government support under grant number 1R21A115204 awarded by the National Institute of Allergy and Infectious Disease (NIAID). The U.S. government has certain rights in the invention.

FIELD OF THE INVENTION

This invention relates to vaccine compositions and their methods of use. The vaccines utilize inactivated fbp1Δ deletion mutant cells and are effective to provide immunity in a host against infection by, e.g. a fungus.

BACKGROUND

Invasive fungal infections represent a significant public health concern, particularly in developing countries and those in tropical regions. Invasive fungal infections kill over 1.5 million people worldwide annually, and the number is expected to grow. Certain groups of individuals remain particularly susceptible to invasive fungal infection, including immunocompromised individuals, such as individuals infected with HIV or undergoing certain types of chemotherapy, as well as children and the elderly. One fungal species of particular interest is *Cryptococcus neoformans*, a basidiomycetous yeast pathogen, as it infects the central nervous system (CNS) and is the leading cause of fungal meningitis in immunocompromised populations worldwide, with roughly 1 million cases that account for approximately 600,000 deaths annually. Thus, *C. neoformans* represents a significant percentage of the total annual deaths caused by invasive fungal infections. Treatment for infection by *C. neoformans* is often accomplished with anti-fungal medication, such as fluconazole, but treatment is not always effective, especially in the immunocompromised people.

To date, only a few *C. neoformans* mutants have been found to be able to elicit protection against challenges with the highly virulent H99 strain of *C. neoformans*. The first strain developed in the H99 background was done by enforcing expression of murine IFN-γ in the yeast cells (γH99). Vaccination studies with γH99 have provided critical proof-of-principle evidence for the importance of type 1 immunity in protection as well as for the capacity of the host immune response to overcome virulence mechanisms of H99 given the proper inflammatory conditioning. Studies with simplified vaccines based on beta-glucan particles loaded with cryptococcal antigenic extracts have also been found to induce robust Th1 and Th17 responses that correlate with vaccine-mediated protection. However, no commercially available safe and reliable vaccine currently exists for *C. neoformans*. Because of this, there is an urgent need for such.

SUMMARY OF THE INVENTION

The present invention relates to fungal immunogenic compositions such as vaccine compositions and methods of use thereof. The present invention shows that vaccination by inactivated fbp1Δ deletion mutant, including partial deletion mutant, fungal cells surprisingly confers host immunity to fungal infection, for example but not necessarily limited to, infection by *C. neoformans*. In some embodiments, the present invention is directed to an immunogenic composition such as a vaccine composition. In some embodiments, the vaccine composition contains an inactivated fbp1Δ deletion mutant fungal cell. In some embodiments, the inactivated fbp1Δ deletion mutant fungal cell is a *C. neoformans* cell. In some embodiments, the vaccine composition contains a heat-killed fbp1Δ deletion mutant *C. neoformans* cell. In some embodiments, the fbp1Δ deletion mutant is a partial fbp1Δ deletion mutant. In some embodiments, the fbp1Δ deletion mutant is generated by homologous recombination. In some embodiments, the partial fbp1Δ deletion mutant is generated by homologous recombination. In some embodiments, the partial fbp1Δ deletion mutant has an F-box domain deleted. In some embodiments, the vaccine composition contains at least one adjuvant. In some embodiments, the vaccine composition contains at least one pharmaceutically acceptable carrier or excipient.

In some embodiments, the present invention is directed to a method of stimulating a host immune system or an immune response in a host. In some embodiments, the host is an immunocompromised host. In some embodiments, the immunocompromised host is infected with human immunodeficiency virus (HIV). In some embodiments, the method is directed to administration of a vaccine containing inactivated an fbp1Δ deletion mutant fungal cell. In some embodiments, the inactivated fbp1Δ deletion mutant fungal cell is a *C. neoformans* cell. In some embodiments, the method is directed to administration of a vaccine containing a heat-killed fbp1Δ deletion mutant *C. neoformans* cell. In some embodiments, the fbp1Δ deletion mutant is a partial fbp1Δ deletion mutant. In some embodiments, the fbp1Δ deletion mutant is generated by homologous recombination. In some embodiments, the partial fbp1Δ deletion mutant is generated by homologous recombination. In some embodiments, the partial fbp1Δ deletion mutant has an F-box domain deleted. In some embodiments, the vaccine composition is administered with at least one adjuvant. In some embodiments, the vaccine composition is administered with at least one pharmaceutically acceptable carrier or excipient. In some embodiments, the vaccine is administered more than once.

In some embodiments, the present invention is directed to a method of treating or preventing a fungal infection in a subject in need thereof. In some embodiments, the subject is an immunocompromised subject. In some embodiments, the immunocompromised subject is infected with human immunodeficiency virus (HIV). In some embodiments, the method generally comprises administering one or more doses of a vaccine formulation comprising an inactivated fbp1Δ deletion mutant according to any aspect of the present disclosure to the subject in need thereof. In some embodiments, the vaccine is administered more than once. In some embodiments, the fungal infection comprises an infection with virulent *C. neoformans*. In some embodiments, the virulent *C. neoformans* strain comprises strain H99. In some embodiments, the fungal infection comprises an infection with *C. albicans*, *A. fumigatus*, or *C. gattii*. In some embodiments, the method includes administering at least one antifungal agent to the subject in need thereof. In some embodiments, the antifungal agent comprises one of azole antifungals, echinocandins, polyenes, or other antifungal agents.

In some embodiments, the present invention is directed to an inactivated fbp1Δ deletion mutant for use in the treatment or prevention of a fungal infection. In some embodiments, the inactivated fbp1Δ deletion mutant is an inactivated fbp1Δ deletion mutant according to any aspect of the present disclosure.

In some embodiments, the present invention is directed to the use of an inactivated fbp1Δ deletion mutant for the manufacture of a medicament for the treatment or prevention of a fungal infection. In some embodiments, the inactivated fbp1Δ deletion mutant is an inactivated fbp1Δ deletion mutant according to any aspect of the present disclosure.

BRIEF DESCRIPTION OF THE DRAWINGS

FIG. 2A represents GXM secretion was measured after H99 and fbp1Δ strains were grown on capsule inducible minimum medium for three days. A typical yeast cell and the capsule of each strain was shown at the top following Indian ink staining. FIG. 2B represents 1D proton nuclear magnetic resonance (NMR) spectroscopy detection of the GXM structure produced by H99 and fbp1Δ cells. The spectrum peaks indicate the M2 mannosyl triad structure reporter groups. FIG. 2C represents cell cultures of H99 and fbp1Δ were incubated with FITC labeled Concanavalin A (ConA-FITC) and the fluorescence quantified using flow cytometry. The bar graph represents the average signal intensity. FIG. 2D represents chitin and chitosan production was compared between H99 and fbp1Δ cells grown on YPD overnight.

FIG. 3A represents colony forming units (CFU) of total fungal burden in the lung. Data shown is mean±SEM for 5-12 mice per group per time point cumulative of two independent experiments. FIG. 3B represents survival rates after infection in C57Bl/6J. Data shown for each graph is for 8 mice per group and cumulative of two independent experiments. FIG. 3C and FIG. 3D represent fungal burden as examined by CFU recovered in spleen (FIG. 3C) and brain (FIG. 3D). Data shown is mean±SEM for 5-12 mice per group per time point cumulative of two independent experiments. FIGS. 3E through 3H represent cellular infiltration to the lung was analyzed by flow cytometry. Each symbol represents one mouse, data is cumulative if two independent experiments. Each cell population was identified as $CD45^{45}DAPI^-$ live leukocytes, neutrophils were gated as $CD11b^+Ly6C^+Ly6G^+$ (FIG. 3E), monocytes were gated as $CD11b^+Ly6C^+Ly6G^-$ (FIG. 3F), $CD4^+$ T-cells were gated as $Thy1.2^+CD11b^-CD4^+CD8^-$ (FIG. 3G) and $CD8^+$ T-cells were gated as $Thy1.2^+CD11b^-CD4^-CD8^+$ (FIG. 3H). Statistical analysis, Mann-Whitney test. *p≤0.05, p≤0.01. Statistical analysis of survival curve was done by Log Rank (Mantel-Cox) test, *p≤0.001.

FIG. 4A represents survival pattern in A/J mice infected with $10^6$ fbp1Δ. FIG. 4B represents that HK-fbp1Δ vaccinated mice that survived without symptoms for more than 60 days contained a significant number of $CD4^+$ T-cells that remained in the airways. FIGS. 4C and 4D represent airway $CD4^+$ T-cells recovered from vaccinated mice rapidly produced IFN-γ (FIG. 4D) and IL-17A (FIG. 4C) upon re-stimulation. FIGS. 4E through 4G represent *Cryptococcus*-specific $CD4^+$ T-cell responses were sustained in the MLN of vaccinated mice, for IL-12 (FIG. 4E), IFN-γ (FIG. 4F) and IL-17A (FIG. 4G).

FIGS. 5A through 5F represent *Cryptococcus*-specific $CD4^+$ T-cell responses were examined in lung-draining lymph node (MLN) at days 3, 7 and after infection with H99 or fbp1Δ. $CD4^+$ T-cells were purified from the MLN of infected mice and stimulated with antigen-presenting cells in the presence or absence of *C. neoformans* (Cn) sonicated antigens. Data shown is for cytokines secreted to the supernatant after 72 hours of in vitro re-stimulation. No cytokines were detected in samples cultured without Cn antigen. Each symbol represents one mouse. Data shown is cumulative of three independent experiments with 4-5 mice per group. IL-2 (FIG. 5A), IFN-g (FIG. 5B), IL-17A (FIG. 5C), IL-4 (FIG. 5D), IL-5 (FIG. 5E) and IL-13 (FIG. 5F) cytokines were measured by ELISA. FIG. 5G represents a FACS plots of $CD4^+$ T-cells (top panel) and $CD8^+$ T-cells (bottom panel) in the bronchoalveolar lavage fluid (BALF). FIGS. 5H through 5K represent cytokine expression analyzed by intracellular cytokine staining (ICCS). Each symbol represents one mouse. Data is cumulative of 4 independent experiments with 5 mice per group. H-J) Plots shown are for cytokine production in $CD4^+$ T-cells gated as $Thy1.2^+CD4^+CD8^-$ T-cells. Frequency of IFN-γ (FIG. 5H) and IL-17A-(FIG. 5I) and TNF (FIG. 5J)-producing $CD4^+$ T-cells in BALF were analyzed as shown in FIG. 5G. FIG. 5K represents frequency of IFN-g-producing $Thy1.2^+CD4^-CD8^+$ T-cells. **p≤0.0001, *p≤0.001, **p≤0.01, *p≤0.05, as determined by Mann-Whitney test.

FIG. 6A represents survival rates of $RAG^{-/-}$ and wild type control mice after infection with fbp1Δ. FIG. 6B represents survival rates of $RAG^{-/-}$ and wild type control mice after infection with H99. FIG. 6C through 6E represent colony forming units in lung (FIG. 6C), brain (FIG. 6D) and spleen (FIG. 6E) of $RAG^{-/-}$ and WT mice infected with fbp1Δ. Each symbol represents one mouse. Data shown is cumulative of two independent experiments. **p≤0.0001, *p≤0.001 as determined by Log Rank (Mantel-Cox) test (FIG. 6A, 6B) or Mann-Whitney test (FIGS. 6C through 6E).

FIG. 7A represents a FACS profile of $Ly6C^+$ monocyte maturation into mo-DCs (defined as $CD45^+CD11b^+Ly6C^+Ly6G^-CD11c^+ClassII^+$) in H99 or fbp1Δ infected mice. FIG. 7B represents percent of mo-DCs ($CD11c^+ClassII^+$) in monocyte gate ($CD45^+CD11b^+Ly6C^{hi}Ly6G^-$) in mice infected with H99 or fbp1Δ. FIG. 7C represents total number of mo-DC recruited to the lung. FIG. 7D through 7F represent chemokine expression in lung tissue as analyzed by qRT-PCR; CCL2 (FIG. 7D), CCL7 (FIG. 7E), and CCL12 (FIG. 7F). The expression of each CCR2 ligand was examined using taq-man probes. Differential gene expression was calculated relative to GAPDH using the ΔΔCT method. **p≤0.01 as determined by Mann-Whitney test.

FIG. 8B represents survival curve of fbp1Δ-infected CCR2-depleted (dashed) and control littermates (solid). Data shown is cumulative of three independent experiments with 4-5 mice per group. **p≤0.0001 as determined by Log Rank (Mantel-Cox) test. FIG. 8C represents total number of CD4+ T-cells recovered from the BALF of fbp1Δ-infected CCR2-depleted and control littermates at day 6 after infection. Each symbol represents one mouse. Data shown is cumulative of two experiments with 4-5 mice per group *p≤0.001 as determined by Mann-Whitney test.

FIG. 8D represents a FACS profile of cytokine production by CD4+ T-cells recovered from the BALF of fbp1Δ-infected CCR2-depleted or control littermates. Plots are gated on Thy1.2+CD4+CD8− lymphocytes in BALF. FIG. 8E represents colony forming units in lung tissue of fbp1Δ-infected CCR2-depleted or control littermates at day 6 after infection. Data is cumulative of two independent experiments with 3-4 mice per group. *p≤0.001 as determined by Mann-Whitney test. FIG. 8F represents that cytokine gene transcription in lung tissue was examined at day 6 after infection with fbp1Δ in CCR2-depleted and control littermates (striped). Control B6 mice infected with H99 were also analyzed as a control population. Differential gene expression relative to GAPDH was examined by qRT-PCR using cytokine-specific Taq-Man probes and calculated using the ΔΔCt method. Data shown is cumulative of two independent experiments with 4 mice per group and is depicted as mean±SEM. p≤0.01 as determined by Mann-Whitney test.

FIGS. 13A and 13B represent CCR2+ monocyte and mo-DC recruitment to lung Day 3 after challenge. FIG. 13A represents total number of CCR+Ly6C+ monocytes in lung. FIG. 13B represents total number of CCR2+Ly6C+ CD11c+MHCII+mo-DC in lung. FIGS. 13C through 13E represent CD4+ T-cell responses in MLN at day 7 after challenge, for IL-12 (FIG. 13C), IFN-γ (FIG. 13D), and IL-17A (FIG. 13E).

FIG. 14A represents percent survival after H99 infection in naïve mice or mice vaccinated with HK-fbp1Δ. Data shown is cumulative of three independent experiments with a total of 18 mice per group on the C57Bl/6J background. FIG. 14B represents percent survival after H99 infection in naïve mice or mice vaccinated with HK-fbp1Δ. Data shown is cumulative of three independent experiments with a total of 15 unvaccinated and 21 fbp1Δ_vaccinated mice on the A/Jcr background. FIG. 14C represents percent survival after H99 infection in naïve mice or mice vaccinated with HK-H99 a total of 10 mice per group were analyzed in two independent experiments. FIG. 14D represents percent survival after H99 infection in naïve mice or RAG−/− that were unvaccinated and RAG−/− that were vaccinated with HK-fbp1Δ. Data shown is for 5-10 mice per group and is cumulative of two independent experiments. FIG. 14E represents total number of CD4+ T-cells recovered in the BALF of naïve mice or HK-fbp1Δ-vaccinated B6 mice that survived for 72 days after H99 challenge. Each symbol represents one mouse. FIG. 14F represents a FACS plot of intracellular cytokine production by CD4+ T-cell recovered from BALF of vaccinated B6 mice 72 days after H99 challenge. Percent IFN-γ and IL-17A-producing CD4+ T-cells in vaccinated mice as analyzed in FACS shown. Each symbol represents one mouse. Data shown is cumulative of 3 independent experiments. FIGS. 14G through 14I represent that CD4+ T-cells were isolated from the lung-draining lymph node of fbp1Δ-vaccinated that survived an H99 challenge for 72 days. Cytokine secretion (IL-1, FIG. 14G; IFN-γ, FIG. 14H; IL-17A, FIG. 14I) in the presence or absence of Cn antigens was examined by ELISA as described in materials and methods. Data shown is cumulative of three independent experiments with 4-5 mice per group and is depicted as mean±SEM. **p≤0.0001, * p≤0.001, **p≤0.01 as determined by Log Rank (Mantel-Cox) test (FIG. 14A, 14B) or Mann-Whitney test (FIG. 14E, 14G through 14I).

DETAILED DESCRIPTION OF THE INVENTION

The present invention is based at least in part on unexpected discoveries that vaccination by inactivated fbp1Δ deletion mutant, including partial deletion mutant, fungal cells surprisingly conferred host immunity to fungal infection, for example but not necessarily limited to, infection by *C. neoformans*. For example, Example 4 illustrates protection against infection with virulent *C. neoformans* (strain H99) and Example 5 illustrates protection against other pathogenic fungal species, e.g., *C. gattii.*

Fbp1 is a Grr1-like F-box protein (F-box protein 1) found in *C. neoformans* as well as a number of other fungal organisms, including pathogens. Fbp1 is important for fungal sexual reproduction (fungal sporulation), and is essential for virulence in *C. neoformans*. Specifically, Fbp1 is required for fungal proliferation in macrophages, after phagocytosis. The present disclosure identifies Fbp1 as a control point for how *C. neoformans*, e.g. H99 strain of *C. neoformans*, interacts with the host immune system. *Cryptococcus* Fbp1 shares sequence and structural similarity with Grr1 in *S. cerevisiae* and *C. albicans*. Both Grr1 proteins in the two yeasts are important for cell morphology, and grr1 mutants produce pseudohyphae. This is consistent with the observation that Grr1 in other plant-pathogenic fungi play a role in growth and fungal infectivity. F-box proteins are characterized by an F-box domain, first identified in human cyclin F. Fbp1 contains an F-box domain and 12 leucine-rich repeats (LRR). F-box proteins are exchangeable subunits that facilitate the capacity of SCF to specifically target a number of structurally and functionally diverse substrates.

The ubiquitin proteasome system is crucial for the controlled turnover of proteins in eukaryotic cells and thus plays an important role in the regulation of diverse cellular activities. As part of the $SCF^{Fbp1}$ ligase complex, Fbp1 contributes to the specificity of UPS degradation process by targeting specific proteins for ubiquitination. Similar to other F-Box proteins, it is possible that *C. neoformans* Fbp1 targets multiple proteins for degradation. Therefore the observed phenotype of fbp1Δ could be due to the aggregate function of altered turn over of multiple proteins. Alternatively, the effect of fbp1Δ on the host immune response could be due to the regulation of just one factor. A thorough analysis of Fbp1 targets so far failed to identify Znf2 or chitin deacetylases (CDA) as targets of Fbp1 regulation (data not shown). Thus, Fbp1 may act independently of Znf2 and CDA genes to regulate the immunogenicity of H99. Given that Znf2 and Fbp1 both have multiple, yet to be defined targets, it could be possible that there is a convergence of these two immunogenic strains on a common downstream target. Fbp1 physically interacts with Skp1 of the $SCF^{Fbp1}$ E3 ligase complexes to take part in protein ubiquitination and degradation. The E3 ubiquitin ligases are key enzymes in the UPS-mediated ubiquitination and degradation process. They function as the substrate recognition modules of the system and determine the specificity of protein degradation. The SCF E3 ligase complexes bind to substrates that contain specific recognition signals for ubiquitin-protein ligation and degradation, thereby determining the specificity of the regulatory system. Without wishing to be bound by theory, SCF(Fbp1) E3 ligase may regulate fungal pathogenesis through a mechanism that is independent of the classical virulence factors. As shown in Example 2 below, inositol phosphosphingolipid-phospholipase C1 (Isc1) is a substrate of Fbp1, and Isc1 is required for fungal virulence, which constitutes a novel regulatory connection between the SCF (Fbp1) E3 ligase complex and inositol sphingolipid biosynthesis in *C. neoformans.*

Fbp1 is coded for by the FBP1 gene in *c. neoformans*. Fbp1-knockout (KO) *C. neoformans* are avirulent, blocking basidospore production, as shown in Example 1 below. However, Fbp1 does not regulate cell morphology in *C. neoformans*, as fbp1Δ mutants produced normal yeast cells when grown in liquid medium. Surprisingly, Fbp1 is essential for fungal virulence yet is not involved in regulation of any of these well-studied virulence factors, an indication that additional virulence-controlling mechanisms are involved, as fbp1Δ knockouts produce normal virulence factors, including melanin, capsule, and the ability to grow at body temperature. Although Fbp1 is not involved in the development of virulence factors, it is important for maintaining cell membrane integrity. Many enzymes important for either cell wall construction or cell wall maintenance have been found to be critical for maintaining cell integrity, such as α-1,3-glucan synthase, the chitinase gene family and chitin/polysaccharide deacetylases, which control chitosan biosynthesis, and the KRE family, which is involved in β-1,6-glucan synthesis. However, most of these genes are important for cell wall integrity. The effect of Fbp1 on cell integrity is more specific to cell membranes, as it is sensitive to only SDS, as shown in Example 1 below. Without wishing to be bound by theory, Fbp1 may target certain membrane proteins that are important for membrane integrity for degradation. Fbp1 KO *C. neoformans* show defects in intracellular proliferation after phagocytosis, and cannot disseminate to other organs following pulmonary infection, as shown in Example 2 below.

Figure 1:
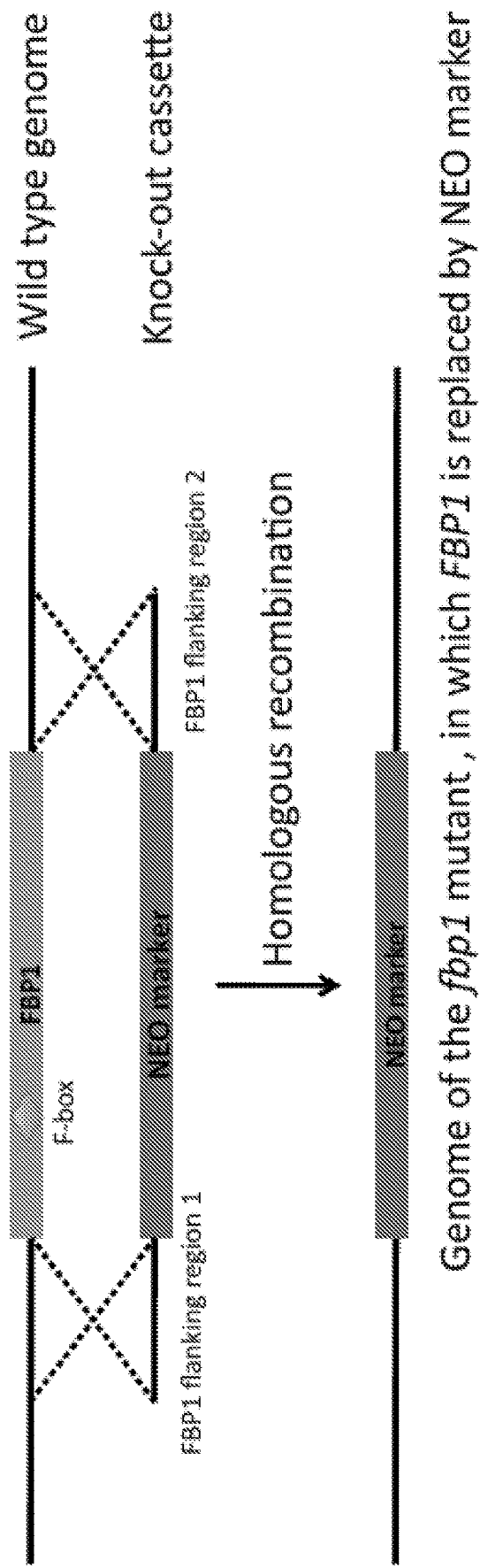
FIG. 1 represents a method for generating fbp1 deletion (knockout) mutants.

As shown in Examples 1 and 2 infra, generation of fbp1Δ KO mutants can occur via homologous recombination methods, for example, by replacing the wild type genome with a knock-out cassette, for example (but not necessarily) one containing a gene coding for a marker protein, for example (but not necessarily) a NEO marker as used in Example 1 infra, and is illustrated in FIG. 1. One skilled in the art will recognize that there are numerous knock-out cassettes which may be used, for example those containing NAT markers as also disclosed in Example 1, and that the thrust is to generate *C. neoformans* (for example) mutants lacking expression of Fbp1, such that the mutants are suitable for incorporation into a vaccine composition of the present invention as discussed herein. Furthermore, it is possible to create partial fbp1Δ knockouts that are functionally similar to full fbp1Δ knockout mutants. For example, knocking out just the F-box domain of Fbp1, as shown in Example 1, may result in a phenotype similar to the fbp1Δ null mutant (full fbp1 knockout). The method utilized for partial deletion knockouts is practically identical to that to create full length fbp1Δ KO mutants, in that the method utilizes homologous recombination with an expression cassette, only the region of genomic DNA that is replaced with, e.g. a marker (such as the NAT marker utilized in Example 1 infra), is limited to a portion of the complete gene, for example, but not necessarily, the region coding for the F-box domain of Fbp1. One of ordinary skill in the art will appreciate that there are other domains of Fbp1 which may be knocked out which still render the partial KO mutant phenotypically same or similar to the full-length KO mutant, and that the invention as directed to partial deletion/knockout mutants is not limited to just those partial deletion mutants that knock out the F-box domain of Fbp1, so long as the partial KO mutants are suitable for incorporation into a vaccine composition of the present invention.

Example 3 infra examines the underlying mechanisms that contribute to the in vivo hypovirulent phenotype of the fbp1Δ deletion mutants. It was found that infection with fbp1Δ mutants induced a robust inflammatory response and enhanced activation of innate and adaptive immune responses as compared to the parental H99 strain. Long-term protection from fbp1Δ infection was dependent on the activation of adaptive immune responses since lymphocyte-deficient mice ($RAG^{-/-}$) were not able to contain infection with fbp1Δ mutants and succumbed to infection. The activation of protective immunity against fbp1Δ mutants was also facilitated by increased innate responses. Infection with fbp1Δ induced a more robust recruitment of $Ly6C^+$ monocytes and their maturation into dendritic cells (mo-DCs) as compared with H99. Selective depletion of $CCR2^+$ cells in CCR2-DTR mice resulted in the abrogation of protective immunity and rapid mortality of fbp1Δ-infected mice. Example 4 infra illustrates that vaccination with inactivated (heat-killed) fbp1Δ deletion mutants results in the induction of immune responses that protect the host against a lethal challenge with the parental H99 strain. Without wishing to be bound by theory, it is believed that Fbp1 acts as a virulence factor that shapes the immunogenicity of *C. neoformans*. A disruption in this Fbp1-controlled pathway is sufficient to induce robust innate and adaptive immune responses that protect the host from infection and can be harnessed in the vaccination strategies of the present disclosure.

As illustrated in the Examples, the enhanced immunogenicity and vaccine potential of inactivated fbp1Δ deletion mutants are believed to be dependent on the increased recruitment of $CCR2^+Ly6C^+$ monocytes. Without wishing to be bound by theory, it is believed that an intact Fbp1-regulated pathway functions to inhibit the optimal recruitment and maturation of $CCR2^+Ly6C^+$ monocytes. The importance of this recruitment is demonstrated by the increased susceptibility of CCR2-depleted mice to fbp1Δ infection. $CCR2^+$ monocytes are precursors to monocyte-derived macrophages and dendritic cells (mo-DCs) that are important for control of multiple infections. Previous studies have shown that mo-DCs are crucial for the priming and Th1 differentiation of *Aspergillus-fumigatus*-specific $CD4^+$ T-cell responses. Similarly, $CCR2^+$ monocytes and their derivative cells are required for the induction of protective immunity to *Blastomyces dermatitidis* and other clinically important fungal pathogens. Inhibition of $CCR2^+$ monocyte recruitment has been shown to be a crucial mechanism of virulence exploited by *B. dermatitidis*. The present disclosure this shows that inhibition of $CCR2^+$ monocyte recruitment is similarly an important point of regulation by Fbp1-controlled targets that thus help shape the virulence of *C. neoformans*. Without wishing to be bound by theory, inhibition of $CCR2^+$ monocyte recruitment might thus be a common mechanism of virulence exploited by pathogenic fungi. Accordingly, as also illustrated by Example 4 and FIG. 15, inactivated fbp1Δ deletion mutants may exhibit cross-protectivity against different pathogenic fungal species.

In addition of acting as precursors of DCs for the activation of adaptive immunity, CCR2+ monocytes can give rise to direct effectors of innate-mediated control of fungal growth. The more rapid mortality of CCR2-depleted mice as compared with lymphocyte-deficient ($RAG^{-/-}$) in response to fbp1Δ infection is likely due to additional contributions of $CCR2^+$ monocytes as innate antifungal effectors. Protective immune responses to infection with *C. neoformans* strain 52D have been shown to be critically dependent on $CCR2^+$ monocytes and their derivative macrophages and DCs. Without wishing to be bound by theory, it might be possible that differential targeting of $CCR2^+$ monocyte recruitment by distinct *C. neoformans* isolates could underlie their variable virulence whereby more virulent strains like H99 inhibit CCR2 influx while less virulent ones like 52D do not. The inhibition of $CCR2^+$ monocyte recruitment and maturation is thus a potential virulence mechanism that can help fungal pathogens to escape both innate and adaptive immune-mediated control of infection. The results of Example 3 suggests that an Fbp1-regulated target/s is involved in regulation of such a mechanism of virulence in *C. neoformans*.

As shown in Example 4 infra, inactivated fbp1Δ deletion mutants are effective to prevent infection against fungal infection, particularly infection by *C. neoformans*. Surprisingly, live fbp1Δ deletion mutants were not effective vaccine compositions, whereas inactivated fbp1Δ deletion mutants were; see also FIG. 9. One of ordinary skill in the art will understand that although the Examples include in vivo studies on mice, that because the similarities of adaptive immunity between rodents and humans, the vaccine compositions of the present invention are suitable to prevent infection in humans and other mammals. The link between in vivo rodent studies and how such translates to use in humans is further discussed in Carninci P., "Genomics: Mice in the ENCODE spotlight," *Nature* 515, 346-347 (20 Nov. 2014), hereby incorporated by reference in its entirety. The fbp1Δ deletion mutant may be either a full fbp1Δ knockout or only a partial knockout as described herein. The fbp1Δ deletion mutant may be inactivated by heat (i.e. heat-killed) or by other means. As described herein, an inactivated vaccine (i.e. containing inactivated fbp1Δ deletion mutant) refers to a vaccine comprising fbp1Δ deletion mutants that have been killed, as opposed to live/attenuated vaccines. Inactivation preferably comprises heat-killing the fbp1Δ deletion mutants, but is considered to embody any method of killing the fungal cells without breaking them, so the cell surface of the comprising fbp1Δ deletion mutants remains intact. In addition to heat-killing such potential methods include, but are not limited to, irradiation (e.g. with gamma irradiation or similar methods) and chemical sterilization (e.g. with formaldehyde or other chemicals that leave the cell surface intact).

The vaccine compositions of the present invention may contain an antigen suitable for stimulating the host immune response. The antigen may contain a protein, a polypeptide, a peptide, an epitope, a hapten, or any combination thereof. The antigen can also contain a whole organism, killed, attenuated or live; a subunit or portion of an organism; a recombinant vector containing an insert with immunogenic properties. In certain embodiments the antigenic component can come from a disease-causing microorganism. In some embodiments, the antigen is an inactivated fbp1-KO fungal cell. In some embodiments, the inactivated fbp1-KO fungal cell is an inactivated fpb1-KO *C. neoformans* cell. In further embodiments, the vaccine composition contains a heat-killed fbp1Δ *C. neoformans* cell.

The present compositions may be used in an immunogenic composition to immunize an animal. An immunogenic composition according to the invention is preferably used for the preparation of a vaccine. Preferably a prophylactic and/or therapeutic vaccine is produced. Thus, within the scope of this invention is an immunogenic or vaccine composition that contains a pharmaceutically acceptable carrier and an effective amount of an antigen as described supra. The carriers used in the composition can be selected on the basis of the mode and route of administration, and standard pharmaceutical practice. The composition can also contain an adjuvant. Examples of an adjuvant include a cholera toxin (such as cholera toxin B), *Escherichia coli* heat-labile enterotoxin, liposome, monophosphoryl lipid A, unmethylated DNA (CpG) or any other innate immune-stimulating complex such as tetanus toxoid, diphtheria toxin, adenylate cyclase mutants, pertussis toxin, and derivatives thereof, and cytokines. Various adjuvants that can be used to further increase the immunological response depend on the host species and include Freund's adjuvant (complete and incomplete), mineral gels such as aluminum containing compounds, e.g. aluminum salts (alum), aluminum hydroxide, MF59, AS03, liposomal products such as virosome, AS04 (alum-adsorbed TLR4 agonist), surface-active substances such as lysolecithin, pluronic polyols, polyanions, peptides, oil emulsions, keyhole limpet hemocyanin, and dinitrophenol. Additional adjuvants include any disclosed in Lee et al. Immune Netw. (2015) 15(2): 51-57, hereby incorporated by reference in its entirety.

The present disclosure additionally relates to methods of preventing or treating a fungal infection in an individual or subject in need thereof. The method generally comprises administering one or more doses of a vaccine formulation comprising an inactivated fbp1Δ deletion mutant according to any aspect of the present disclosure to the subject in need thereof. The fungal infection is preferably infection with a virulent strain of *C. neoformans*, although the fungal infection is not limited as such as the vaccines of the present invention may be used to prevent infection by other fungal species than by *C. neoformans*. For example, in some embodiments, the fungal species comprises *C. albicans, A. fumigatus* or *C. gatti*. However, the invention is not limited as such.

For example, the fungal species may comprise any of the following fungal species. *Absidia corymbifera* or *ramose, Achorion gallinae, Actinomadura* spp., *Actinomyces* spp., *Ajellomyces dermatididis, Aleurisma brasiliensis, Allersheria boydii, Arthroderma* spp., *Aspergillus* spp. (including but not limited to *A. fumigatus, A. flavus*, and *A. lentulus*), *Basidiobolus* spp, *Blastomyces* spp, *Cadophora* spp, *Candida* spp (including but not limited to *C. albicans, C. krusei, C. galbrata, C. rugose, C parapsilosis, C. tropicalis*, and *C. dubliniensis*), *Cercospora apii, Chrysosporium* spp, *Cladosporium* spp, *Cladothrix asteroids, Coccidioides immitis, Cryptococcus neoformans* (including strain H99), *Cunninghamella elegans, Dematium wernecke, Discomyces israelii, Emmonsia* spp, *Emmonsiella capsulate, Endomyces geotrichum, Entomophthora coronate, Epidermophyton floccosum, Filobasidiella neoformans, Fonsecaea* spp., *Geotrichum candidum, Glenospora khartoumensis, Gymnoascus gypseus, Histoplasma* spp, *Hormiscium dermatididis, Hormodendrum* spp, *Keratinomyces* spp, *Langeronia soudanense, Leptosphaeria senegalensis, Lichtheimia corymbifera, Lobmyces loboi, Loboa loboi, Lobomycosis, Madurella* spp., *Malassezia furfur, Microsporum* spp (including but not limited to "ringworm"), *Monilia* spp, *Mucor* spp., *Nannizzia* spp., *Neotestudina rosatii, Nocardia* spp., *Oidium albicans, Oospora lactis, Paracoccidioides brasiliensis, Petriellidium boydii, Phialophora* spp., *Piedraia hortae, Pityrosporum furfur, Pneumocystis* spp. (including but not limited to *P. carinii/P. jirovecii*), *Pullularia gougerotii, Pyrenochaeta romeroi, Rhinosporidium seeberi, Sabouraudites, Sartorya fumigate, Sepedonium, Sporotrichum* spp., *Tinea* spp. (also including but not limited to "ringworm"), *Torula* spp, *Trichophyton* spp (also including but not limited to "ringworm"), *Trichosporon* spp, *Zopfia rosatii*, and combinations thereof.

The vaccine formulations may be administered (e.g., but not necessarily, co-administered) with one or more antifungal agents. The antifungal agents may include but are not limited to azole antifungals, echinocandins, polyenes, or other antifungal agents. Specific antifungal agents include, but are not limited to, anidulafungin, caspofungin, clotrimazole, econazole nitrate, miconazole, terbinafine, fluconazole, ketoconazole, amphotericin (including amphotericin B), flucytosine, itraconzaole, micafungin, posconazole, isavuconazole, voriconazole, nystatin, girseofulvin, and combinations thereof.

The vaccine formulations may be administered to a subject per se or in the form of a pharmaceutical or therapeutic composition. Compositions of the invention and an adjuvant may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen.

For injection, vaccine preparations may be formulated in aqueous solutions, preferably in physiologically compatible buffers such as Hanks' solution, Ringer's solution, phosphate buffered saline, or any other physiological saline buffer. The solution may contain formulatory agents such as suspending, stabilizing and/or dispersing agents. Alternatively, the compositions described herein may be in powder form for constitution with a suitable vehicle, e.g., sterile pyrogen-free water, before use.

The amount of a composition administered depends, for example, on the particular antigen in the composition, whether an adjuvant is co-administered with the antigen, the type of adjuvant co-administered, the mode and frequency of administration, and the desired effect (e.g., protection or treatment), as can be determined by one skilled in the art. Determination of an effective amount of the vaccine formulation for administration is well within the capabilities of those skilled in the art, especially in light of the detailed disclosure provided herein. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1-36 week period. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 pg. Suitable dose range will vary with the route of injection and the size of the subject, but will typically range from about 0.1 mL to about 5 mL. Sera can be taken from the subject for testing the immune response or antibody production elicited by the composition against the antigen. Methods of assaying antibodies against a specific antigen are well known in the art. Additional boosters can be given as needed. By varying the amount of the composition and frequency of administration, the protocol can be optimized for eliciting a maximal production of the antibodies.

A composition of this invention can be administered parenterally, orally, nasally, rectally, topically, or buccally. A sterile injectable composition can be a solution or suspension in a non-toxic parenterally acceptable diluent, solvent, or carrier. Such solutions include, but are not limited to, 1,3-butanediol, mannitol, water, Ringer's solution, and isotonic sodium chloride solution. In addition, fixed oils can be conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. When aqueous suspensions or emulsions are administered orally, the active ingredient can be suspended or dissolved in an oily phase combined with emulsifying or suspending agents. If desired, certain sweetening, flavoring, or coloring agents can be added.

As used herein, the terms "antigenic agent," "antigen," or "immunogen" mean a substance that induces a specific immune response in a host animal. As used herein, the term "immunogenic" refers to a capability of producing an immune response in a host animal against an antigen or antigens, e.g. heat-killed fbp1Δ C. neoformans cells. This immune response forms the basis of the protective immunity elicited by a vaccine against a specific infectious organism. An "immune response" refers to a response elicited in an animal, which may refer to cellular immunity (CMI); humoral immunity or both.

The terms "co-administration," "co-administered," and "in combination with" as used herein may refer to the administration of at least two agents or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

As used herein, the term "pharmaceutical composition" may refer to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient, e.g. heat-killed fbp1-KO C. neoformans cells, and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Specific examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone (PVP); amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN; polyethylene glycol (PEG), and PLURONICS. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington: The Science and Practice of Pharmacy (Remington the Science and Practice of Pharmacy) Twenty-First Edition (2005), hereby incorporated by reference in its entirety.

As used herein, a "patient" or "subject" may refer to a biological system to which a treatment can be administered. A biological system can include, for example, an individual cell, a set of cells (e.g., a cell culture), an organ, a tissue, or a multi-cellular organism. For example, a "patient" or "subject" may refer to human and non-human animals. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model. The term "animal" includes all vertebrate animals including humans. In particular, the term "vertebrate animal" includes, but not limited to, humans, canines (e.g., dogs), felines (e.g., cats); equines (e.g., horses), bovines (e.g., cattle), porcine (e.g., pigs), as well as in avians. The subject may or may not be an immunocompromised subject, e.g. a subject infected with human immunodeficiency virus (HIV) or suffering from another condition or pathology that results in reduced ability to fight infection.

As used herein, the terms "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing as well as after their appearance. In addition, "treating" or "treatment" does not require complete alleviation of signs or symptoms, does not require a cure, and specifically includes protocols that have only a marginal effect on the patient. Thus, "treating" or "treatment" additionally includes "preventing" or "prevention" of disease. The terms "prevent" or "preventing" or "prevention" refer to prophylactic and/or preventative measures, wherein the object is to prevent or slow down the targeted pathologic condition or disorder. These terms are not limited solely to a situation in which the patient experiences no aspect of the condition whatsoever. For example, a treatment will be said to have "prevented" the condition if it is given during exposure of a patient to a stimulus that would have been expected to produce a given manifestation of the condition, and results in the patient's experiencing fewer and/or milder symptoms of the condition than otherwise expected. For example, a treatment can "prevent" infection by resulting the patient's displaying only mild overt symptoms of the infection; it does not imply that there must have been no cellular damage caused by the infecting fungal organism.

As used herein, an "effective amount" refers to the amount of an active compound/agent that is required to confer a therapeutic effect on a treated subject. Effective doses will vary, as recognized by those skilled in the art, depending on the types of conditions treated, route of administration, excipient usage, and the possibility of co-usage with other therapeutic treatment. A therapeutically effective amount to treat or inhibit a fungal infection is an amount that will cause a reduction in one or more of the manifestations of fungal infection, such as amount of fungus present in the host organism and mortality as compared to untreated control animals.

As used herein, the term "parenteral" refers to subcutaneous, intracutaneous, intravenous, intramuscular, intraarticular, intraarterial, intrasynovial, intrasternal, intrathecal, intralesional, or intracranial injection, as well as any suitable infusion technique.

As used herein, the terms "purified" or "isolated" antibody, peptide, polypeptide, or protein may refer to a peptide, polypeptide, or protein, as used herein, may refer to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis.

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference in their entireties.

As used herein and in the appended claims, the singular forms "a", "and" and "the" include plural references unless the context clearly dictates otherwise.

The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values. Context in individual circumstances will dictate to what range of values the term "about" refers. Accordingly, the term "about" may or may not refer to different ranges of values throughout this disclosure.

Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

Each of the applications and patents cited in this text, as well as each document or reference, patient or non-patient literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The following non-limiting examples serve to further illustrate the present invention.

EXAMPLES

1. Fbp1 Regulates Sexual Reproduction and Virulence in *Cryptococcus neoformans*

This example studies the function of F-box protein Fbp1, including fbp1Δ mutants. This example shows that the F-box protein Fbp1 is essential for fungal sporulation and virulence in *C. neoformans*.

Materials and Methods

Strains of *C. neoformans* and *S. cerevisiae* were grown at 30° C. on yeast extract-peptone-dextrose (YPD) agar medium and synthetic (SD) medium. J774 murine macrophages were grown in 10-cm petri dishes in liquid Dulbecco modified Eagle's (DME) medium with 10% fetal calf serum (FCS) (ATL Biologicals, GA), 10% NCTC-109 (Gibco), and 1% nonessential amino acids (MP Biomedicals, OH). Modified MS medium (Murashige and Skoog medium) was used for mating and sporulation assays.

To test the expression of Fbp1 during mating and how Fbp1 is expressed in response to glucose, fbp1 expression was measured at mRNA levels throughout the mating process and under conditions with or without glucose via quantitative real-time PCR (qRT-PCR). Cultures of *C. neoformans* var. *grubii* wild-type strain H99 and its near congenic strain KN99a were grown overnight on YPD liquid medium with shaking. Cells from an H99 overnight culture were collected and washed with distilled $H_2O$ ($dH_2O$) and then resuspended in medium with 2% glucose (YPD) or 2% galactose (YPG) and incubated for 2 h. Cells were then collected and washed with $dH_2O$. The cells collected from YPD were resuspended in YPG, while the cells collected from YPG were resuspended in YPD. Both cultures were incubated for 2 h. Total RNAs were prepared from the cells with each treatment, and cDNA was synthesized as described below.

Mating was performed by mixing H99 and KN99a, which were then co-cultured on V8 medium (pH 5.0). Mating mixtures were collected from agar surfaces using cell scrapers after 6, 24, 48, 72, or 96 h of incubation. The collected cells were washed with $dH_2O$, and the pellets were used for total RNA extraction. Total RNAs were extracted using Trizol reagent (Invitrogen) and purified with the Qiagen RNeasy cleanup kit (Qiagen) following the manufacturer's instructions. The purified RNAs were used as templates for PCR amplification with primers of the glyceraldehyde-3-phosphate dehydrogenase gene (GAPDH) to determine potential genomic DNA contamination. Purified RNAs were quantified using a Nanodrop spectrometer (Thermo Scientific).

First-strand cDNAs were synthesized using a Superscript III cDNA synthesis kit (Invitrogen) following the manufacturer's instructions. Expression of fbp1 and gapdh was analyzed using SYBR advantage QPCR premix reagents (Stratagene). Primer efficiency was determined by serially diluting the cDNA and monitoring DNA amplification by real-time PCR. Gene expression levels were normalized using the endogenous control gene GAPDH, and the relative levels were determined using the comparative threshold cycle ($C_T$) method. Real-time PCRs were performed using an Mx4000 QPCR system (Stratagene). The specificity of the PCR was further verified by subjecting the amplification products to agarose gel electrophoresis and sequencing them.

The fbp1Δ mutants were generated in both H99 and KN99a strain backgrounds by overlap PCR. See FIG. 1. The 5' and 3' regions of each fbp1 gene were amplified from H99 genomic DNA with primers CX278/CX279 (SEQ ID NO: 20 and SEQ ID NO: 21), and CX280/CX281 (SEQ ID NO: 22 and SEQ ID NO: 23), respectively. The dominant selectable markers (NEO$^r$) were amplified with the M13 primers, M13F (SEQ ID NO: 1) and M13R (SEQ ID NO: 2), from plasmid pJAF1. Each target gene replacement cassette was generated by overlap PCR with primers CX278 (SEQ ID NO: 20) and CX281 (SEQ ID NO: 23). The purified overlap PCR products were precipitated onto 10-μL gold microcarrier beads (0.6 μm; Bio-Rad), and strain H99 or KN99a was biolistically transformed. Stable transformants were selected on YPD medium containing G418 (200 mg/liter). To screen for mutants of the fbp1 gene, diagnostic PCR was performed by analyzing the 5' junction of the disrupted mutant alleles with primers CX284 (SEQ ID NO: 26) and JH8994 (SEQ ID NO: 29). Positive transformants identified by PCR screening were further confirmed by Southern blot analysis.

To generate complemented strains of fbp1 mutants, a genomic DNA fragment that contains a 1.5-kb upstream promoter region, the fbp1 open reading frame (ORF), and its 500-bp downstream region was amplified in a PCR using primers CX285 (SEQ ID NO: 27) and CX286 (SEQ ID NO: 28). This PCR fragment was fused with the NAT$^r$ selective marker gene at its C terminus in an overlap PCR using primers CX285 (SEQ ID NO: 27) and M13R (SEQ ID NO: 2). The overlap PCR product was biolistically transformed in both a and a mating-type fbp1 mutant strains. Mating assays were performed to identify transformants that complemented the fbp1 phenotype.

To generate strains expressing Fbp1 lacking the F-box domain, the F-box domain sequence was deleted by amplifying two fragments from H99 genomic DNA with primers CX225/CX198 (SEQ ID NO: 30 and SEQ ID NO: 16) and CX199/CX231 (SEQ ID NO: 17 and SEQ ID NO: 47) respectively. Overlap PCR was performed by using the mixture of two fragments as a template with primers CX225 (SEQ ID NO: 30) and CX231 (SEQ ID NO: 47). The amplified overlap PCR product contains the fbp1 gene lacking the F-box domain sequence and was cloned into vector pJAF13, which contains the NAT$^r$ selective marker, to generate the construct pCUX58. pCUX58 was introduced and expressed in the fbp1Δ mutant background by biolistic transformation. The expression of Fbp1 lacking an F-box domain was confirmed by Western blot analysis.

Melanin production was assayed by inoculating C. neoformans strains into 2 mL YPD liquid medium and incubating them overnight at 30° C. Five microliters of each overnight culture with series dilutions was placed on 1-3,4-dihydroxyphenylalanine (1-DOPA) agar medium (13 mM glycine, 15 mM glucose, 29.4 mM KH2PO4, 10 mM MgSO4.7 H2O, 3 μM thiamine, 5 μM d-biotin, 2% agar, 1 mM 1-DOPA, pH 5.5). The agar plates were incubated at 30° C. or 37° C. for 2 days, and the pigmentation of fungal colonies was assessed.

To examine capsule production, yeast cells were grown in YPD broth overnight at 37° C. with constant agitation, washed 3 times with phosphate-buffered saline (PBS), and re-suspended at a concentration of $1 \times 10^6$ cells/mL in various media: DME medium, PBS, or YPD broth. Cells were added to 6-well plates and incubated with or without the addition of 10% heat-inactivated FCS and in the absence or presence of 10% $CO_2$ for 24 h. The capsule size was visualized by adding a drop of India ink to the cell suspensions and observing them on an Olympus (Melville, N.Y.) AX70 microscope using a 100× objective. The cells were analyzed using the ImageJ 1.40 g software by measuring the distance from the cell wall to the capsule edge (India ink exclusion zone). The average and standard deviation from 15 to 30 cells were calculated for each condition tested.

In a mating assay, C. neoformans cells of opposite mating types were mixed and cocultured on V8 or MS agar medium at 25° C. in the dark. Mating filaments and basidiospore formation were examined and recorded by photography using the Olympus CX41 light microscope after incubation for 7 to 10 days. Mating results were also examined using scanning electron microscopy (SEM).

DAPI (4',6-diamidino-2-phenylindole) staining was performed with minor modification. Cell cultures and mating filaments were fixed with formaldehyde (9.3%) for 10 min. The fixed cells were washed twice with PBS, permeabilized with an equal volume of PBS buffer containing 1% Triton X-100 for 5 min, washed twice again with PBS, and resuspended in PBS. For DAPI staining, equal volumes of cell suspension and DAPI mixture (20 ng/mL DAPI, 1 mg/mL antifade, 40% glycerol) were mixed and observed with a Nikon fluorescence microscope.

Trypan blue staining was performed. Briefly, strains were inoculated in 5 mL YPD liquid medium and grown for 2 days at 30° C. Yeast cells were mixed with an equal volume of 0.4% trypan blue solution and viewed through an Olympus CX41 light microscope. The percentages of cells that were able to take up dye (dark blue) were calculated by counting at least 500 yeast cells for each strain.

Yeast two-hybrid interaction assays were performed. The fbp1 full-length cDNA and partial cDNA lacking the F-box domain, full-length cDNAs of skp1 homologues in strain H99 (Cnskp1) and S. cerevisiae (Sc skp1), and crk1 cDNA were cloned into the bait vector pGBKT7 and fused with the BD domain. cDNAs of fbp1, Cnskp1, and Scskp1 were also cloned into the prey vector pGADT7 and fused with the AD domain. All inserted cDNA sequences were confirmed by sequencing. Both bait constructs and prey constructs were cotransformed into the yeast strain PJ69-4A. Transformants growing on SD medium lacking histidine or adenine were considered positive interactions. The expression of the LacZ gene in these transformations was quantified by β-galactosidase enzyme activity assays using chlorophenol red-β-D-galactopyranoside (CPRG) (Calbiochem, San Diego, Calif.) as a substrate.

Phagocytosis assays were performed in 96-well plates, using J774 macrophages at a concentration of $2.5 \times 10^4$ cells/well that were allowed to double overnight at 37° C. in activating medium (DME medium, 50 U/mL of gamma interferon [IFN-γ], 1 μg/mL of lipopolysaccharide [LPS]). PBS-washed fungal cells were opsonized with 20% mouse complement (Pel-Freez, AK) and added to the macrophages at an effector-to-target ratio of 1:2. Phagocytosis was allowed to occur for 2 h at 37° C. in 10% $CO_2$. The cells were then washed three times with PBS and fixed with methanol at −20° C. for 30 min. Giemsa stain was added to the wells at a dilution of 1:20, and the plates were incubated at room temperature for 30 min. The wells were washed once with PBS and analyzed using an inverted microscope. For each well, 3 different fields were counted, for a total of at least 100 macrophages. The percent phagocytosis was determined by dividing the number of macrophages that contained C. neoformans by the total number of macrophages counted.

To check macrophage antifungal activity, phagocytosis was allowed to occur for 3 h and 24 h. After each time interval, medium was removed from the well and transferred to an Eppendorf tube containing sterile PBS. Macrophages were lysed by adding sterile $dH_2O$ to each well and incubating the plate for 45 min at room temperature. Fluid was transferred to each respective tube after resuspension. Fungal cells were counted, appropriate dilutions were made, and approximately 200 cells were plated on YPD agar plates. The colonies on each plate were counted after 2 days of incubation at 37° C. to determine the actual number of live cells per well.

Yeast strains were grown at 30° C. overnight, and the cultures were washed twice with PBS buffer and re-suspended at a final concentration of $2 \times 10^6$ CFU/ml (colony forming units/mL). Groups of 10 female A/Jcr mice (NCI, Frederick, Md.) were intranasally infected with $10^5$ cells of each yeast strain. Over the course of the experiments, animals that appeared moribund or in pain were sacrificed by $CO_2$ inhalation. Survival data from the murine experiments were statistically analyzed between paired groups using the log-rank test with PRISM version 4.0 (GraphPad Software, San Diego, Calif.) (P values of <0.001 were considered significant).

Infected animals were sacrificed at the endpoint of the experiment according to the University of Medicine and Dentistry of New Jersey (UMDNJ) IACUC-approved animal protocol. For mice infected by the fbp1 mutant strain, the experiment was terminated 60 days post infection. To compare the fungal burdens and host inflammatory responses, lungs and brains from mice infected by H99, the fbp1 mutant, or the complemented strain of the fbp1 mutant were isolated at 10 or 20 days post infection, fixed in 10% formalin solution, and sent to the AML laboratory for section preparation (AML Laboratories, Inc. Rosedale, Md.). Lungs and brains infected by the fbp1 mutant were also isolated at the endpoint of the experiment (60 days post infection). Tissue slides were stained with hematoxylin and eosin (H&E) and examined by light microscopy. Infected lungs, brains, and spleens were also isolated and homogenized using a homogenizer in PBS buffer. Resuspensions were diluted, 100 μL of each dilution was spread on YPD medium with ampicillin and chloramphenicol, and colonies were determined after 3 days of incubation at 30° C.

Results

Fbp1 contains 928 amino acids (SEQ ID NO: 48) with an F-box domain (SEQ ID NO: 49) and an LRR domain containing at least 12 LRRs. Fbp1 shows sequence similarity to several F-box proteins reported in fungi, including Grr1 in S. cerevisiae and C. albicans, GrrA in A. nidulans, and Fbp1 in F. graminearum. Fbp1 showed 19% protein sequence identity and 33% sequence similarity with Grr1, suggesting it could also be an important nutrient regulator. Due to the importance of nutrient sensing and its regulation in both the development and pathogenesis of C. neoformans, the function of Fbp1 was investigated.

Mating between H99 and KN99a was performed on V8 mating medium, and mating mixtures were collected from plates after incubation for 0, 6, 24, 48, 72, and 96 h. RNAs were purified, and qRT-PCR was performed. The results indicate that the expression of fbp1 was significantly down-regulated during mating, especially after 72 h, compared to expression at the 0-h time point, an indication that the fbp1 plays a role in later stages of sexual reproduction after cell fusion. qRT-PCR results showed that fbp1 expression was moderately upregulated in response to the glucose starvation caused by switching cultures from YPD (2% glucose) to YPG (2% galactose) for 2 h, indicating that expression of fbp1 is subject to glucose repression.

In S. cerevisiae, Grr1 functions as a repressor of glucose repression and is also involved in cell cycle regulation. Overnight cultures of grr1 mutants grown on YPD quickly flocculated without being shaken and mutant cells were elongated. To examine whether Fbp1 is an ortholog of Grr1, the pGBKT7 vector expressing Fbp1 or Grr1 was transformed into a grr1 mutant strain. Reintroducing the GRR1 gene complements the grr1 mutant on cell morphology. However, no morphological change was observed when Fbp1 was expressed in a grr1 mutant strain, which was confirmed by RT-PCR (not shown), indicating Fbp1 could not complement the function of Grr1 in S. cerevisiae. Because cell morphology was not altered in C. neoformans fbp1 mutants, Fbp1 has different functions than Saccharomyces Grr1.

Hxt3 is a glucose transporter, and its expression is induced by either low or high glucose concentrations in S. cerevisiae in a Grr1-dependent manner. A homologue of HXT3 in C. neoformans (CnHXT3; CNAG_03372.2) was identified. The expression of CnHXT3 under different glucose conditions was measured by qRT-PCR and compared between wild-type H99 and the fbp1 strain. When cells grown on medium without glucose (YPG, 2% galactose) were switched to glucose-rich medium (YPD, 2% glucose) for 2 h to generate glucose induction conditions, expression of CnHXT3 was higher in the fbp1 mutant background and was downregulated in the H99 background. n the other hand, when cells grown on YPD were switched to medium without glucose (YP, no glucose; YP0.1, 0.1% glucose; or YPG, 2% galactose) to generate glucose starvation conditions, CnHXT3 expression was not significantly altered in the wild-type strain but was upregulated in fbp1 mutants. These results indicated that CnHXT3 expression was repressed by a high glucose concentration and induced by glucose starvation. Fbp1 negatively regulates CnHXT3 expression under these conditions.

fbp1 deletion mutants were generated in both *C. neoformans* H99 and KN99a strain backgrounds. The development of dikaryotic hyphae and basidiospores was examined in both fbp1 unilateral mating (fbp1×wild type) and bilateral mating (fbp1×fbp1). No obvious phenotypic changes were observed in fbp1 unilateral-mating assays. The bilateral mating between fbp1 mutants failed to produce basidiospores, even though it produced normal dikaryotic hyphae, indicating that Fbp1 is essential for sporulation. As the F-box domain of an F-box protein is important for its function the role of the F-box domain in Fbp1 function was investigated by generating strains expressing Fbp1 lacking the F-box domain (Fbp1$^{\Delta FB}$), which contains a 6× His tag at the C-terminal end. The expression of Fbp1$^{FB}$ in fbp1 mutants was confirmed by Western blot analysis using anti-His antibody. The mating results showed that bilateral mating between strains expressing Fbp1$^{\Delta FB}$ (Fbp1$^{\Delta FB}$×Fbp1$^{\Delta FB}$) could not produce spores, similar to the bilateral mating of fbp1 mutants, indicating the F-box domain is essential for Fbp1 function in mating.

The development of fungal nuclei at different stages of sexual reproduction by DAPI staining was investigated to understand why fbp1 mutants fail to produce spores. A single nucleus in each yeast cell was observed in both the wild-type and the fbp1 mutant cultures, and two separated nuclei can be observed in each dikaryotic hypha produced from bilateral-mating mixtures after cell fusion. A single fused nucleus could be observed in each young basidium of both the wild type and fbp1 mutants after mating mixtures were incubated for 3 days, indicating that both strains undergo normal nuclear fusion to produce basidia during mating. However, nuclei in the bilateral mating of fbp1 mutants failed to undergo meiosis after fusion, and only a single nucleus was observed in each mature basidium after 14 days of incubation, while all basidia from wild-type mating produced four nuclei. This observation suggested that Fbp1 is important for regulating meiosis during mating, which could explain the defect of sporulation in bilateral mating of fbp1 mutants. Because fbp1 mutants have a normal growth rate and also have normal nuclear division when grown in rich medium, Fbp1 may not be involved in the cell cycle during mitotic division; rather, it plays a role only in regulating meiosis. To confirm these observations, fluorescence-activated cell sorter (FACS) analysis was performed for both H99 and fbp1 mutants cultured in YPD liquid medium and minimal medium. No difference was observed between the wild-type strain and the fbp1 mutant, which confirmed that Fbp1 is dispensable for mitotic cell division in *C. neoformans*.

In *C. neoformans*, several virulence factors that are important for fungal virulence have been well characterized in vitro, including production of a polysaccharide capsule and melanin, as well as the ability to grow at mammalian body temperature. The development of these virulence factors infbp/mutants was examined in vitro. fbp1 mutants produced normal melanin on both Niger seed agar and L-DOPA agar, produced regular capsules on DME medium, and also showed normal growth at 37° C., indicating that Fbp1 is not important for development of these virulence factors in vitro.

The capsule size of *C. neoformans* can be further induced by the presence of high $CO_2$ concentrations and serum. The capsule enlargement under such inducible conditions is similar to what has been observed in vivo during infection, since 10% $CO_2$ and serum are part of the physiological condition in mammals. The ability of capsule to grow under such conditions is important for fungal pathogenicity. To test whether Fbp1 plays a role in capsule growth under such inducible conditions, capsule sizes of fbp1 mutants were examined after they were treated with 10% $CO_2$ and 10% heat-inactivated FCS. Yeast cells were grown on different culture media, including rich medium (YPD), PBS buffer, and DME medium, and the cultures were treated with 10% $CO_2$, 10% FCS, or both. The results showed that in every medium tested, the capsule sizes of both H99 and fbp1 mutants were significantly enlarged in the presence of 10% $CO_2$ or 10% $CO_2$ plus 10% FCS. However, there was no significant difference between H99 and fbp1 mutants, indicating Fbp1 is dispensable for capsule growth under these inducible conditions.

The virulence of fbp1 mutants were examined. Consistent with previous studies, mice infected by the H99 wild-type strain were terminated around 18 to 22 days post inoculation due to lethal infection. However, fbp1-infected mice stayed healthy and continued to gain body weight even after 60 days post infection. A complemented strain of the fbp1 mutant developed lethal infection in mice around 24 days, which confirmed that the avirulent or hypovirulent phenotype in fbp1 mutants is caused by the deletion of the FBP1 gene.

The fungal burdens of infected mice were evaluated at the endpoint of the infection experiments. Lungs, spleens, and brains from three mice infected by each fungal strain were isolated, and the fungal loads in these organs were measured as yeast CFU per gram fresh organ. The results showed that when mice infected by the wild-type strain, H99, were sacrificed around 20 days, $10^9$, $10^5$, and $10^6$ CFU were isolated in mouse lung, brain, and spleen, respectively. Mice inoculated with fbp1 mutant cells were sacrificed 60 days post inoculation, and mouse organs were isolated to examine the fungal burden. No yeast cells were recovered in fbp1-infected spleen and brain, and only an average of $10^3$ yeast CFU were observed in each gram of lung.

Fungal lesion development in lung and brain was also visualized in H&E-stained slides. At either 10 or 20 days post-infection, both the wild-type H99 and the complemented strain caused severe damage in infected lungs, with abundant yeast cells containing big capsules. In contrast, only very limited damage was produced in the fbp1 mutant-infected lung, with very few yeast cells observed at both time points. There was no obvious difference between brains infected by any of the three strains at 10 days post infection. However, at 20 days post infection, severe organ damage with visible lesion development was observed in brains infected by H99 or the complemented strain, while no detectable damage or lesion was detected in brains infected by the fbp1 mutant. Even at 60 days post infection, the fbp1 infection caused only very limited damage in lungs and did not cause any lesion development in brains. These results demonstrate that Fbp1 is essential for the development of cryptococcosis.

*C. neoformans* can proliferate inside macrophages as an intracellular pathogen. To evaluate whether the avirulent phenotype of fbp1 mutants could be due to increased susceptibility to macrophage killing during fungus-macrophage interactions, the sensitivity of the fbp1 mutant to phagocytotic killings in the J774 murine macrophage cell line was tested. In these studies, no significant difference was observed in the internalization of yeast cells in macrophages. The macrophage antifungal activity assay also showed that the number of CFU recovered from the fbp1 mutant is similar to that from the wild-type strain H99 after coinoculation with activated macrophages in DME medium for either 3 h or 24 h, suggesting that the fbp1 mutant strain is equally resistant to macrophage killing. fbp1 mutants appeared to be less viable when incubated in DME tissue culture medium alone or co-incubated with inactivated macrophages for 24 h, suggesting that the fbp1 mutant grows better inside the macrophage, perhaps by obtaining nutrients from host cells.

The growth of fbp1 mutants was tested under osmotic stress (1.5 M NaCl, 1 M or 2.5 M sorbitol) and oxidative stress (2.5 mM $H_2O_2$), but no growth defect was observed. The cell integrity of fbp1 mutants was examined by applying several chemicals that target cell integrity, such as SDS, CFW, and Congo red. SDS disrupts the plasma membrane and lyses cells with a defective membrane, while CFW specifically binds to chitins and Congo red binds to β-1,4-glucans of the cell wall to disrupt cell wall integrity. The results showed that fbp1 mutant cells were hypersensitive to 0.05% SDS, but not CFW or Congo red, an indication that fbp1 mutants have cell membrane defects. Expressing Fbp1 lacking the F-box domain (Fbp1$^{\Delta FB}$) in an fbp1 mutant background could not rescue the growth defect on YPD with SDS, further supporting the idea that the F-box domain is essential for the function of Fbp1. Because trypan blue only stains cells with membrane defects or dead cells, wild-type H99, fbp1 mutants, and strains expressing Fbp1$^{\Delta FB}$ were stained with trypan blue after being cultured at 30° C. for 48 h in YPD liquid medium with shaking. The results showed that while approximately 0.7% of H99 cells were heavily stained, over 12% of fbp1 mutant cells and Fbp1$^{\Delta FB}$ cells were stained under the same conditions. These results further indicate that Fbp1 is important for maintaining cell membrane integrity.

F-box proteins involved in SCF E3 ligase function regulate cellular processes mostly through substrate proteins. To examine whether Fbp1 is a subunit of an SCF E3 ubiquitin ligase complex, protein-protein interaction assays were performed between Skp1 in *S. cerevisiae* (ScSkp1) and Fbp1 in a yeast two-hybrid system. A homologue of ScSkp1 was identified in *C. neoformans*, CnSkp1 (CNAG_00829.2). Interactions between CnSkp1 and Fbp1 were also performed. Fbp1, ScSkp1, and CnSkp1 were fused with both the activation domain (AD) and the binding domain (BD). Constructs containing Skp1 homologues and Fbp1 were cotransformed into the yeast strain pJ69-4A, and interacting transformants were screened on SD dropout medium (SD-Trp-Leu-His and SD-Trp-Leu-His-Ade). The expression of the LacZ gene was determined by detecting the β-galactosidase enzyme activity. The results showed that both ScSkp1 and CnSkp1 interacted with Fbp1 in a yeast two-hybrid protein-protein interaction system. Deletion of the F-box domain in Fbp1 eliminated its interaction with either ScSkp1 or CnSkp1, indicating that the F-box domain is essential for these interactions.

Because Fbp1 is essential for sporulation, homologues of Grr1 substrates in *S. cerevisiae* that are involved in meiosis regulation were searched for. In *S. cerevisiae*, the serine/threonine kinase Ime2 is a key regulator of meiosis, and its degradation is Grr1 dependent. Crk1 was identified as a Cdk-related kinase that shares sequence homology with both Ime2 in *S. cerevisiae* and Crk1 in *Ustilago maydis*. Crk1 interacts with Fbp1 in the yeast two-hybrid system and could potentially be a substrate of Fbp1. In the yeast two-hybrid protein-protein assays, besides the positive control, only colonies expressing both Fbp1 and Crk1 grew on SD-Trp-Leu-His-Ade medium, indicating a strong interaction between the two proteins. This strong interaction was also evident in the high β-galactosidase enzyme activities.

2. Fbp1-Mediated Ubiquitin-Proteasome Pathway Controls *Cryptococcus neoformans* Virulence by Regulating Intracellular Growth Materials and Methods

*C. neoformans* strains were grown at 30° C. on yeast extract-peptone-dextrose (YPD) agar medium and synthetic (SD) medium. Strains containing genes controlled by the CTR4 promoter were grown in YPD medium supplemented with either 25 μM $CuSO_4$ and 1 mM ascorbic acid or 200 μM bathocuproinedisulfonic acid (BCS). The pCTR4-2 plasmid was obtained from Washington University, St. Louis, Mo., while the pCN19 plasmid was obtained from Duke University. The isc1Δ mutant and its complemented strain were kindly provided by Maurizio Del Poeta at Stony Brook University. The macrophage-like murine cell line J774 was grown in 10-cm petri dishes in liquid Dulbecco modified Eagle's medium (DMEM) with 10% heat-inactivated fetal calf serum (FBS) (ATL Biologicals), 10% NCTC-109 (Gibco), and 1% nonessential amino acids (MP Biomedicals).

For SDS sensitivity testing, SDS was added to YPD to a final concentration of 0.2% (wt/vol), and 2× serial dilutions were prepared in 96-well plates. Cells of H99, the fbp1Δ mutant, and its complemented strain were added to the wells to a final optical density at 600 nm ($OD_{600}$) of 0.01. The plates were kept at 30° C., and the $OD_{600}$ was measured every 24 h. For inhibitor assays, MG132 (Sigma-Aldrich) or PS-341 (LC Laboratories) was added to the YPD liquid medium with 0.025% SDS to a final concentration of 100 μM or 200 μM, respectively. Twofold serial dilutions were prepared in 96-well plates. The wild-type H99 strain was added to the well containing proteasome inhibitors (MG132 or PS-134) and SDS to a final $OD_{600}$ of 0.01. The fbp1Δ mutant was added to YPD with 0.025% SDS only to a final $OD_{600}$ of 0.01. The growth of cultures was determined by measuring the $OD_{600}$ every 24 h.

Macrophage-like J774 cells were cultured in DMEM with 10% heat-inactivated FBS at 37° C. with 5% $CO_2$. A total of 5×10$^4$ J774 cells in 0.5 ml fresh DMEM were added to each well of a 48-well culture plate and incubated at 37° C. in 5% $CO_2$ overnight. To activate macrophage cells, 50 units/ml gamma interferon (IFN-γ; Invitrogen) and 1 μg/ml lipopolysaccharide (LPS; Sigma) were added to each well. *C. neoformans* overnight cultures were washed with phosphate-buffered saline (PBS) twice and opsonized with 20% mouse complement. A total of 2×10$^5$ *Cryptococcus* cells were added to each well (yeast/J774 cell ratio, 4:1). To assess intracellular proliferation of *C. neoformans*, nonadherent extracellular yeast cells were removed by washing with fresh DMEM after 2 h of co-incubation, and cultures were incubated for another 0, 2, or 22 h. At the indicated time points, the medium in each well was replaced by distilled water ($dH_2O$) to lyse macrophage cells for 30 min at room temperature. The lysate was spread on YPD plates, and the number of CFU was counted to determine intracellular proliferation.

For time-lapse movie production, activated macrophage cells (2×10$^5$) and opsonized *Cryptococcus* cells (2×10$^6$) were co-incubated in a 30-mm MatTek glass-bottom dish (coated). After 2 h of incubation, the culture was washed with fresh DMEM twice to remove detached yeast cells and replaced by 2 ml fresh DMEM. Seventeen-hour time-lapse movies with 2 min per frame were taken using a Nikon Eclipse AIRS confocal microscope. A total of 15 different views were taken for every 2 min. Resulting movies were analyzed using the software Nis Elements Viewer (Nikon).

All statistical analysis was undertaken using the Student t test. P values of <0.001 were considered statistically significant.

*Cryptococcus* cells from overnight culture or mating cultures were collected. Total RNA extraction and first-strand cDNA synthesis were performed. Expression of ISC1 and GAPDH was analyzed using SYBR advantage QPCR premix reagents (Clontech). Gene expression levels were normalized using the endogenous control gene GAPDH, and the relative levels were determined using the comparative threshold cycle ($C_T$) method. Quantitative real-time PCRs (qRT-PCRs) were performed using an Mx4000 QPCR system (Stratagene).

The fbp1 full-length cDNA was amplified with primers CX225 (SEQ ID NO: 30) and CX443 (SEQ ID NO: 31). The fbp1 cDNA lacking the F-box domain was amplified by overlap PCR using primers CX198-CX199 (SEQ ID NO: 16 and SEQ ID NO: 17) and CX225-CX443 (SEQ ID NO: 30 and SEQ ID NO: 31). Both fragments were cloned into the BamHI/NotI sites of a vector containing the *Cryptococcus* actin promoter and a Flag epitope, generating plasmids pCXU115 and pCXU117, which contain FBP1:Flag and FBP1$^{\Delta F}$:Flag fusions, respectively. The above plasmids were biolistically transformed into the fbp1Δ ura5Δ strain to generate strains CUX138 and CUX135, which express Fbp1:Flag and Fbp1$^{\Delta F}$: Flag proteins, respectively. The ISC1 cDNA was amplified with primers CX551 (SEQ ID NO: 37) and CX552 (SEQ ID NO: 38) and cloned into the BamHI sites of pCTR4-2 vector by use of an In-Fusion HD cloning kit (Clontech), generating the Isc1-hemagglutinin (HA) fusion plasmid pCXU170. To test the stability of Isc1 in the wild-type and fbp1Δ mutant strain backgrounds, pCXU170 and pCXU108 were biolistically transformed into the wild-type strain and an fbp1Δ mutant to generate strains CUX160 plus CUX167 and CUX118 plus CUX119, respectively.

To test the stability of Isc1 and Crk1 in the wild-type and fbp1Δ mutant strain backgrounds, Isc1:HA-tagged strains CUX167 and CUX168 and Crk1:HA-tagged strains CUX118 and CUX119 were grown to mid-logarithmic phase in YPD, transferred to YPD with 25 μM $CuSO_4$ and 1 mM ascorbic acid, and further incubated for the indicated amount of time. Protein extracts were prepared. Isc1:HA was detected by Western blotting using a monoclonal anti-HA antibody (GenScript).

The purification of Flag-tagged Fbp1 was done using EZview Red anti-Flag M2 affinity gel (Sigma-Aldrich). Cells were grown in YPD, harvested and washed with ice-cold water, and transferred into 2-ml bead-beating tubes containing 600 μl acid-washed glass beads. The proteins were extracted in lysis buffer (50 mM Tris-HCl, pH 7.4, 150 mM NaCl, 1 mM EDTA, 1% Triton X-100) by lysing cells at 4° C. with glass beads (four times for 20 s each) in a FastPrep FP120 apparatus (MP Biomedical). The protein extracts were collected after 15 min of centrifugation at 14,000 rpm at 4° C. Flag-tagged proteins were affinity purified under native conditions. Protein elutions were prepared by using SDS-PAGE sample buffer without reducing agents such as 2-mercaptoethanol or dithiothreitol (DTT).

To test the interaction between Fbp1 and Isc1 in vivo, Flag-tagged proteins were purified from strains CUX160, CUX140, and CUX141 by using anti-Flag affinity gel and then analyzed by immunoblotting with anti-Flag and anti-HA antibodies, respectively. To identify the proteins interacting with Fbp1, the Flag-tagged strains CUX138 and CUX135 were cultured in YPD medium, and the Flag-tagged proteins were purified using anti-Flag affinity gel and sent to the Center for Advanced Proteomics Research at Rutgers for mass spectrometry (liquid chromatography-tandem mass spectrometry [LC-MS/MS]) analysis.

Yeast strains were grown at 30° C. overnight, and cultures were washed twice with PBS and re-suspended at a final concentration of $2 \times 10^6$ CFU/mL. Groups of 10 female A/Jcr mice (NCI-Frederick) were infected intranasally with $10^5$ yeast cells of each strain. For the intravenous injection model, mice were inoculated with $5 \times 10^4$ cells via tail vein injection. Over the course of the experiments, animals that appeared moribund or in pain were sacrificed by $CO_2$ inhalation. Survival data from the murine experiments were statistically analyzed between paired groups by using the log rank test in Prism 4.0 (GraphPad Software) (P values of <0.01 were considered significant).

Infected animals were sacrificed at designated time points and the endpoint of the experiment according to the Rutgers Institutional Animal Care and Use Committee (IACUC)-approved animal protocol. Infected lungs and brains were isolated, fixed in 10% formalin solution, and sent to the Rutgers Histology Core Facility. Tissue slides were stained with hematoxylin and eosin (H&E) and examined by light microscopy. Infected lungs, brains, and spleens were also isolated and homogenized in 1×PBS by use of a homogenizer. Resuspensions were diluted, 100 μl of each dilution was spread on YPD medium with ampicillin and chloramphenicol, and numbers of colonies were determined after 3 days of incubation. All statistical analyses were undertaken using the Student nest. P values of <0.05 were considered statistically significant.

Results

Example 1 supra shows that fbp1Δ null mutant is hypovirulent in a murine model of systemic infection. Mice infected by the mutant strain are asymptomatic even after 60 days post-infection, in contrast to the average survival rate of 20 to 25 days when infected by wild-type H99. No yeast cells were recovered from the brains or spleens of mice that were infected by the fbp1Δ mutant, and only ~300 yeast CFU in each lung were recovered at 60 days post infection, compared to ~$10^8$ CFU in wild-type infection at the endpoint of the infection. To better understand the dynamic of the fbp1Δ mutant-host interaction during the infection process, fungal burdens in infected lungs were examined at 3, 7, 15, and 50 days post-inoculation. The results showed that fungal cells in fbp1Δ mutant-infected lungs remained at a persistently low level (~$10^3$ CFU/g fresh lung) throughout the infection process. Fungal lesion development in the lung was also visualized in H&E-stained slides. Wild-type strain H99 caused severe damage in infected lungs, with abundant yeast cells, as early as 3 days post-inoculation. In contrast, lungs infected by the fbp1Δ mutant showed little damage, with very few yeast cells observed at different time points and predominantly localized intracellularly.

Studies with animal models in vivo demonstrated that the fbp1Δ mutant cannot disseminate to infect other organs following pulmonary infection with $10^5$ cells. To better understand the role of Fbp1 in fungal dissemination, a murine intravenous injection model of cryptococcosis was applied to investigate whether the mutant simply cannot leave the lung or can leave the lung but cannot cross the blood-brain barrier (BBB) to cause central nervous system (CNS) infection. The results showed that the fbp1Δ mutant still caused lethal infection but had significant virulence attenuation compared to the wild type and the complemented strain (fbp1Δ strain plus FBP1). All mice (n=5) infected by H99 or the complemented strain died at around 7 to 8 days post-injection. Three mice infected by the mutant died at 15 to 25 days post-injection, while the other two fbp1Δ mutant-infected mice were still alive and had no sign of disease even at 37 days post-injection, when this experiment was terminated. Because both mouse groups infected by H99 or the complemented strain were terminated at around 7 days, organs were isolated from three mice infected by the mutant at 7 days post-infection for comparison. The analysis of yeast CFU counts and lesion development in infected brains showed that the fbp1Δ mutant could still cause infection in the brain, but the numbers of CFU were significantly reduced compared to those in mice infected by the wild-type strain. At the endpoint for fbp1Δ mutant-infected mice, three sick mice contained comparable numbers of CFU in both brains and lungs, while the two remaining, non-symptomatic mice at 37 days post-infection contained significantly smaller fungal burdens in both brains and lungs. The results indicate that Fbp1 is required but not essential for dissemination from the bloodstream to the brain. Therefore, fbp1Δ mutants could not leave the infected lung when the mice were infected via nasal inhalation.

Because the CFU results showed that the fbp1Δ mutant remains at a persistent level in infected lungs throughout the course of intranasal infection, it was hypothesized that fbp1Δ mutants may have a defect in proliferation inside macrophages and that extracellular fungal cells may not be able to grow in the hostile host environment. To investigate how deletion of the FBP1 gene influences the interaction with host cells, Cryptococcus-macrophage interaction assays were performed by using the murine J774 macrophage-like cell line in 48-well plates. Two hours after co-incubation of opsonized Cryptococcus cells and activated macrophages, non-adherent extracellular yeast cells were removed by washing with fresh medium and incubated for another 0, 2, or 22 h before macrophages were lysed by $H_2O$. The results showed that after 2 h of incubation, the number of yeast CFU recovered from macrophages co-incubated with the fbp1Δ mutant was comparable to that for cells co-incubated with the wild type or the complemented strain, suggesting a similar level of phagocytosis, which is consistent with Example 1 supra. However, after 4 h of incubation, significantly fewer CFU were recovered from the fbp1Δ mutant-interacting macrophages ($P<0.001$), i.e., only 36% of the CFU recovered from macrophages infected by the wild type. The ratio was reduced to 1:26 after 24 h of incubation. Surprisingly, while a significantly larger number of CFU was recovered from macrophages infected by the wild type after 24 h, recovered mutant cells remain at a persistently low level. By testing the fungal growth rate in DMEM without macrophages, it was found that both the wild-type and the mutant had similar growth in this medium. These results suggest that the fbp1Δ mutant proliferates very slowly once it is engulfed by macrophages, which, without wishing to be bound by theory, could be one reason why the fbp1Δ mutant cannot leave the lung and disseminate to the brain in the mouse systemic infection model.

To better understand the role of Fbp1 in Cryptococcus-macrophage interaction, the numbers of extracellular CFU of both the wild type and the fbp1Δ mutant were measured after co-incubation with activated macrophages for 2, 4, and 24 h. The results showed that similar number of extracellular CFU were recovered between the wild type and the fbp1Δ mutant after 2 and 4 h of incubation. However, the number of CFU of the fbp1Δ mutant was only 57% that for the wild type, on average, after 24 h of co-incubation. Because the wild type and the fbp1Δ mutant had similar growth rates in DMEM, the difference in numbers of extracellular CFU between these two strains in cultures with activated macrophages may have been caused by chemicals secreted by macrophages. To test this possibility, the growth assay was performed on these strains with a spent medium from an activated macrophage culture grown under the same conditions. The results showed that the number of CFU recovered by the fbp1Δ mutant was ~63% of that for the wild-type strain, on average, after 24 h of incubation, which supports the hypothesis that compounds secreted by activated macrophages likely can inhibit the fbp1Δ mutant's growth during coincubation, in addition to the intracellular growth arrest of the mutant. Because the difference in intracellular growth between the wild type and the fbp1Δ mutant was >25-fold, compared to an 2-fold difference in the growth in extracellular medium, it was concluded that Fbp1 plays a critical role in fungal intracellular proliferation in macrophages. This notion was confirmed by time-lapse movies showing the replication of yeast cells inside macrophages in real time. Much slower proliferation of the mutant cells than the wild-type H99 cells inside macrophages was observed.

Example 1, supra, showed a direct interaction between Fbp1 and the Skp1 homolog in C. neoformans in a yeast two-hybrid system, indicating that Fbp1 is part of an SCF E3 ligase complex. To further investigate Fbp1 function, an immunoprecipitation (IP) assay was performed to pull down Fbp1-interacting proteins. An FBP1 overexpression construct tagged with a Flag epitope at the carboxy terminus of the Fbp1 protein (Fbp1:Flag) was generated, in which Fbp1 expression is under the control of the Cryptococcus actin promoter. Using the same strategy, the Flag tag was also fused to an Fbp1 construct lacking the F-box domain (Fbp1$^{\Delta F}$: Flag). The Fbp1:Flag and Fbp1$^{\Delta F}$: Flag constructs were expressed in an fbp1Δ mutant background. Fbp1-associating proteins were purified by immunoprecipitation with an anti-Flag monoclonal antibody (mAb). As a control, a strain expressing a Flag tag fused to the Gα protein Gpa1 (Gpa1:Flag), which is functionally unrelated to Fbp1, was also generated, and the same immunoprecipitation method was used to purify Gpa1:Flag-binding proteins as a control. Protein pulldown results were analyzed by LC-MS/MS analysis.

Based on the LC-MS/MS analysis of the IP results, 21 proteins were identified that were observed only in the strains expressing the Fbp1:Flag or Fbp$^{\Delta F}$:Flag construct, not in the Gpa1:Flag-expressing strain, suggesting that they may specifically interact with Fbp1. Among them were a Skp1 homologue and a Cdc53/Cullin homologue, and both of them were pulled down only by Fbp1:Flag, not by Fbp1$^{\Delta F}$:Flag, indicating that Fbp1 likely associates with Skp1 and Cdc53 through the F-box domain to form an SCF E3 ligase complex in C. neoformans.

Example 1 supra showed that Fbp1 is required for cell membrane integrity and that both the fbp1Δ mutant and strains expressing the Fbp1 allele lacking the F-box domain are hypersensitive to SDS. To test whether SDS sensitivity is regulated by the SCF(Fbp1) E3 ligase function, the effects of proteasome inhibitors on Cryptococcus SDS sensitivity was investigated. Fungal growth rates of the wild-type H99 strain, the fbp1Δ mutant, and its complemented strain on YPD medium containing 0.025% SDS were determined in the absence or presence of the proteasome inhibitor MG132 or PS-341. MG132 is a cell-permeative proteasome inhibitor which can reduce the degradation of ubiquitin-conjugated proteins by the 26S complex without affecting its ATPase or isopeptidase activity. PS-341 is a potent and reversible proteasome inhibitor that functions to degrade intracellular polyubiquitinated proteins. In these assays, the fbp1Δ mutant had growth defects, while the wild type and the complemented strain exhibited normal growth on YPD agar medium containing 0.025% SDS. Neither 25 μM MG132 nor 100 μM PS-341 alone affected the growth of the wild-type strain or the mutant. Surprisingly, when grown on YPD medium containing both SDS and a proteasome inhibitor (either MG132 or PS-341), the wild type and the complemented strain showed a significant growth defect that was similar to the growth rate of the fbp1Δ, mutant in YPD with SDS alone. These results indicate that treatments with proteasome inhibitors lead to the SDS hypersensitivity of wild type *Cryptococcus*, which mimics that of the fbp1Δ mutant, strongly suggesting that Fbp1 is part of the ubiquitin-proteasome system and likely regulates cell membrane integrity through its E3 ligase function. Therefore, without wishing to be bound by theory, certain substrates of Fbp1 may also participate in regulation of cell membrane integrity.

Because E3 ligases usually interact with phosphorylated substrates for ubiquitination and eventual degradation, other proteins that were pulled down by Fbp1 in the immunoprecipitation analysis were analyzed to identify potential Fbp1 substrates. Besides the SCF(Fbp1) E3 ligase components, 18 other proteins interacted with both Fbp1:Flag and Fbp1$^{\Delta F}$:Flag in the IP pulldown and LC-MS/MS analyses, which were selected as potential substrate candidates. The protein sequence of an E3 ligase substrate usually contains the PEST domain, a sequence rich in proline (P), glutamic acid (E), serine (S), and threonine (T), which is a signature of the short-half-life proteins that are commonly targeted for degradation by the ubiquitin-proteasome system. Among the 18 proteins identified, 12 possessed putative PEST domains in their protein sequences, based on the ePESTFind program, including the inositol phosphorylsphingolipid phospholipase C1 Isc1 and the iron regulator Cir1.

Isc1 in *C. neoformans* is an enzyme involved in inositol sphingolipid metabolism, as it stimulates the activity to break down inositol phosphorylceramide (IPC) into phytoceramide and phosphorylinositol. Isc1 has been found to be required for intracellular growth of *Cryptococcus* in macrophages, a function shared by Fbp1. Isc1 has three putative PEST domains, suggesting that it could be a target of the ubiquitin-proteasome pathway. Cir1 is an iron-responsive transcription factor that controls the regulation of genes for iron acquisition and the known major virulence factors of the pathogen, including capsule and melanin production and the ability to grow at body temperature (37° C.). Cir1 is degraded by a ubiquitin-proteasome system, but the nature of the potential E3 ligase remains unknown. Cir1 contains two putative PEST domains. Therefore, Isc1 and Cir1 may be substrates of the SCF(Fbp1) E3 ligase, however, the involvement of Cir1 in the development of major virulence factors is different from the Fbp1 function.

Because a substrate of Fbp1 will likely be accumulated in an fbp1Δ mutant background due to a lack of proper ubiquitination and degradation, ISC1 overexpression strains were generated in which ISC1 expression is under the control of the *Cryptococcus* actin promoter. Compared to its expression in the wild type, the expression of ISC1 in the overexpression strains was increased over 300-fold as detected by qRT-PCR. To fully evaluate the function of Isc1, a isc1Δ mutant for this study was utilized. The potential role of Isc1 in regulating cell membrane integrity was examined by observing the SDS sensitivity phenotype of the ISC1 overexpression strains and the isc1Δ mutant cells. All overexpression strains were sensitive to SDS treatment, as they had growth defects in medium containing 0.025% SDS. These strains grew normally in the presence of the cell wall-destabilizing agents calcofluor white (CFW) and Congo red, which is consistent with phenotypes of the fbp1Δ mutant. The isc1Δ mutant was sensitive to SDS as well. The SDS sensitivity phenotype of both null mutants and overexpression strains of Isc1 suggests that the expression of Isc1 is tightly regulated and that proper expression is necessary for its normal cellular function. The phenomenon that deletion or overexpression of a target gene leads to similar phenotypes has also been documented in other organism.

To further examine the potential interaction between Isc1 and Fbp1, an Isc1 expression construct in the vector pCTR4-2 was generated in which Isc1 was fused with an HA tag at its C terminus and was under the control of an inducible CTR4 promoter that is induced by BCS and repressed by copper. The construct expressing the Isc1:HA fusion protein was introduced into an Fbp1:Flag overexpression strain and the fbp1Δ mutant background. The total protein from the strain expressing both Fbp1:Flag and Isc1:HA was purified using EZview Red anti-Flag M2 affinity gel and immunoblotted with anti-Flag and anti-HA antibodies. Both Flag and HA signals were detected from the co-IP product, demonstrating that Isc1 interacts with Fbp1 in *C. neoformans*.

To evaluate the hypothesis that Isc1 is an Fbp1 substrate, it was examined whether the stability of the Isc1 protein is dependent on SCF(Fbp1) E3 ligase function. The Isc1:HA fusion construct was expressed in the wild-type H99 strain and the fbp1Δ mutant, and the stability of the Isc1:HA protein was examined in these strain backgrounds. Strains expressing the Isc1:HA fusion protein were first grown in YPD medium with 200 μM BCS to induce the CTR4 promoter and then washed with PBS. Washed cultures were transferred to YPD containing 25 μM CuSO$_4$ and 1 mM ascorbic acid to block the transcription of ISC1:HA. Cells were collected after 0, 1, 2, and 4 h of incubation, and the abundance of the Isc1:HA protein was measured by Western blotting. In these assays, the Isc1:HA protein was degraded in a time-dependent manner over the period examined (0 to 4 h) in the wild-type background, but it was relatively stable in the fbp1Δ mutant, indicating that the stability of Isc1:HA is dependent on Fbp1.

To test whether Isc1 accumulated in the fbp1Δ mutant background, another Isc1:HA fusion construct in which ISC1 was controlled by its native promoter was made and transformed into H99 and the fbp1Δ mutant background. The abundance of the Isc1:HA protein was measured by Western blotting. The signal of Isc1:HA in the fbp1Δ mutant background was much stronger than that in the wild-type strain, but it was weaker than that in strains expressing Isc1:HA under the control of the CTR4 promoter. The presence of a single ectopic copy of the ISC1:HA gene in these strains was confirmed by Southern blotting. This result demonstrates that Isc1 is stabilized in the fbp1Δ mutant background, suggesting that Isc1 is a substrate of Fbp1 in *C. neoformans*.

Isc1 has been reported to play a key role in protecting *C. neoformans* from the intracellular environment of macrophages and is important for fungal dissemination to the central nervous system and the development of meningoencephalitis. Since Fbp1 is also required for *Cryptococcus*-macrophage interaction and for fungal dissemination, the connection between the Fbp1 E3 ligase and Isc1 was further investigated. As an Fbp1 substrate, the Isc1 protein is stabilized in an fbp1Δ mutant background. Therefore, the role of Isc1 in fungal virulence was investigated by using both the isc1Δ mutant and its overexpression strain.

In a murine inhalation model of cryptococcosis, virulence attenuation was observed in both the isc1Δ mutant and its overexpression strain. All mice infected with $10^5$ yeast cells of wild-type strain H99 had a median survival time of 20 days due to lethal infection. In contrast, both the isc1Δ mutant and the ISC1 overexpression strain showed significant virulence attenuation, with median survival times of 29 and 25 days, respectively. To test whether an isc1Δ mutation can partially rescue the hypovirulence of the fbp1Δ mutant, an isc1Δ fbp1Δ double mutant was generated. Mice infected by the isc1Δ fbp1Δ double mutant developed lethal infections by 40 days post inoculation indicating that the isc1Δ mutation partially rescued the virulence attenuation of the fbp1Δ mutant.

To better understand the virulence attenuation of the Isc1-related strains, the disease progression was investigated by examining the fungal burdens of infected lungs and brains in a time course study. Mouse lungs and brains infected by the wild type, the ISC1 overexpression strain, or the isc1Δ mutant were isolated at 3, 7, and 14 days post infection. The results showed that lungs infected by either the isc1Δ mutant or the ISC1 overexpression strain showed around 10 times fewer CFU at 7 and 14 days post infection than the H99-infected lungs, but the difference was not significant at 3 days post infection. Brains infected by the isc1Δ mutant showed significantly reduced fungal burdens throughout the infection process, showing that Isc1 is required for dissemination. Fungal burdens in brains infected by the ISC1 overexpression strain were also reduced, but to a lesser extent, consistent with the survival curve for infected mice. These outcomes suggest that the Isc1 protein level may be tightly regulated by the Fbp1 E3 ligase, and levels that are too high or too low could lead to virulence attenuation.

To better understand how Fbp1 may regulate Isc1 function in vivo, the *Cryptococcus*-macrophage interaction in the isc1Δ mutant and its overexpressed strain was tested. The results found that both strains showed reduced intracellular growth, a phenotype observed in the fbp1Δ mutant as well, with the ISC1 overexpression strain showing a lesser defect than the null mutant. he isc1Δ fbp1Δ double mutant also showed a significant intracellular growth defect, but it was much less severe than that of the fbp1Δ single mutant, which is consistent with the conclusion that Isc1 is a downstream target of Fbp1.

A growth assay of the wild type and the fbp1Δ mutant under either nitrosative or oxidative stress conditions. Compared to the wild-type strain, the isc1Δ mutant, fbp1Δ mutant, isc1Δ fbp1Δ double mutant, and ISC1 overexpression strains all had growth defects under nitrosative stress conditions, although the sensitivities of the fbp1Δ mutant and the ISC1 overexpression strain were not as high as that of the isc1Δ mutant. Oxidative stress response assays showed a less conclusive outcome. The isc1Δ mutant and isc1Δ fbp1Δ double mutant showed high sensitivity to 5 mM $H_2O_2$ at low pH (pH 4.0), but the fbp1Δ and ISC1 overexpression strains did not show significant differences compared to wild-type strain H99. The function of Isc1 in the nitrosative stress response is regulated by the Fbp1 E3 ligase, but its function in the oxidative stress response may be regulated by some other upstream factors.

3. The F-Box Protein Fbp1 Shapes the Immunogenic Potential of *Cryptococcus neoformans*

Materials and Methods

Mice

Age and sex matched mice of the A/Jcr and C57BL/6 genetic backgrounds were obtained from the Jackson Laboratories. CCR2-depleter mice (CCR2-DTR) in the B6 background were generated. For studies with CCR2-depleter sex and age-matched littermates were used as control mice. RAG1−/− lymphopenic mice were purchased from the Jackson Laboratories. All mouse strains were maintained and bred at the Rutgers-NJMS Cancer Center Research Animal Facility under specific pathogen-free conditions. Animal studies were performed following biosafety level 2 (BSL-2) protocols approved by the Institutional Animal Care and Use Committee (IACUC) of Rutgers University under protocol 15041D. The studies performed were governed by protocol 15041D as approved by the IACUC committee of New Jersey Medical School. Animal studies were compliant with all applicable provisions established by the Animal Welfare Act and the Public Health Services (PHS) Policy on the Humane Care and Use of Laboratory Animals.

*C. neoformans* Strains and Growth Conditions

*C. neoformans* var. *grubii* (serotype A) H99 and its isogenic mutant fbp1Δ deletion mutants were generated as described in the above Examples. Strains were grown at 30° C. on yeast extract-peptone-dextrose (YPD) agar medium overnight and the next day were washed with PBS three times before inoculum preparation.

Capsule Production and GXM Purification

To examine capsule production, 5 μL of overnight cultures were inoculated on minimum medium (MM) and incubated at 30° C. for three days. Capsule was visualized with India ink negative staining and observed with a 100× Olympus CX41 equipped with an Infinity digital camera (Olympus, N.J.). Secreted total polysaccharides was purified from 500 mL YPD culture of each strain using the CTAB precipitation method. The amount of the total GXM was determined by the phenol sulfuric method. Purified GXM was sent to the Comprehensive Carbohydrate Research Center at the University of Georgia for 1 dimensional proton nuclear magnetic resonance (NMR) spectroscope analysis. The two-pair T-test method was used to determine the statistical significance of the difference between samples.

Measurement of Cell Surface Mannoprotein, Chitin and Chitosan Levels

Mannoprotein staining proceeded according to the following. Briefly, fungal cells were grown on YPD overnight, re-suspended in PBS supplemented with 0.5% gelatin at a final OD60 of 0.5 for 30 min. On hundred microliter of each suspension was co-incubated with 10 uL of ConA-FITC (Sigma, 2.5 mg/ml stock) for 30 min at room temperature. The extent of ConA-FITC binding was determined using flow cytometry.

Infections, CCR2$^+$ Depletion, and Vaccinations

All infections were performed by intranasal inoculation. Mice were anesthetized with 100 μL of Ketamine (12.5 mg/mL) and Xylazine (1 mg/mL) prior to inoculum instillation into the nostrils. Varying inoculum doses ranging from $1\times10^4$ to $1\times10^6$ of H99 and fbp1Δ deletion mutants were used in the study. For survival experiments, mice were monitored daily for the development of disease symptoms and euthanized according to IACUC guidelines. For analysis of parameters of host immunity, lungs, bronchoalveolar lavage fluid (BALF) and mediastinal lymph nodes (MLNs) were harvested and processed as previously described. The effective depletion of CCR2$^+$ cells was achieved by intraperitoneal administration of diphtheria toxin. For vaccination experiments, fbp1Δ deletion mutants were heat-killed by incubation at 75° C. for 40 minutes. The inoculum was prepared at a concentration of $1\times10^8$ cells per 50 μL. Mice were immunized and boosted at days −31 and −7 days prior to infection. At day 0, mice were challenged intranasally with 1×10$^4$ live H99 per mouse.

Histology

For histological examination, lungs were perfused with 10 ml of PBS to remove blood and fixed in 10% buffered formalin. Fixed lung tissue was paraffin embedded and stained by H&E at the Histology Core Facility (Rutgers-NJMS).

Lung Processing

Single cell suspensions from lung tissue lung samples were minced in PBS with 3 mg/ml collagenase type IV (Worthington), and were incubated at 37° C. for 45 min. After digestion, lung suspensions underwent RBC lysis. Total lung cells were counted for each sample. Lung cell suspensions were used for RNA extraction and flow cytometry as described herein, as well as for CFU determination by plating serial dilutions.

T-Cell Responses in Airways

Bronchoalveolar lavage fluid (BALF) was harvested in PBS and plated in a 96-well round-bottom plate in RPMI containing 10% fetal calf serum (FCS), Penicillin-Streptomycin (2200 U/ml, Gibco™) and Gentamicin sulfate solution (1 mg/mL). BALF cells were re-stimulated using Leukocyte Activation Cocktail, with BD GolgiPlug™ (BD Biosciences) according to the manufacturer's instructions. Six hours after activation, BALF cells were surface stained and fixed in 1% paraformaldehyde overnight, then intracellular strained, and finally analyzed by flow cytometry as described herein.

T-Cell Assays from MLNs

Total lymphocyte suspension was prepared from the MLNs by utilizing the frosted ends of a glass slide and counted. Cells from the same experimental group were pooled, and CD4$^+$ T-cells were isolated with a negative-sorting CD4$^+$ isolation kit (Miltenyi Biotec, Auburn, Calif.) according to the manufacturer's instructions and were consistently >90% pure. CD4$^+$ T-cells (2×10$^5$) were cultured with T-cell-depleted APCs (3×105) in RPMI containing 10% fetal calf serum (FCS), Penicillin-Streptomycin (2200 U/ml, Gibco™) and Gentamicin sulfate solution (1 mg/mL), plated in flat-bottom 96-well plates and incubated at 37° C. with 5% $CO_2$. To prepare APCs, splenocyte suspension of a naive syngeneic mouse was prepared similarly to MLNs, and then depleted of T-cells by incubation with an anti-Thy1.2 antibody and rabbit complement (Low Tox; Cedarlane Labs, Hornby, Ontario, Canada) at 37° C. for 45 min. For antigen stimulation, live or sonicated H99 were added in a MOI of 1:1.5 (APC:yeast). All cultures were made in presence of the fungal growth inhibitor voriconazole at a final concentration of 0.5 mg/mL. After 72 h post-culture initiation, supernatants were collected for cytokine analysis by ELISA. For IL-2 and TNF-α, ELISA kits from BD-OptEIATM were used, and for IFN-γ and IL-17A (homodimer), ELISA kits were purchased from eBioscience.

Flow Cytometry

Single cell suspensions were stained for monocytes [CD45 (30-F11 APC-Cy7), CD11b (M1/70 PerCP Cy5.5) and Ly6C (AL-21 PE)], Mo-DCs [CD45 (30-F11 APC-Cy7), CD11b (M1/70 PerCP Cy5.5), Ly6C (AL-21 PE), CD11c (N418 Pacific Blue) and MHC Class II I-A/I-E (M5/11.415.2 Alexa Fluor 700)], neutrophils [CD45 (30-F11 APC-Cy7), CD11b (M1/70 PerCP Cy5.5), Ly6C (AL-21 PE) and Ly6G (1A8 APC)], CD4$^+$ T-cells [CD45 (30-F11 APC-Cy7), CD4 (RM4-5 Pacific Blue)], CD8$^+$ T-cells [CD45 (30-F11 APC-Cy7), CD8α (53-6.7 FITC), B cells [CD45 (30-F11 APC-Cy7) and B220 (RA3-6B2 APC-Cy7)]. All antibodies used for lung staining and MLNs were from BD Biosciences. BALFs were cell surface stained for T-cells with Thy1.2 (53-2.1 PE-Cy7) and CD4 (RM4-5 Pacific Blue) and ICCS for IFN-γ (XMG1.2 PE), IL-17A (eBio17B7 APC), IL-13 (eBio13A AlexaFlour 488) and TNF-α (MP6-XT22 Alexa Flour 700) following standard procedures. Most antibodies and reagents for cell surface and ICCS were from BD Biosciences, except for IL-17A that were obtained from eBioscience, Inc. All samples were analyzed using a BD LSRII Flow Cytometer and FlowJo software (Tree Star, Inc).

RNA Extraction and qRT-PCR

Total RNA from lungs was extracted with Trizol (Invitrogen). Relative mRNA levels were determined by qRT-PCR. One microgram of total RNA was reverse transcribed using High Capacity cDNA Reverse Transcription Kit (Applied Biosystems). Taq Man Fast Universal PCR Master Mix (2×) No Amp and TaqMan probes (Applied Biosystems) for each gene were used and normalized to GAPDH. Gene expression was calculated using ΔΔCt method relative to naïve sample.

Results

Deletion of Fbp1 Does Not Affect the Expression of Known Virulence Factors in *C. neoformans*

Figure 2:
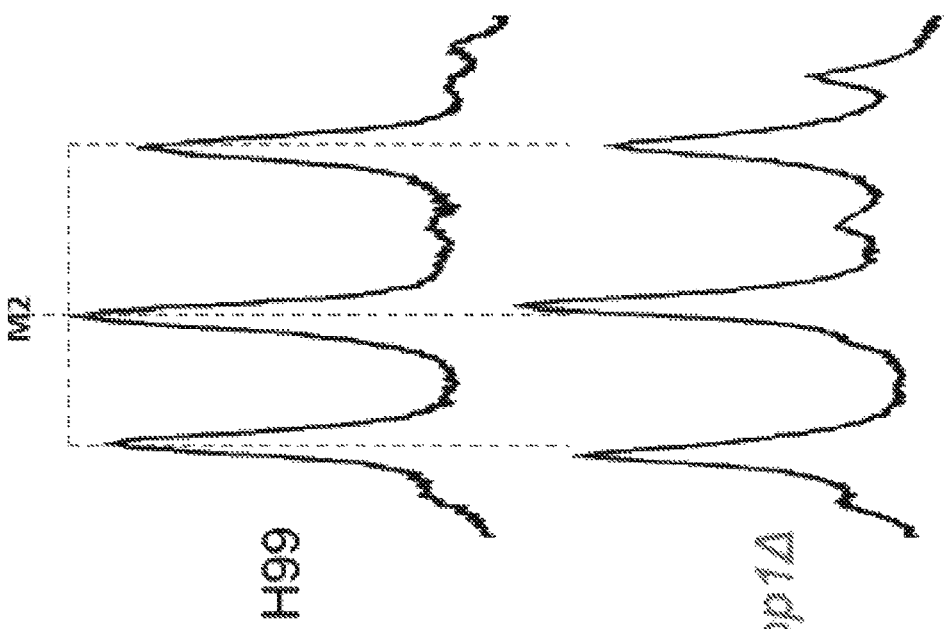
FIGS. 2A through 2D represents that the deletion of Fbp1 does not affect the expression of known virulence factors in *C. neoformans*.
Figure 2:
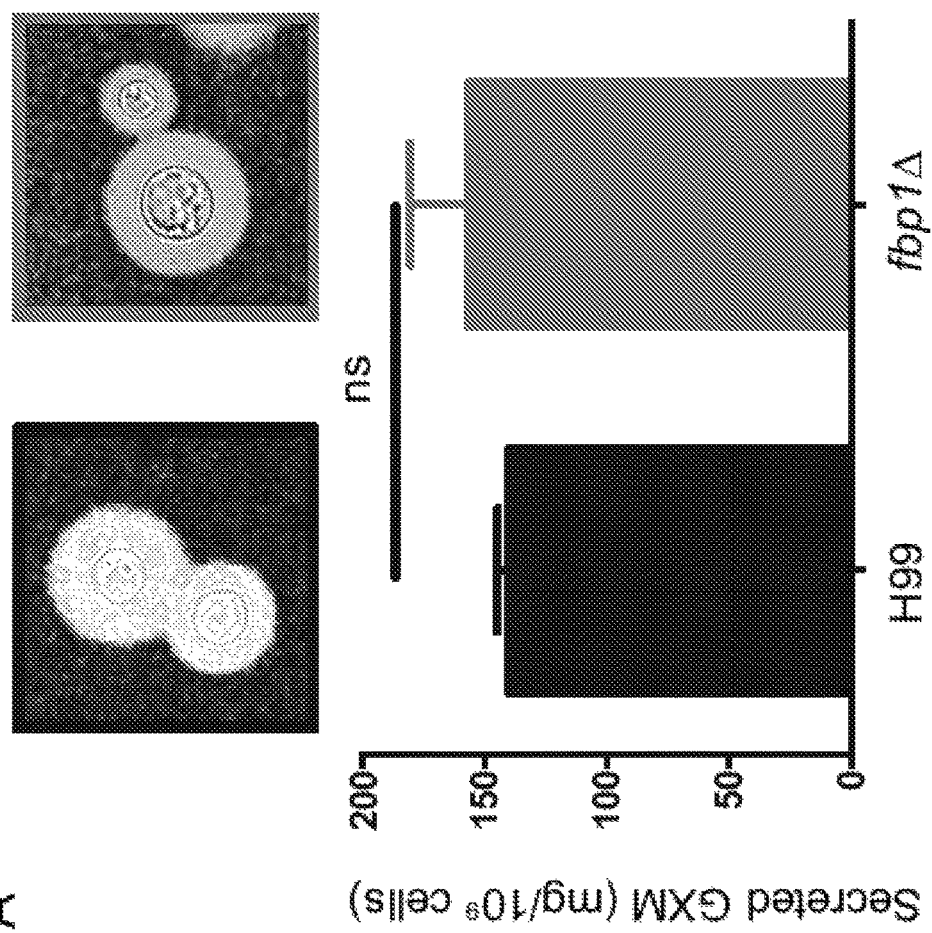
Figure 2:
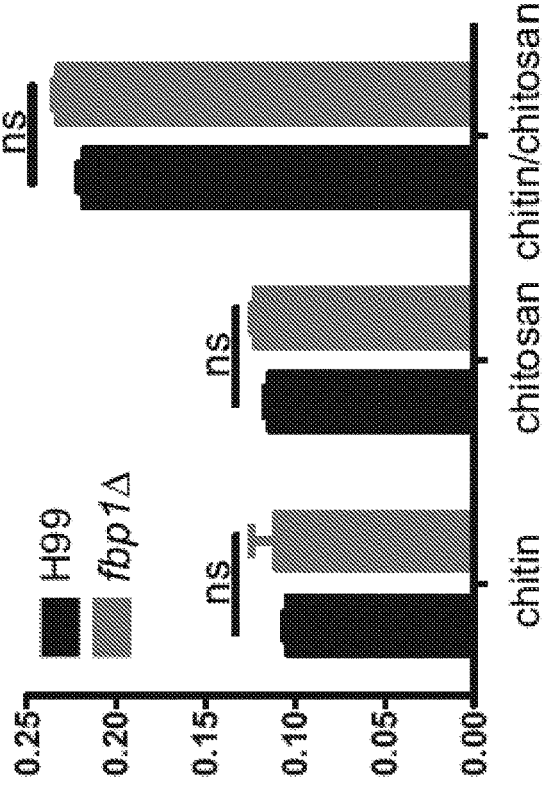
Figure 2:
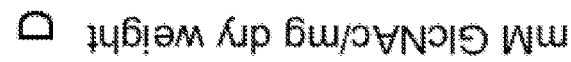
Figure 2:
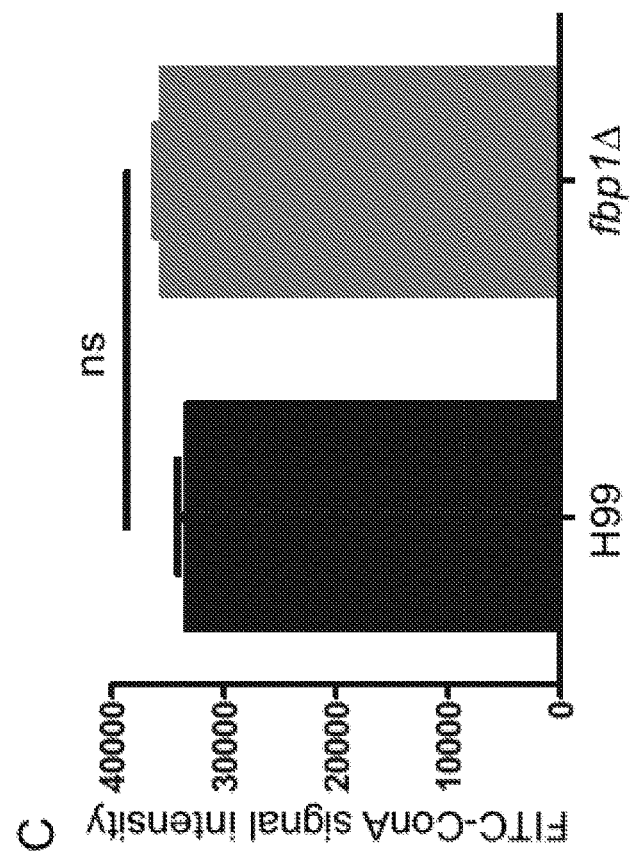

Examples 1 and 2 supra illustrate that deletion of Fbp1 in the H99 strain of *C. neoformans* resulted in virulence attenuation in vivo without affecting the production of the primary virulence factors, such as melanin, capsule and thermotolerance in vitro. To further examine potential effects on known virulence factors a detailed characterization was performed on the secretion of the primary capsule polysaccharide, glucuronoxylomannan (GXM), by fbp1Δ deletion mutants as compared to the parental strain and determined that both strains secreted comparable amounts (FIG. 2A). The capsule composition was also tested in detail and no differences in size or structure (FIG. 2B) were found. Similarly, there was no observation of any differences in the amount of surface mannoproteins expressed by fbp1Δ deletion mutants based on the ConA-FITC binding intensity (FIG. 2C). Recent studies have suggested that changes in the amount of chitin and chitosan impact the virulence of *C. neoformans*. Accordingly, it was also tested whether expression of these carbohydrates was affected in the fbp1Δ strain. It was found that there were no significant differences in the amount of chitin or chitosan expressed by fbp1Δ as compared to H99 (FIG. 2D). Altogether, these results, together with the findings in Examples 1 and 2, suggest that the attenuated virulence in vivo upon infection with fbp1Δ cannot be explained by measurable changes in the production of known virulence factors. Therefore, it was examined whether infection with fbp1Δ impacts the development of host immunity as compared to the parental strain H99 and to define host factors that might confer protection from infection with fbp1Δ.

Infection with fbp1Δ Induces a Robust Inflammatory Response in the Host.

Figure 3:
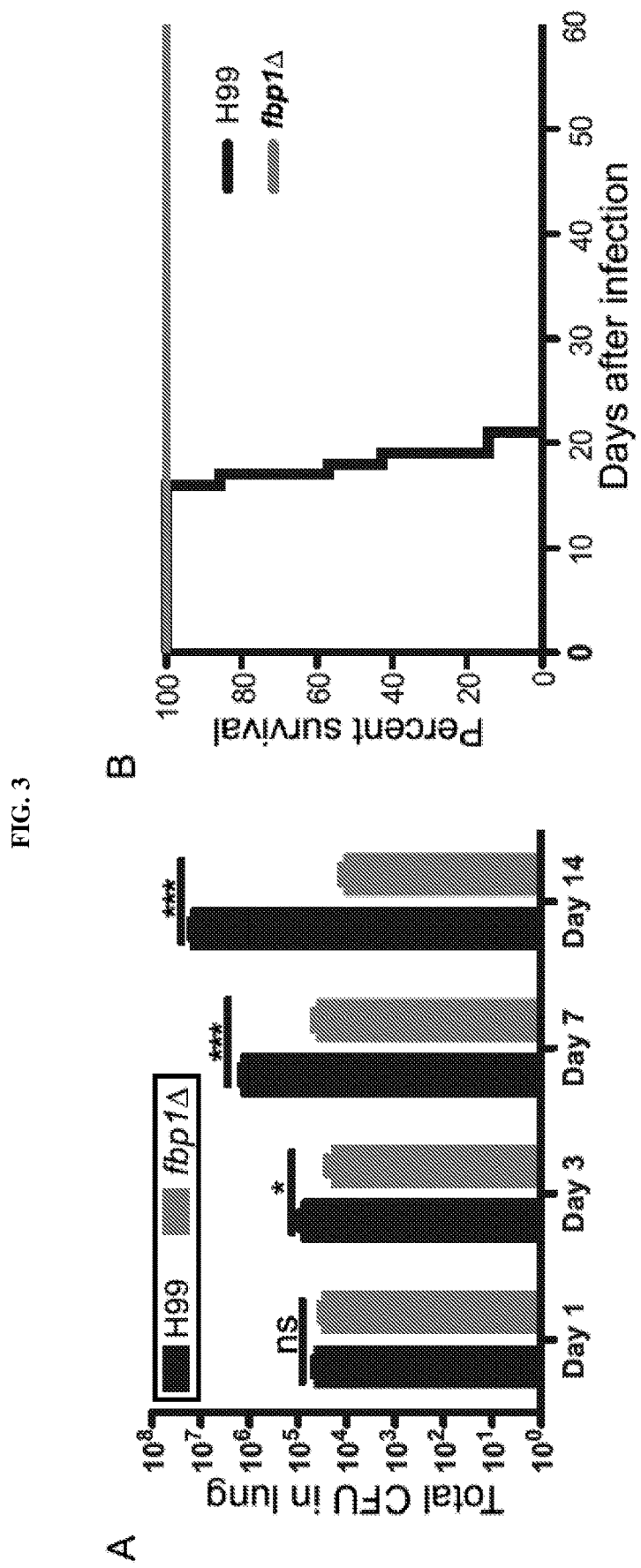
FIGS. 3A through 3H represent mice infected with fbp1Δ display enhanced inflammatory responses and survival. C57Bl/6J mice were infected intranasally (i.n) with $10^5$ H99 or $10^6$ fbp1Δ.
Figure 3:
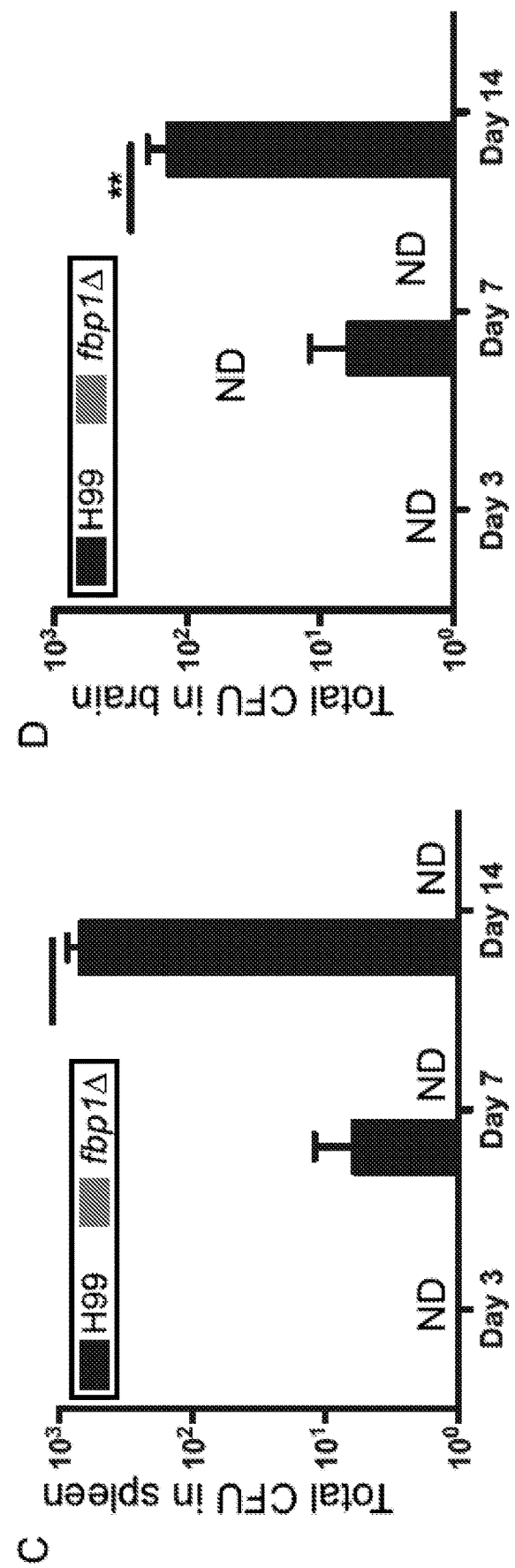
Figure 3:
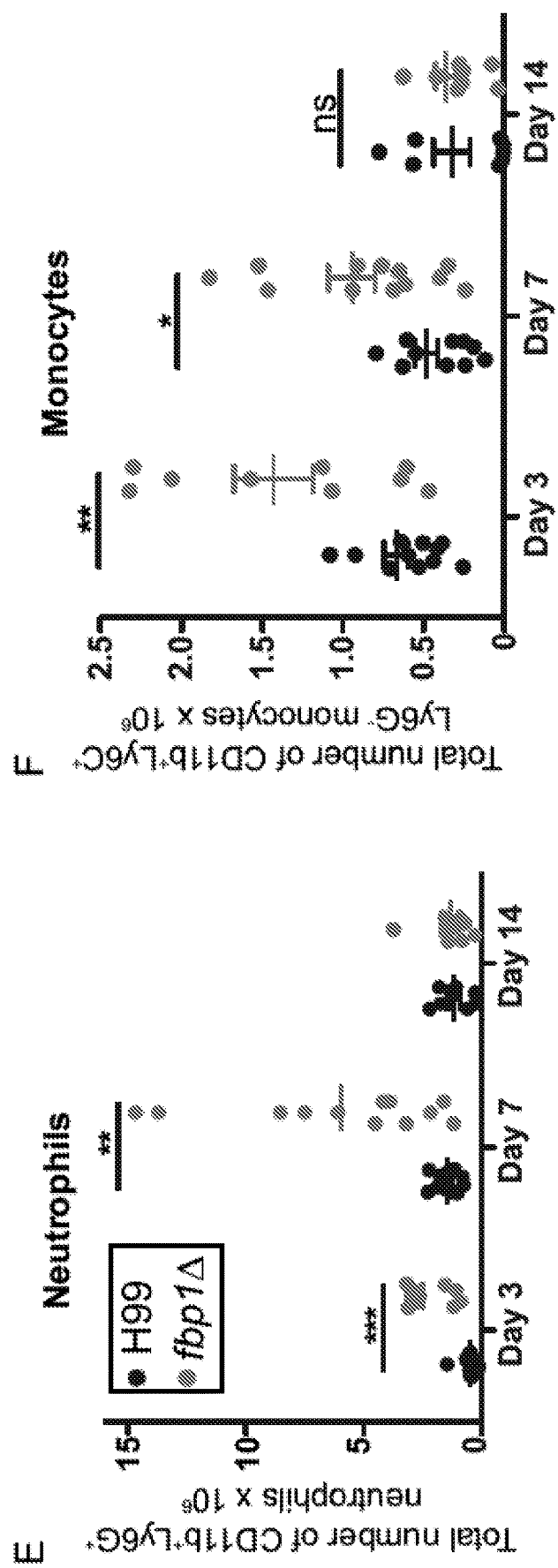
Figure 3:
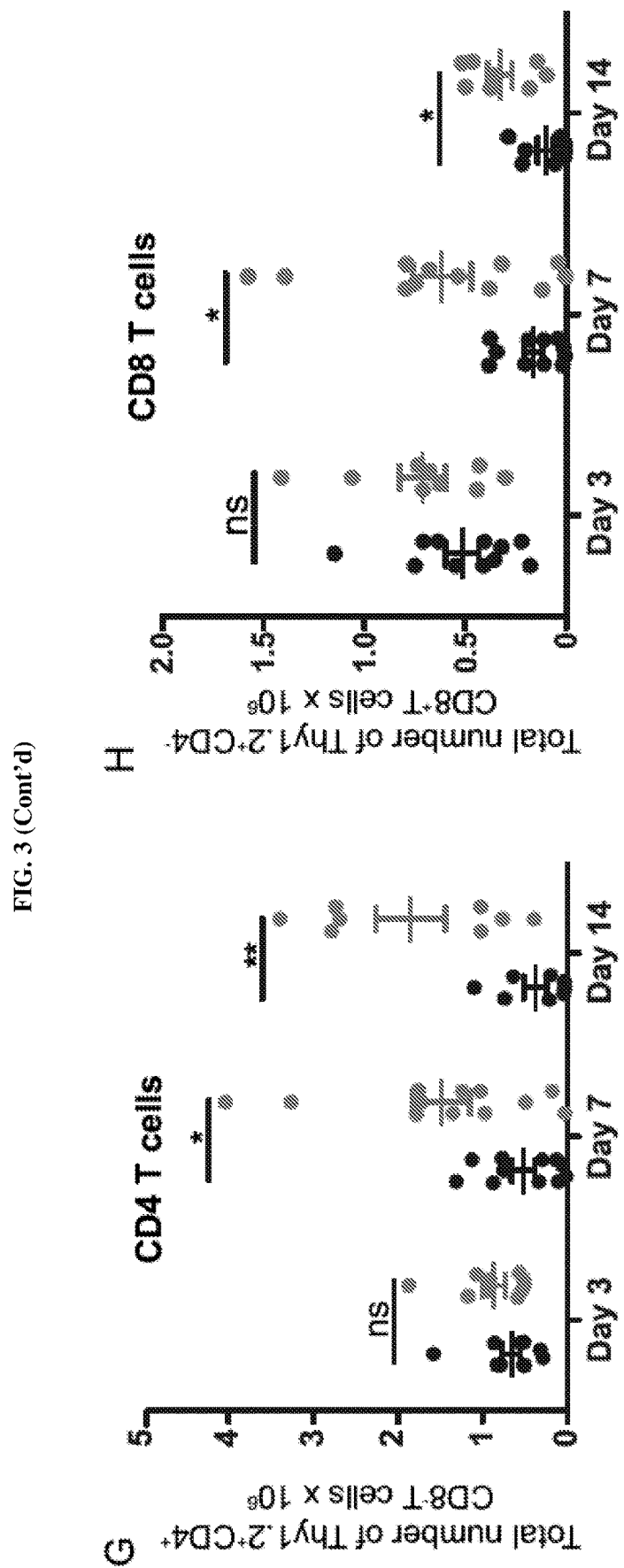
Figure 4:
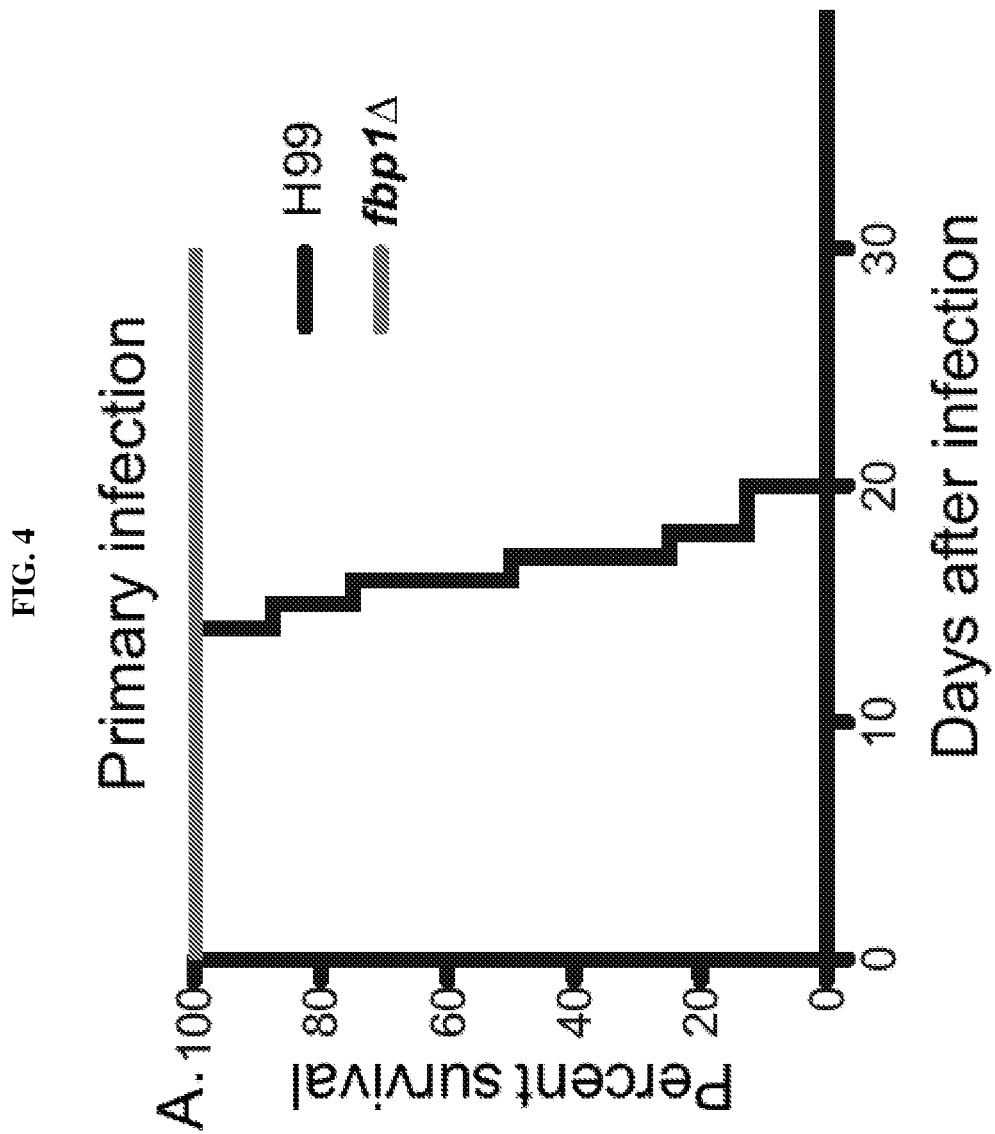
FIGS. 4A through 4G represent additional data regarding survival patterns and $CD4^+$ T-cell responses.
Figure 4:
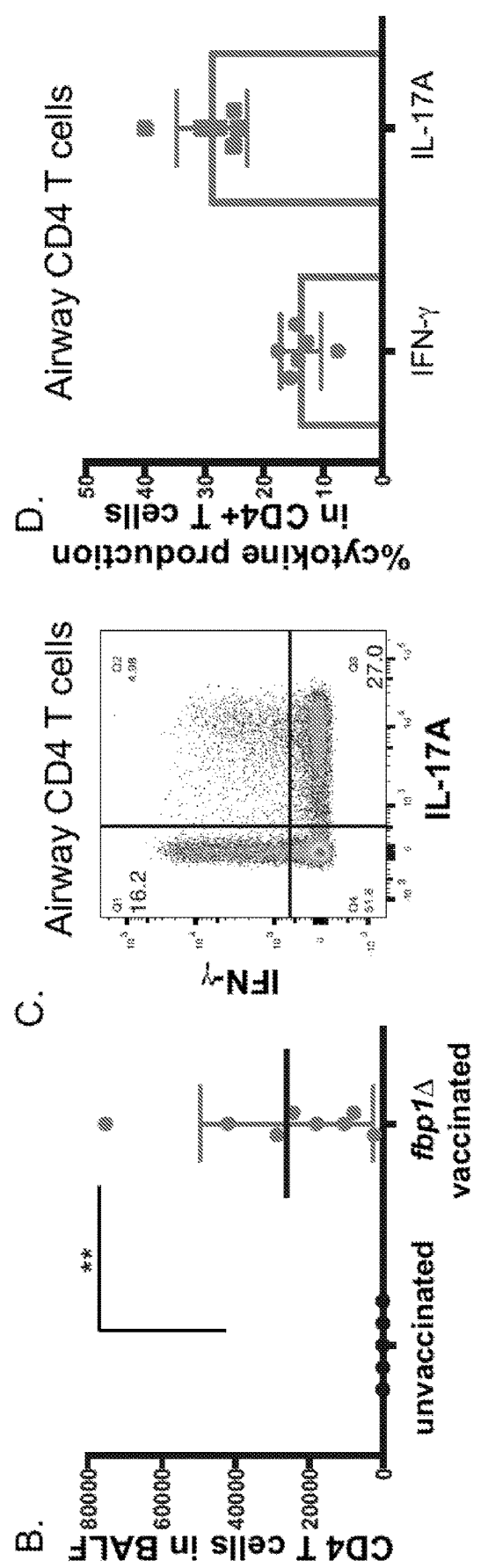
Figure 4:
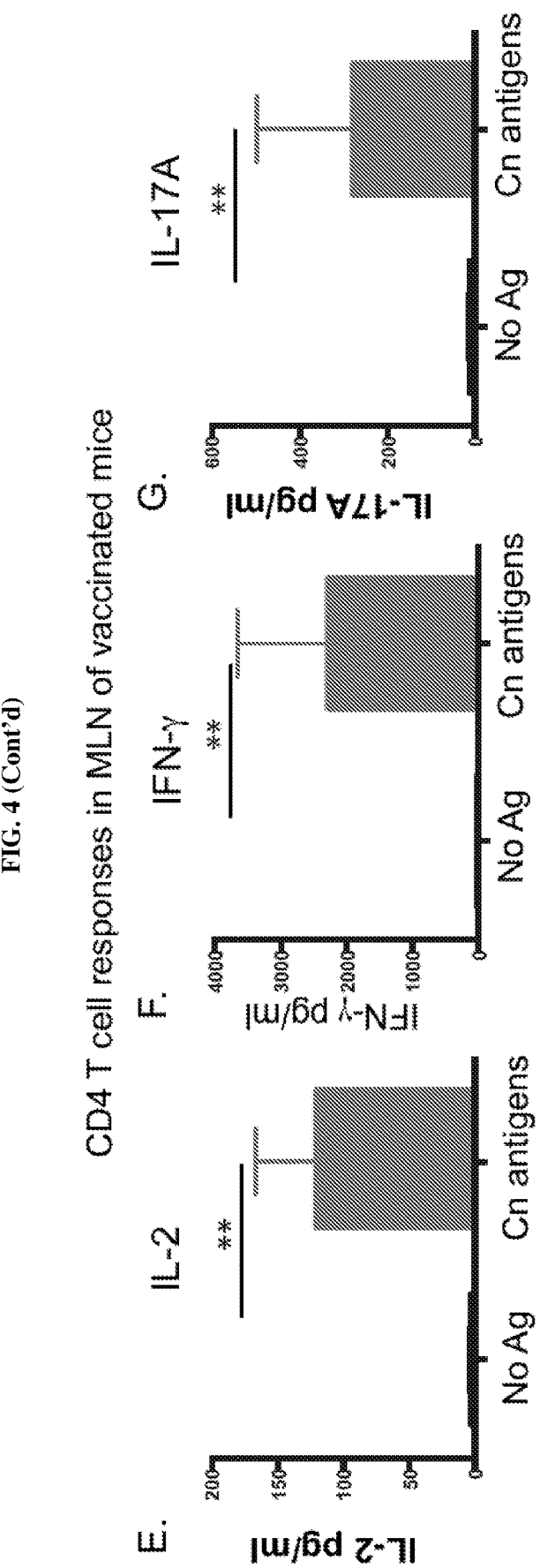

In the previous Examples, an infection dose of 10$^5$ H99 and 10$^5$ fbp1Δ in mice of the A/J background was used and it was found that these mice survived an infection with fbp1Δ for over 60 days. Although the initial inoculum was the same, H99 grew several log higher than fbp1Δ and disseminated to the brain and spleen while fbp1Δ remained in the lung. This Example sets out to determine whether increasing the infection dose of fbp1Δ would overcome this attenuated phenotype. It additionally examines whether attenuation of fbp1Δ was maintained in mice of a different genetic background, because while not wishing to be bound by theory, several previous studies reported substantial intrinsic differences among mouse strains in terms of their susceptibility to cryptococcosis. Therefore, it was chosen to test mice in the C57Bl/6J (B6) background since this is a commonly studied strain for analyzes of host immunity and there are a significant number of immune gene-deficient mice in this background. Infection of B6 mice with $10^5$ H99 and $10^6$ fbp1Δ deletion mutants resulted in equal seeding of yeast cells in the lung at 24 hours after infection (FIG. 3A). All B6 mice infected with H99 succumbed to infection by 20 days after inoculation while fbp1Δ infected mice survived for over 50 days (FIG. 3B). A similar survival pattern was observed in A/J mice infected with $10^6$ fbp1Δ (FIG. 4A). Therefore, increasing the infection dose or changing the host genetic background did not overcome the attenuation of fbp1Δ. It was observed that the fungal burden of fbp1Δ yeast remained constant in the lung of infected mice during the observation period (FIG. 3A). In contrast, H99 continued to grow and by day 14 after infection the pulmonary fungal burden of H99 had increased to several log higher as compared to the initial number of yeast seeded in the lung at 24 hrs after inoculation (FIG. 3A). H99 was also able to quickly escape from the lung and viable CFU were recovered as early as day 7 after infection from the spleen and brain (FIG. 3C, 3D). In contrast, fbp1Δ deletion mutants remained in the lung and there was no detection of viable yeast in the spleen or brain of infected mice (FIG. 3A, 3C, 3D). Thus, virulent H99 was able to rapidly overcome the host and disseminates to extra pulmonary sites while fbp1Δ remained in the lung. Based on these observations it was hypothesized that changes in the host immune response were central to the pulmonary containment of fbp1Δ and the long-term survival of mice infected with fbp1Δ as compared to H99. Several previous studies have documented the critical importance of host immunity as determinants of outcomes from infection with *C. neoformans* mutants. As a first step, the recruitment of immune cells to the lung was examined by flow cytometric analysis. It was observed that infection with fbp1Δ induced a significant increase in the number of innate and adaptive immune cells that were recruited to the lung (FIG. 3E, 3F, 3G, 3H). Further observations included increased frequencies in the number of neutrophils and monocytes (FIG. 3E, 3F) as well as increased numbers of pulmonary $CD4^+$ and $CD8^+$ T-cells (FIG. 3G, 3H). In aggregate, these observations suggest that host immune cells are more robustly recruited to the lung of mice infected with yeast lacking Fbp1 as compared to the parental strain H99.

Mice Infected with fbp1Δ Display Enhanced Differentiation of Th1, Th17 and Th1/Th17 $CD4^+$ T-Cell Responses.

Given the importance of $CD4^+$ T-cells in defense against cryptococcosis, the differentiation of *Cryptococcus*-specific $CD4^+$ T-cells in mice infected with Fbp1-deficient or sufficient yeast was examined. The cytokine profile of $CD4^+$ T-cells recovered from the airways and lung-draining lymph node (MLN) of mice infected with fbp1Δ to H99 was compared. Peak $CD4^+$ T-cell responses were detected at day 7 after infection as measured by expansion in MLN (IL-2 production, FIG. 5A) and recruitment to the lung. Infection with H99 and fbp1Δ induced comparable $CD4^+$ T-cell activation in the MLN as examined by IL-2 production after ex vivo re-stimulation (FIG. 5A). It was observed that infection with fbp1Δ induced enhanced differentiation of IFN-γ secreting Th1 cells (FIG. 5B) and I1-17A-secreting-Th17 $CD4^+$ T-cells (FIG. 5C). Increased differentiation of Th1 and Th17 cells after fbp1Δ infection was accompanied with decreased differentiation of IL-4 (FIG. 5D), IL-5 (FIG. 5E) and IL-13 (FIG. 5F)-producing Th2 cells as compared to H99. This suggests that infection with fbp1Δ skews $CD4^+$ T-cell differentiation towards Th1 and Th17 responses and diminished Th2. At days 7 and 14 mice infected with fbp1Δ also displayed enhanced frequencies of IFN-g$^+$, IL17$^+$ and TNF$^+$ $CD4^+$ that infiltrated the airways as compared to mice infected with H99 (FIG. 5G, 5H, 5I, 5J). Increased frequencies of IFN-γ-producing $CD8^+$ T-cells were also present in the airways of fbp1Δ-infected mice (FIG. 5G, 5K). Collectively, these findings indicate that infection with fbp1Δ induces enhanced recruitment of innate and adaptive immune cells as well as increased induction of Th1 and Th17 responses and lower Th2 $CD4^+$ T-cell responses. Previous studies have shown that Th2 responses against *C. neoformans* are detrimental while increased Th1 responses are protective. Therefore, the long-term survival observed in fbp1Δ-infected mice might be explained at least in part by enhanced induction of protective host immune responses that help contain fbp1Δ.

Lymphocytes are Required to Maintain the Long-Term Survival of Mice Infected with *C. neoformans* fbp1Δ.

Figure 5:
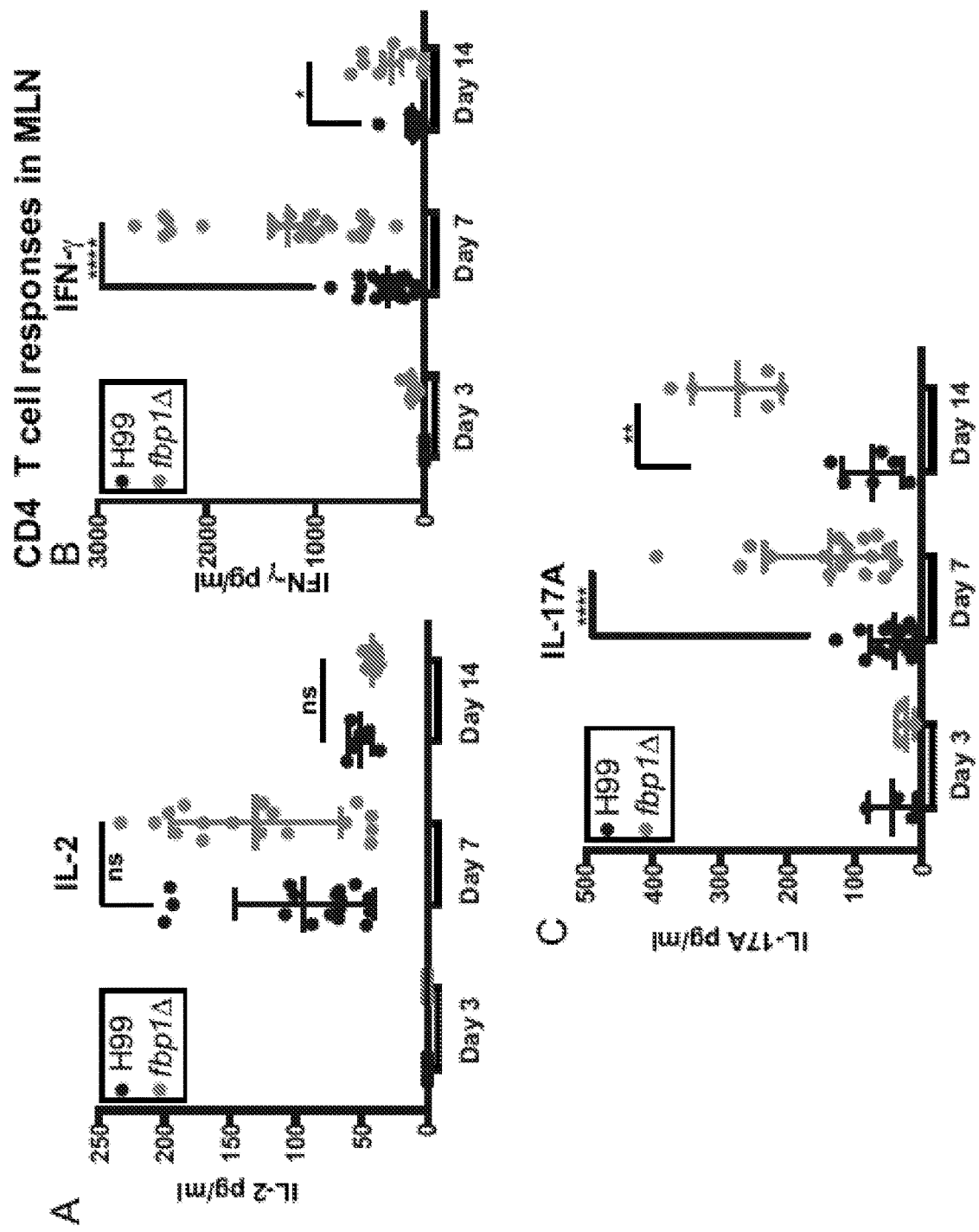
FIGS. 5A through 5K represent enhanced Th1 and Th17 $CD4^+$ T-cells responses in mice infected with fbp1Δ.
Figure 5:
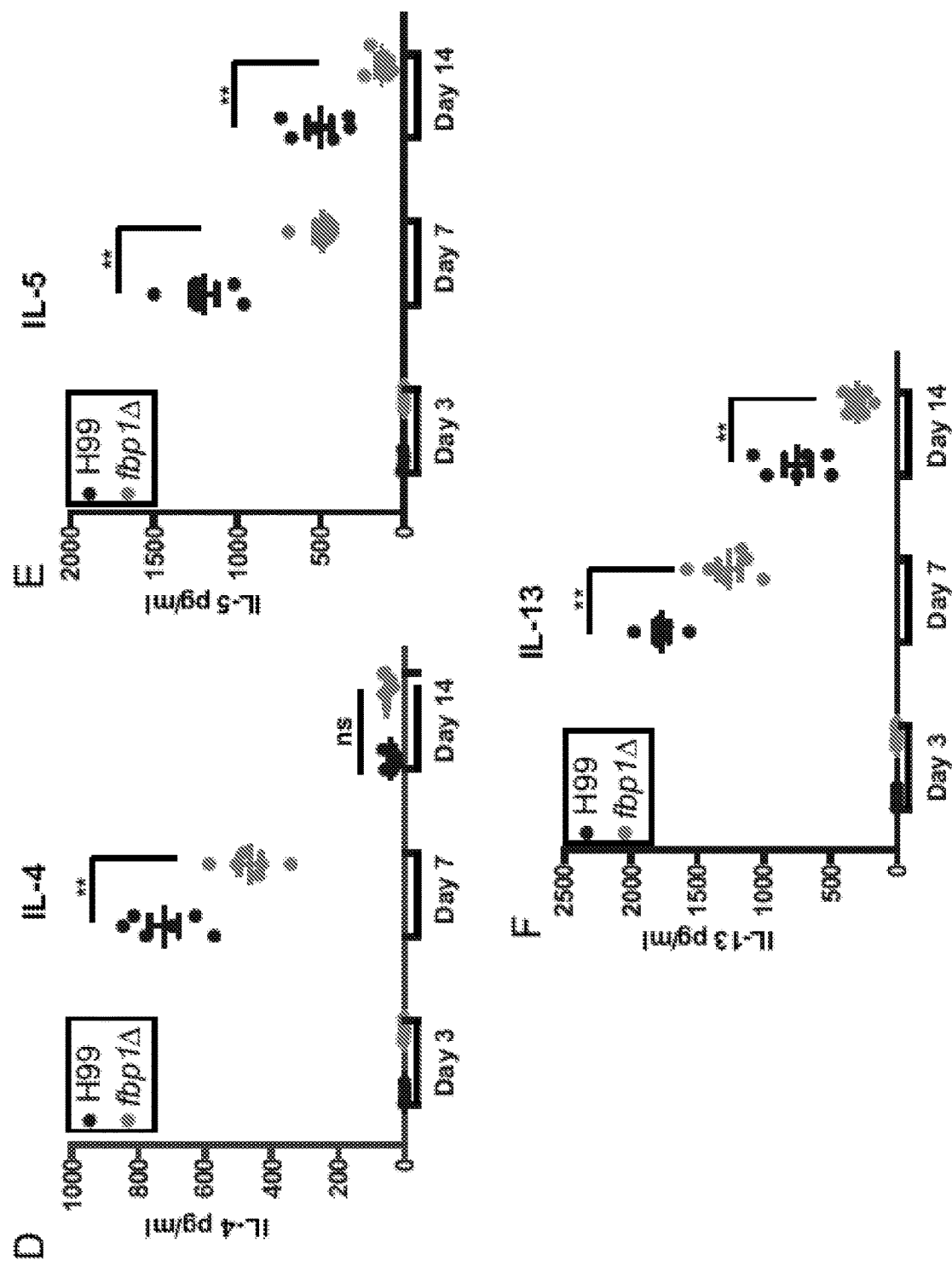
Figure 5:
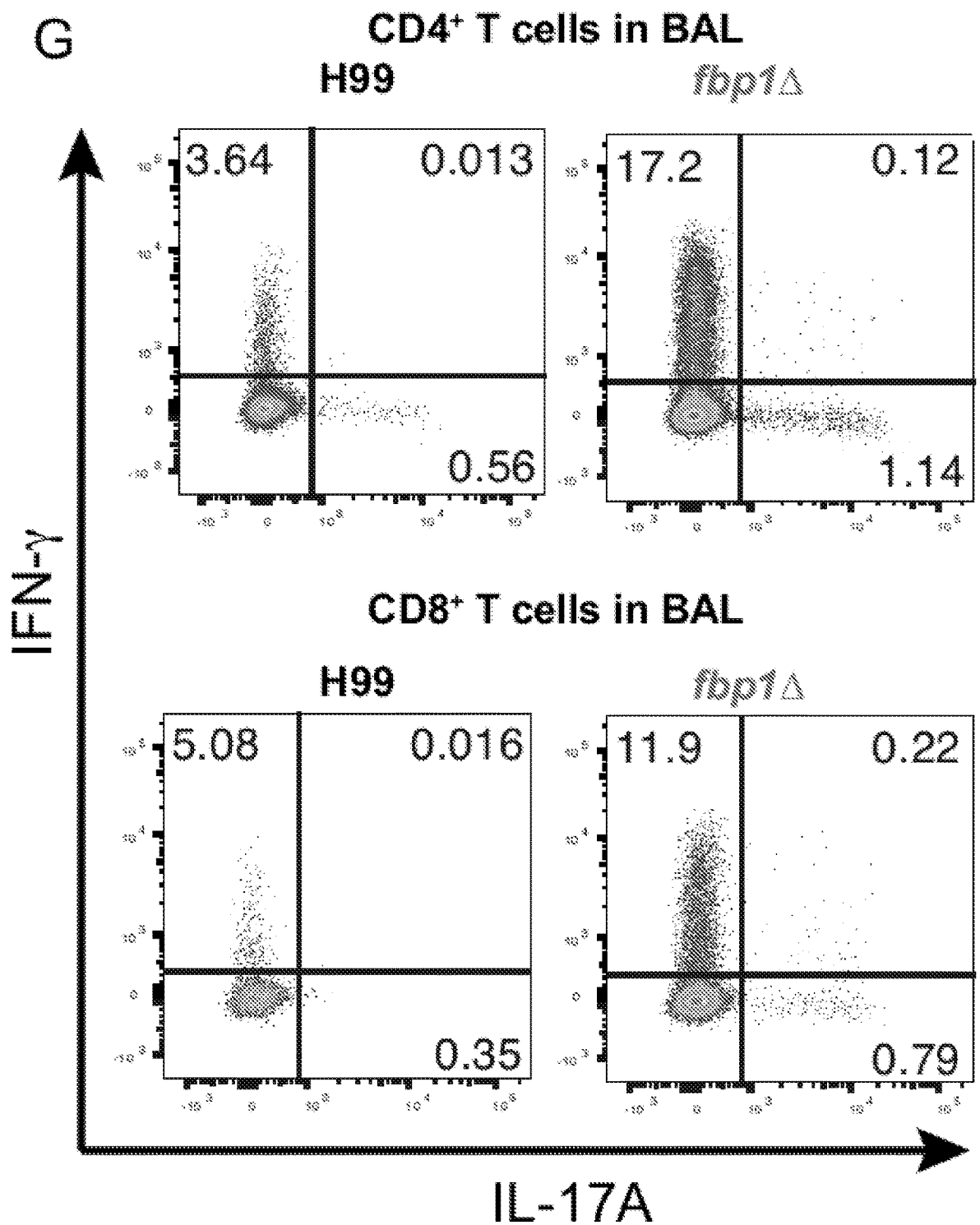
Figure 5:
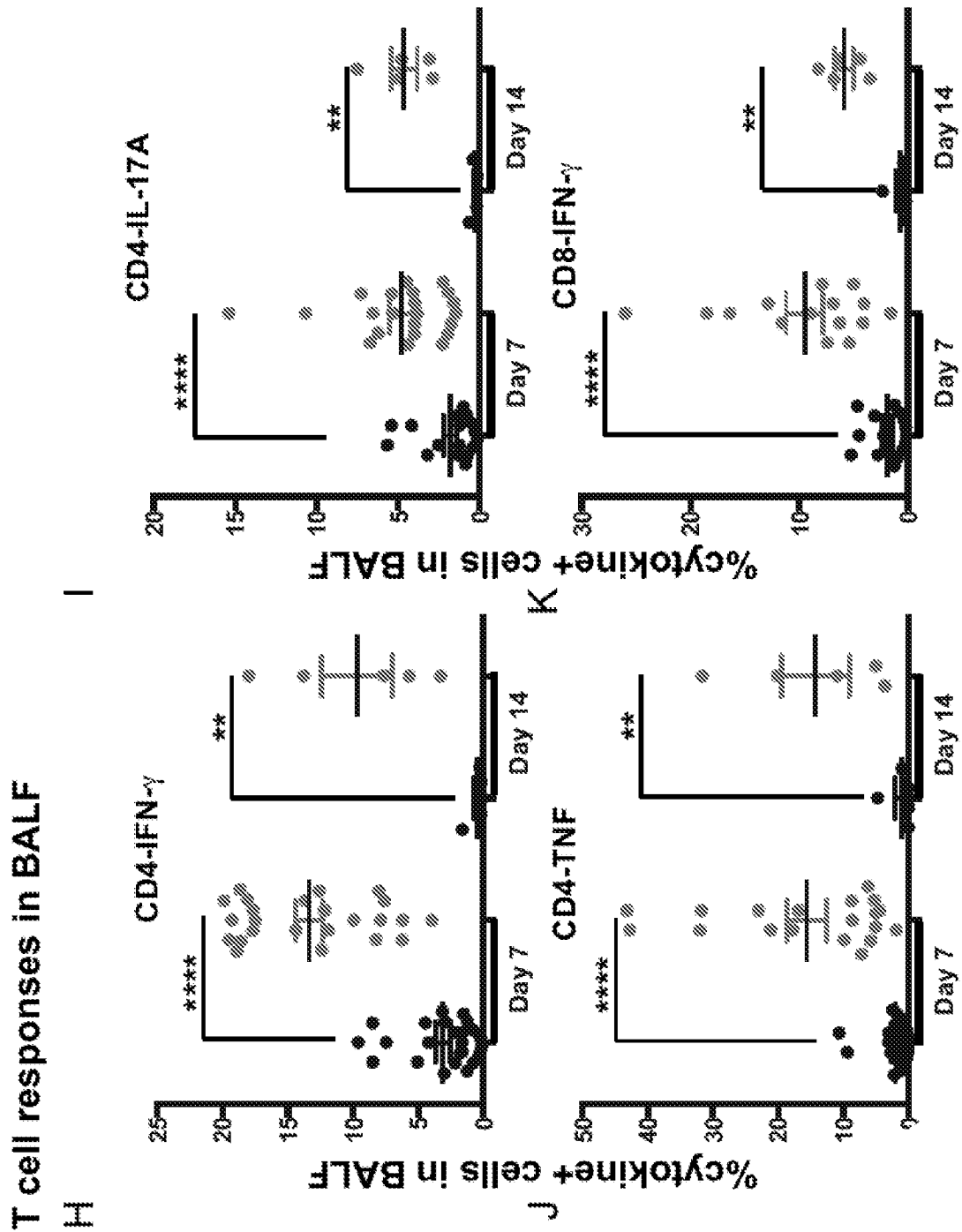
Figure 6:
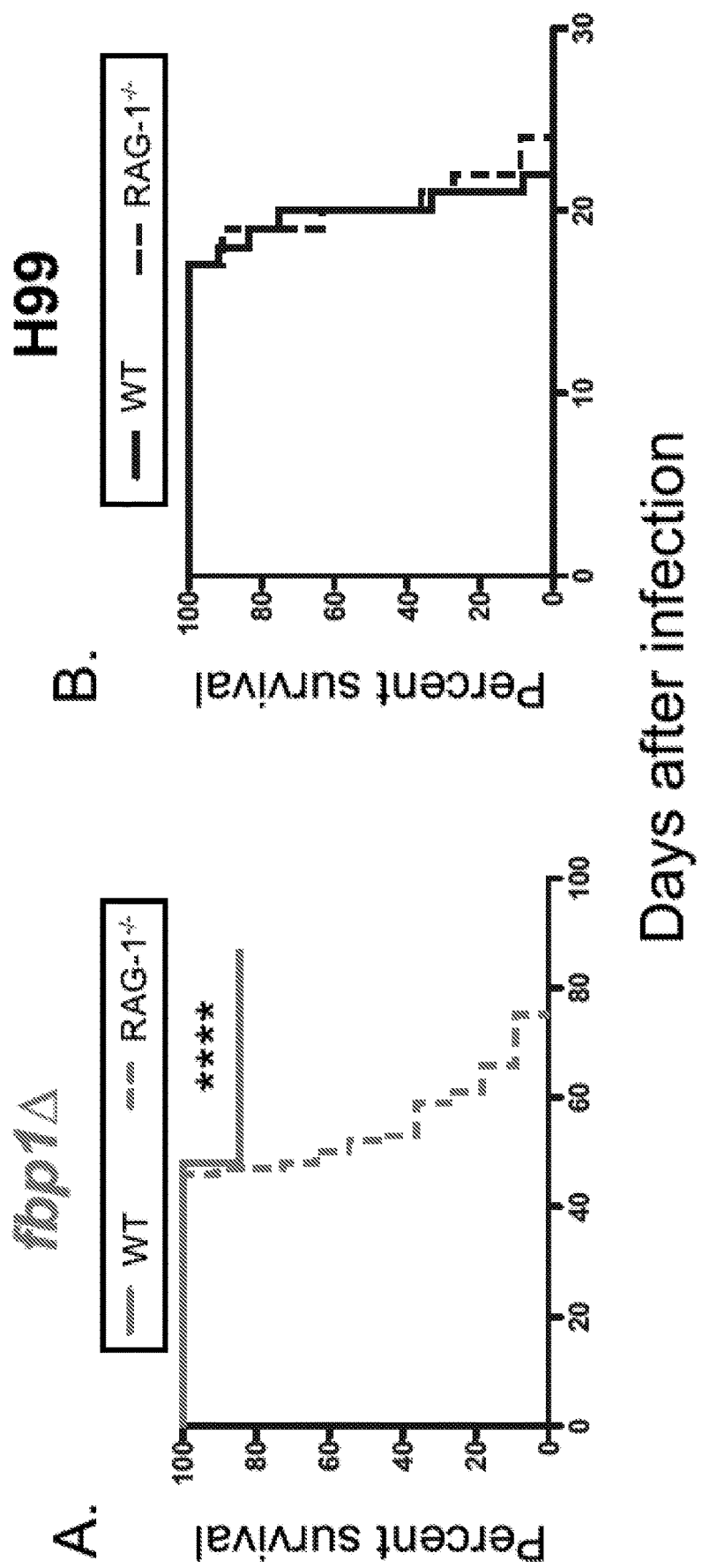
FIG. 6A through 6E represent that lymphocytes are required for long-term protection against infection with fbp1Δ. Lymphocyte deficient mice ($RAG^{-/-}$ dashed lines) and control mice (solid lines) were infected (i.n.) with $10^5$ H99 or $10^6$ fbp1Δ. Survival data shown is cumulative of two independent experiments with 5-7 mice per group.
Figure 6:
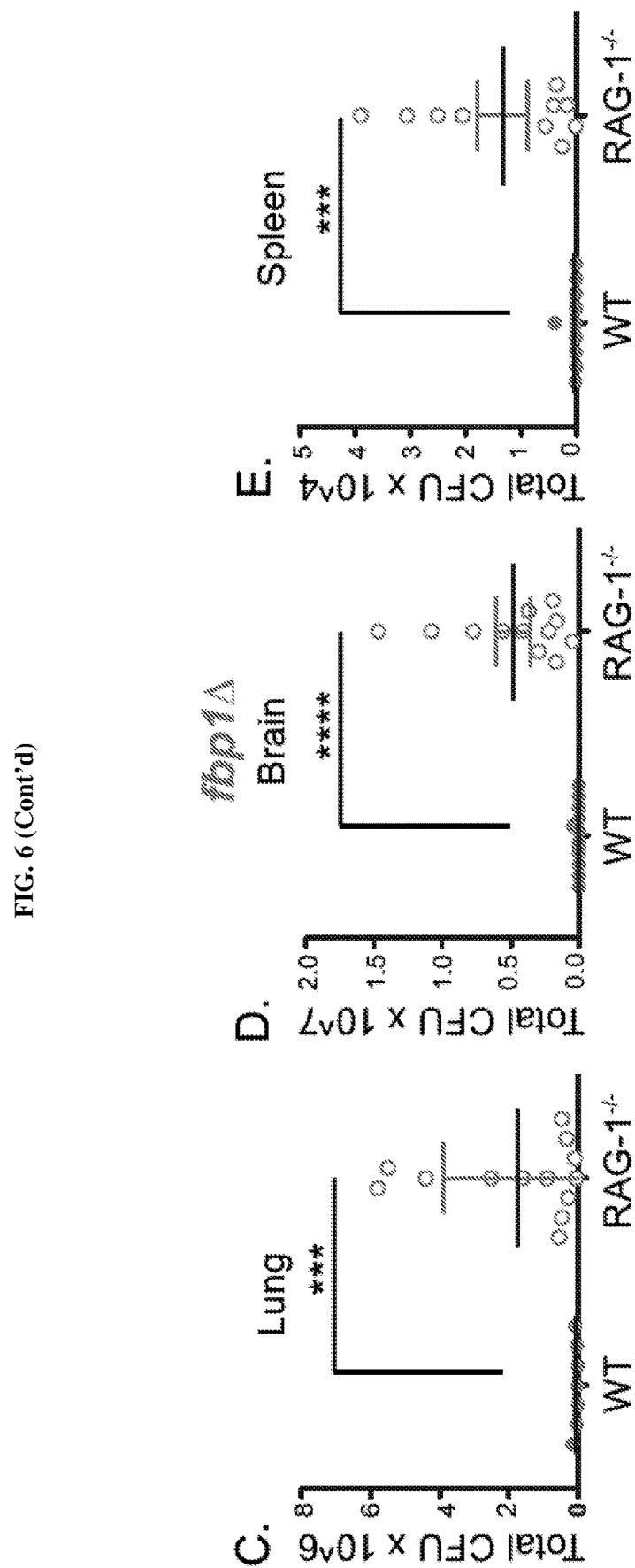

The results indicate infection with fbp1Δ deletion mutants induces an enhanced activation of immune responses including increased differentiation of Th1 and Th17 cells as well as increased production of IFN-γ by $CD8^+$ T-cells (FIG. 5). Therefore, while not wishing to be bound by theory, enhanced adaptive immunity against infection with fbp1Δ deletion mutants might be an important protective component of the host response. In order to test the importance of lymphocytes in this response RAG-1$^{-/-}$ mice that lack mature B and T-cells were infected with fbp1Δ and the parental H99 strain. Remarkably, 100% of mice lacking lymphocytes succumbed to infection with fbp1Δ while 85% of normal control mice survived the infection for over 76 days after infection (FIG. 6A). In contrast, mice infected with the parental H99 strain died within 21 days after infection whether they had an intact lymphoid compartment or not (FIG. 6B). Analysis of fungal burden in fbp1Δ-infected RAG-/- mice at the time of euthanasia showed increased fungal burden in the lung as well as dissemination of fbp1Δ yeast cells to the spleen and brain (FIG. 6C, 6D, 6E). Altogether these findings indicate that an intact lymphoid compartment is required for the protection and long-term survival of mice infected with fbp1Δ.

Enhanced Recruitment and Maturation of CCR2$^+$Ly6C$^+$ Monocytes in Mice Infected with fbp1Δ Mutants Although 100% of fbp1-infected RAG-/- succumbed to infection there was a delay in mortally of 30 days in average as compared to H99 infected mice (FIG. 6A, 6B). This observation suggested that immune cells, other than lymphocytes, can also help contain infection with fbp1Δ. The analysis of immune cell infiltration to the lung of fbp1Δ-infected mice showed significant increases in the number of recruited monocytes (FIG. 3F). Previous studies observed that that CCR2$^+$Ly6C$^+$ monocytes are important precursors of mo-DCs that orchestrate the development of Th1 $CD4^+$ T-cell responses to pulmonary fungal infection. Moreover, CCR2$^+$ monocytes have been previously shown to be important innate cells that contribute to defense against infection with *C. neoformans*. In addition, studies in pulmonary *B. dermatitidis* infection have demonstrated that inhibition of CCR2$^+$Ly6C$^+$ influx is a mechanism of virulence employed by other fungi. Importantly, blockade of CCR2$^+$Ly6C$^+$ influx by *B. dermatitidis* results in impaired immunity while robust recruitment correlates with induction of protective immunity. It was thus hypothesized that the Fbp1-regulated mechanism of virulence in *C. neoformans* might similarly affect the recruitment of Ly6C$^+$ monocytes. To test this hypothesis the differentiation of monocytes into mo-DCs was examined at day 3 after *C. neoformans* infection with H99 or fbp1Δ. Infection with Fbp1-deficient yeast resulted in significantly increased influx of monocytes (FIG. 3F) as well as their maturation into $CD11c^+ClassII^+$ mo-DCs (FIG. 7A, 7B, 7C) as examined by percent CD11c+ClassII+ cells among monocytes (FIG. 7A, 7B) and by total number of mo-DCs recruited to the lung (FIG. 7C). Increased influx Ly6C+ monocytes in fbp1Δ-infected mice correlated with higher production of CCR2 ligands CCL2, CCL7 and CCL12 (FIG. 7D, 7E, 7F). These observations suggest that increased recruitment of $CCR2^+$ Ly6C+ monocytes and their differentiation into mo-DCs is a potentially important innate mechanism of protection in mice infected with fbp1Δ.

$CCR2^+$ Monocytes are Required for the Activation of *C. neoformans*-Specific $CD4^+$ T-Cells and for the Survival of fbp1Δ-Infected Mice In order to test the potential contributions of $CCR2^+$ monocytes and their derivative cells to host-mediated defense against infection with fbp1Δ the CCR2-depleter mouse strain was employed. This strain permits selective and temporal removal of $CCR2^+$ monocytes upon diphteria toxin (DT) administration. CCR2-depleter and control littermates were infected with fbp1Δ yeast and treated with DT as depicted in FIG. 8A. Removal of $CCR2^+$ monocytes resulted in rapid mortality of mice (FIG. 8B) as compared to control, monocyte-sufficient mice. In the absence of $CCR2^+$ monocytes and mo-DCs there was minimal recruitment of $CD4^+$ T-cells to the airways (FIG. 8C), and the few cells that infiltrated the airways failed to differentiate into IFN-γ or IL-17A producing cells (FIG. 8D). Depletion of $CCR2^+$ monocytes and their derivative cells also resulted in a failure to induce the activation of *Cryptococcus*-specific $CD4^+$ T-cells responses in the MLN. Removal of $CCR2^+$ monocytes and impaired $CD4^+$ T-cell responses were also accompanied by a failure to contain fungal growth in the lung (FIG. 8E). The expression of protective cytokines in the lung was also significantly diminished in fbp1Δ-infected mice that were depleted of $CCR2^+$ monocytes (FIG. 8F). Altogether, these observations suggest that $CCR2^+$ cells are important innate cells in the containment of infection with fbp1Δ and that in their absence fbp1Δ manifests as a virulent strain.

4. Vaccination with Inactivated (Heat-Killed) fbp1Δ Mutants Confers Protection from Infection with Virulent H99 Yeast.

Initial Vaccination Studies

Figure 9:
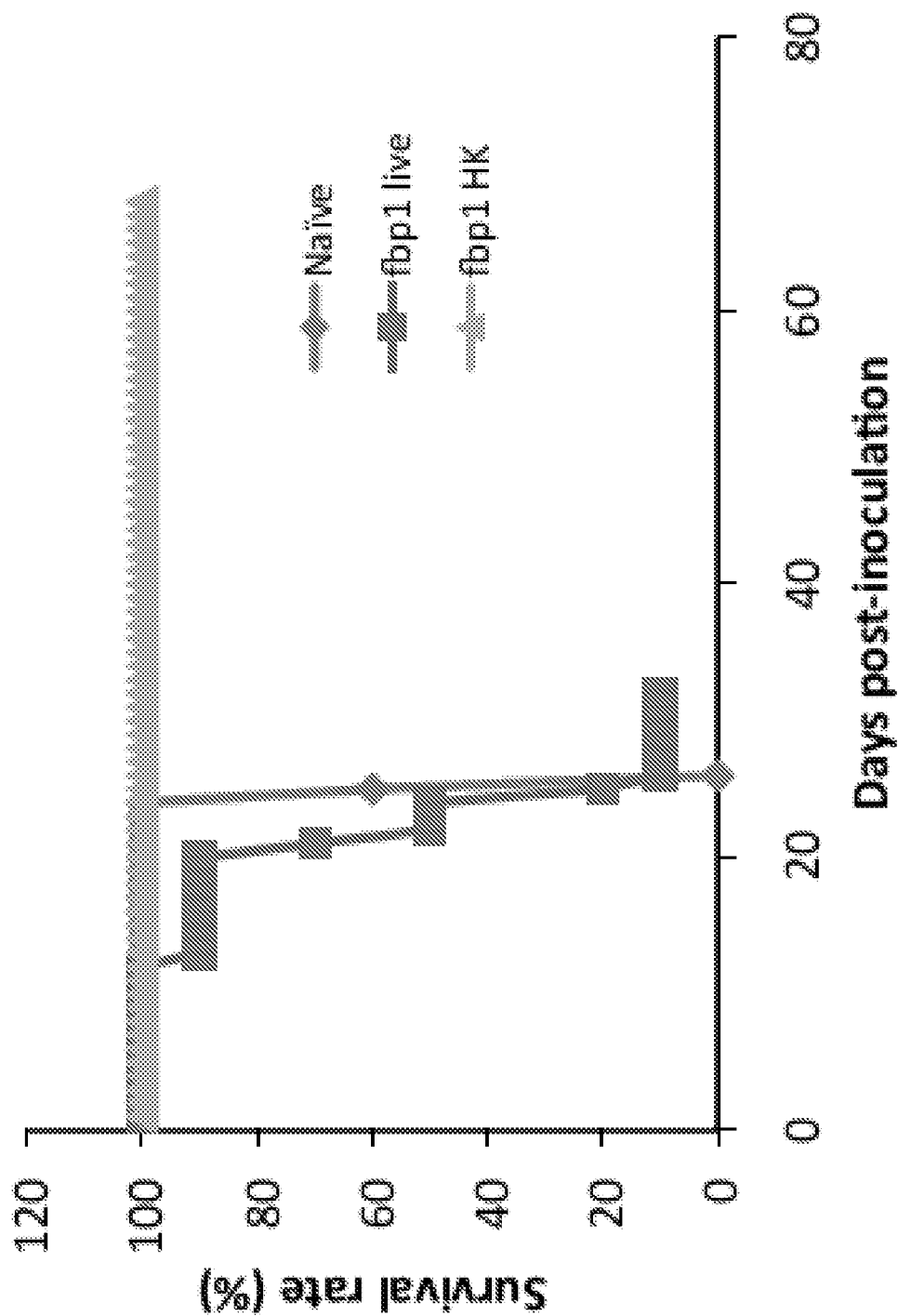
FIG. 9 represents that vaccination with inactivated (heat-killed) fbp1Δ mutants confers protection from infection with virulent H99 yeast. 25 A/Jcr mice were used; 5 were naïve control, 10 infected with live fbp1Δ deletion mutant ($10^6$ per mouse), and 10 infected with heat-killed fbp1Δ deletion mutant ($0.5×10^8$ per mouse). For the mice infected with heat-killed fbp1Δ deletion mutant, a booster inoculation was given after 24 days. After 30 days, mice from each group (naïve, fbp1Δ deletion mutant, and heat-killed fbp1Δ deletion mutant) were inoculated with H99 strain of C. neoformans ($10^6$ per mouse). Naïve mice succumbed to infection around 25 days post-infection with H99, as well as mice inoculated with live fbp1Δ deletion mutant. Mice inoculated with heat-killed fbp1Δ deletion mutant showed full immunity (100% effective) to virulent H99, as none of the mice succumbed to infection, even more than 60 days post infection by H99. Only the inactivated fbp1Δ deletion mutant was effective at providing immunity.
Figure 10:
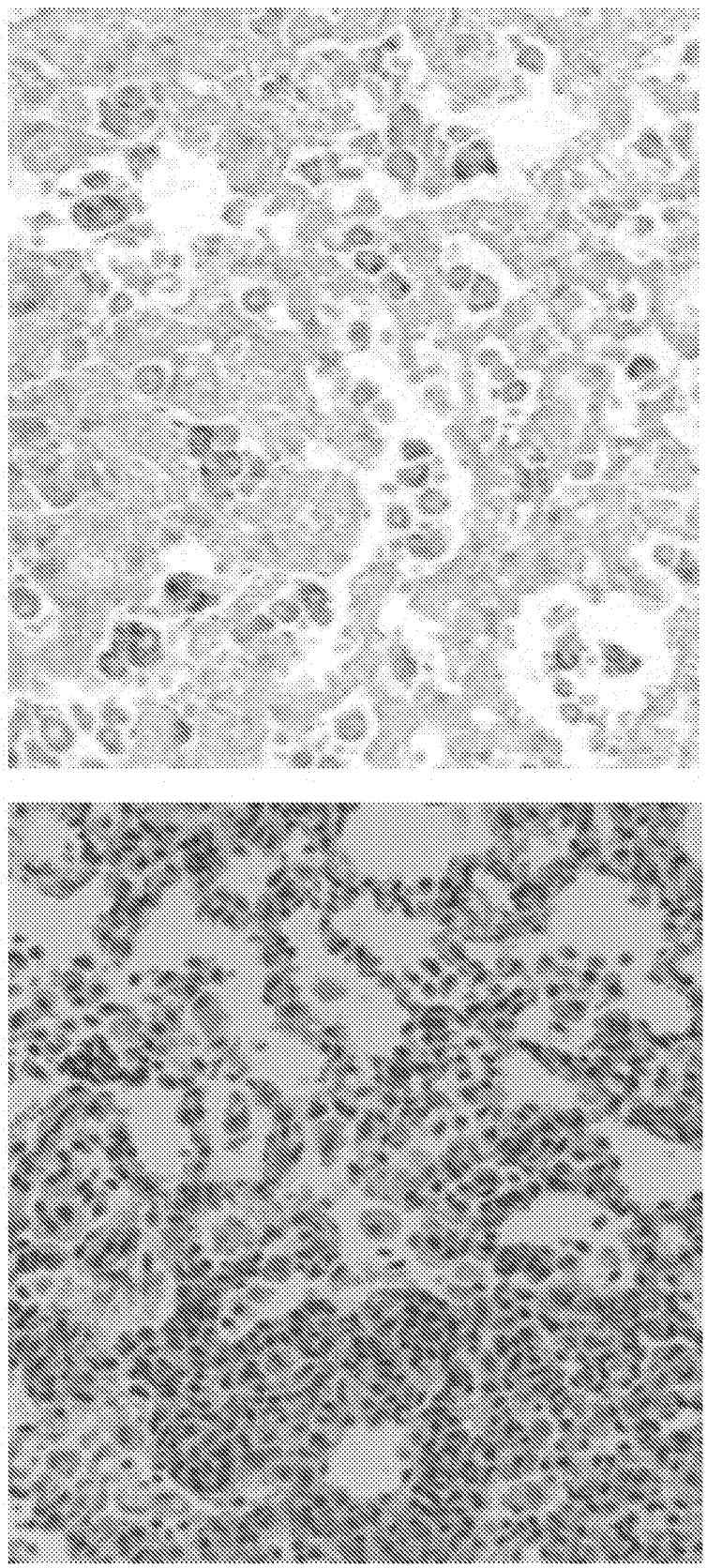
FIG. 10 represents histopathology results (H&E staining/ GMS silver staining) of the vaccination experiments described in FIG. 9. The results indicated minimal fungal burden and inflammation in those mice vaccinated with inactivated fbp1Δ deletion mutant.
Figure 11:
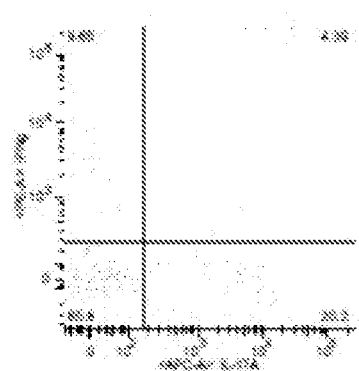
FIG. 11 represents cytokine production by CD4+ T-cells recovered by the surviving mice from the vaccination experiments described in FIG. 9, for interleukin-17 (IL-17) and IFNγ production.
Figure 11:
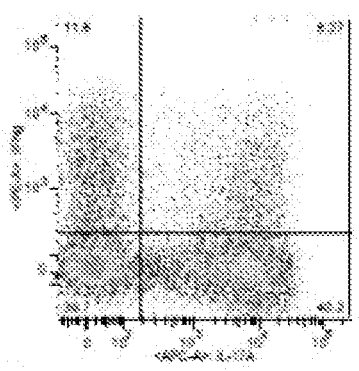
Figure 11:
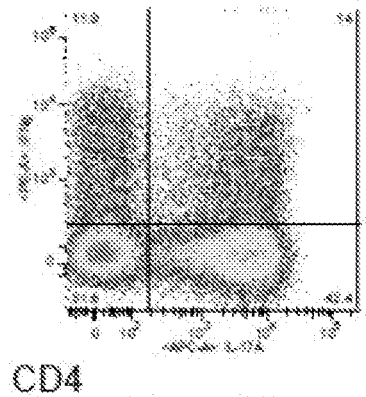
Figure 11:
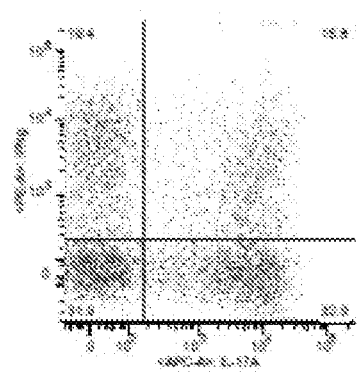
Figure 11:
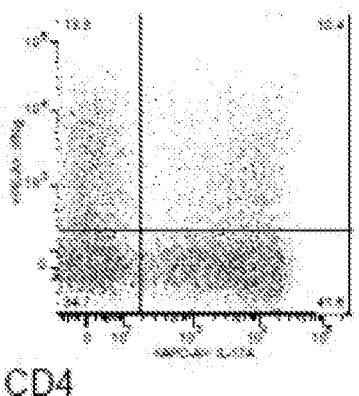
Figure 11:
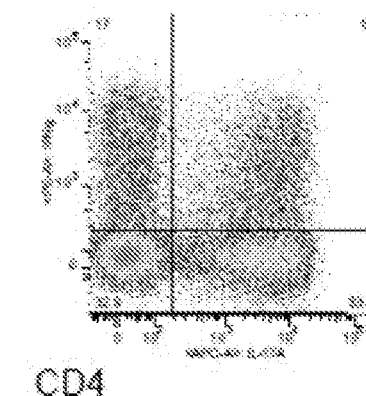
Figure 11:
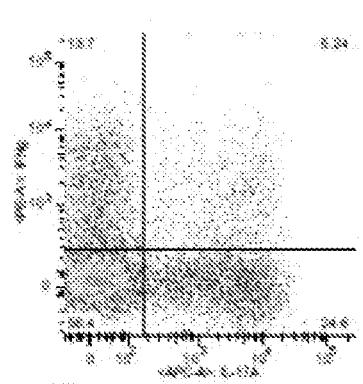
Figure 11:
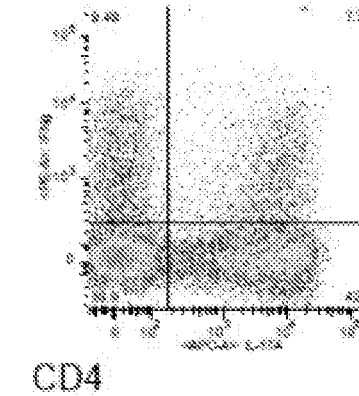
Figure 11:
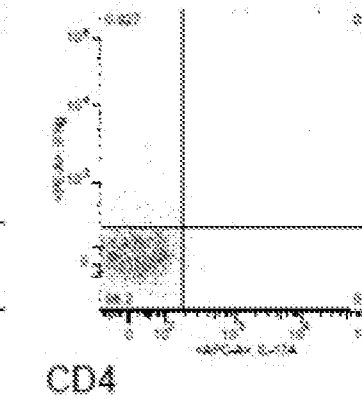
Figure 12:
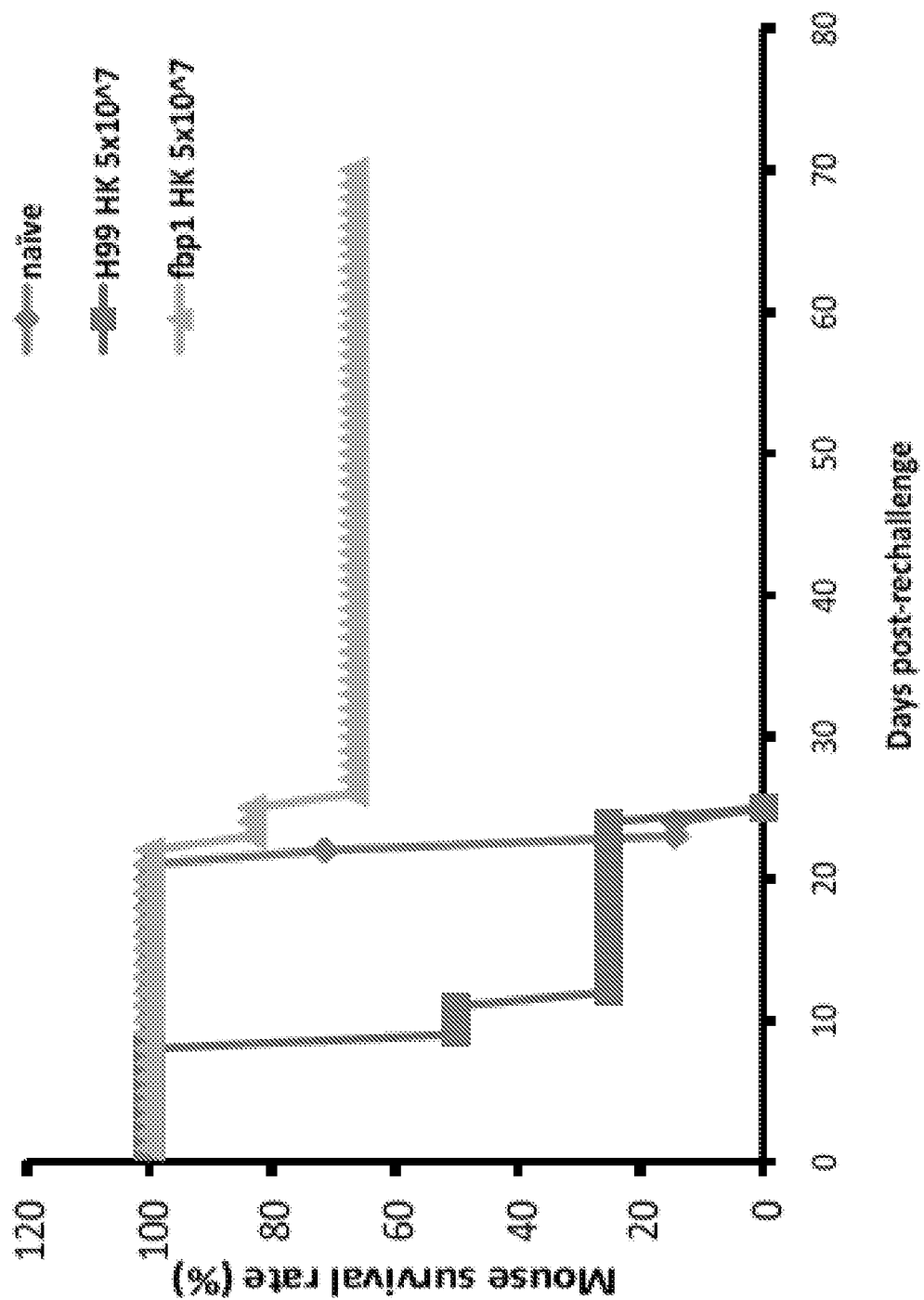
FIG. 12 represents vaccination experiments with the conditions set forth in FIG. 9 but with heat-killed H99 wild type strains instead of live fbp1Δ deletion mutants. The results showed that heat-killed H99 strains did not provide any protection against subsequent infection by live H99, whereas heat-killed fbp1Δ deletion mutants did. The results show that an effective vaccine composition must include inactivated fbp1Δ deletion mutants, either full or partial (e.g. F-box knockouts).

25 A/Jcr mice were ordered for vaccination studies. 5 were chosen as naïve control, 10 were chosen to be infected with live fbp1Δ deletion mutant ($10^6$ per mouse), and 10 were chosen to be infected with heat-killed fbp1Δ deletion mutant ($0.5 \times 10^8$ per mouse). For the mice infected with heat-killed fbp1Δ deletion mutant, a booster inoculation was given after 24 days. After 30 days, mice from each group (naïve, fbp1Δ deletion mutant, and heat-killed fbp1Δ deletion mutant) were inoculated with H99 strain of *C. neoformans* ($10^6$ per mouse). The naïve mice succumbed to infection around 25 days post-infection with H99, as well as those mice inoculated with live fbp1Δ deletion mutant. Surprisingly, those mice which were inoculated with heat-killed fbp1Δ deletion mutant showed full immunity to H99, as none of the mice succumbed to infection, even more than 60 days post infection by H99 (FIG. 9). This is surprising because although Fbp1 has been shown to be essential for virulence (discussed supra), live fbp1Δ deletion mutants do not confer immunity to infection whereas inactivated (i.e. heat-killed) fbp1Δ deletion mutants confer full immunity. Colony forming units (CFUs) were checked in lungs and brains of mice from each group, and H&E/GMS silver staining was conducted on lung tissue. The results showed that while there were no fungal cells in the brains of the surviving mice, there were trace amounts of H99 cells recovered from 5 of the 10 mice inoculated with heat-killed fbp1Δ deletion mutant. This indicated that H99 cells were contained or cleared by the mice vaccinated by heat-killed fbp1Δ deletion mutants. The histopathology results (H&E staining/GMS silver staining) indicated minimal fungal burden and inflammation (FIG. 10) especially as compared to those mice infected by H99 in the above experiments. Cytokine production was measured from CD4 cells recovered by the surviving mice, for interleukin-17 (IL-17) and IFNγ (FIG. 11). Vaccination studies were repeated as described above but including heat-killed H99 wild type strains instead of live fbp1Δ deletion mutants. The results showed that heat-killed H99 strains did not provide any protection against subsequent infection by live H99, whereas heat-killed fbp1Δ deletion mutants did (FIG. 12). This shows that an effective vaccine composition must include inactivated (e.g. heat-killed) fbp1Δ deletion mutants, either full or partial (e.g. F-box knockouts), as live fbp1Δ deletion mutants do not offer immunity, nor does heat-killed H99, only inactivated fbp1Δ deletion mutants.

Additional Vaccination Studies

Figure 13:
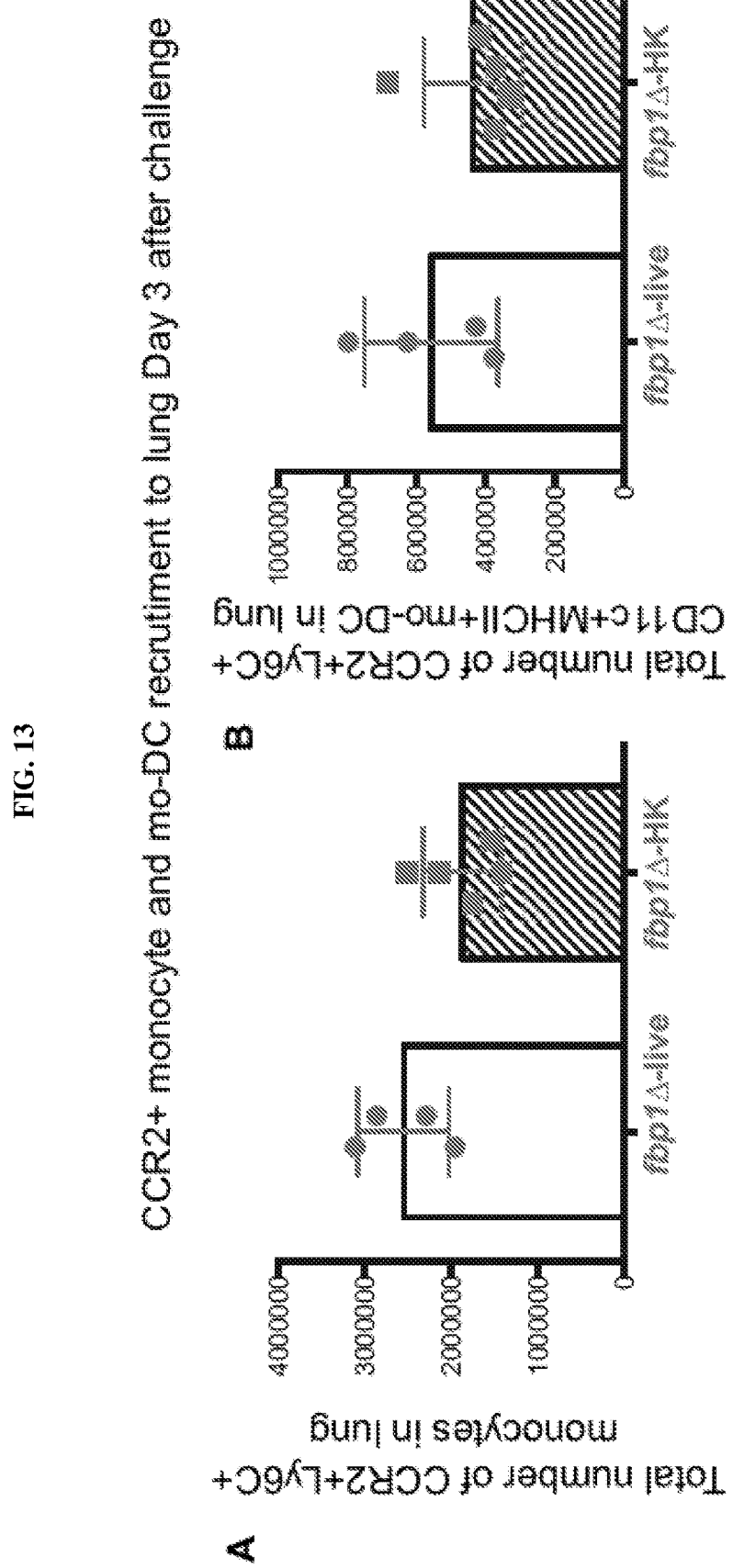
FIGS. 13A through 13E represent CCR2+ monocyte/mo-DC recruitment to lungs as well as CD4+ T-cell responses measured.
Figure 13:
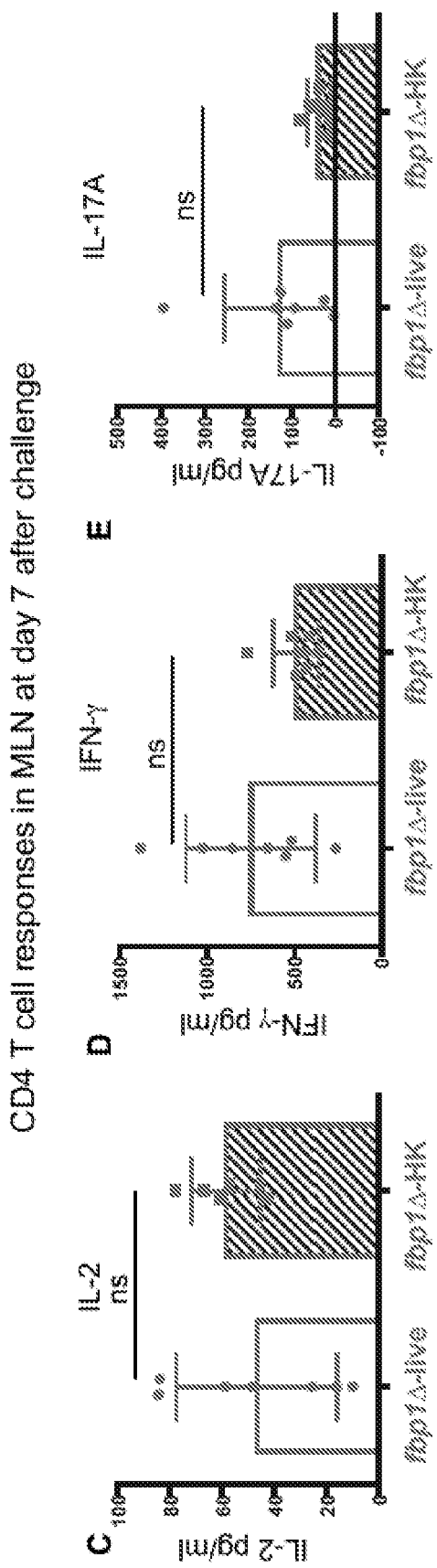

Additional vaccination studies were undertaken with the protocol set forth in the methods section of Example 3 supra. Mice challenged with live or heat-killed fbp1Δ displayed equal recruitment of $CCR2^+$ Ly6C+ monocytes (FIG. 13A, 13B) and developed comparably robust Th1 and Th17 responses (FIG. 13C, 13D, 13E). Mice were thus immunized according to the vaccination strategy employed by Zhai, et al., Development of protective inflammation and cell-mediated immunity against *Cryptococcus neoformans* after exposure to hyphal mutants. mBio. 2015; 6(5):e01433-15, hereby incorporated by reference in its entirety, to successfully protect mice against H99 challenge. Briefly, mice were immunized with heat-killed (HK) fbp1Δ at days −32 and −7 and on day 0 they were infected with $10^4$ virulent H99. The protective efficacy of vaccination in both A/Jcr and C57Bl/6J genetic backgrounds was tested. Consistent with the vaccination experiment described above, vaccination with inactivated fbp1Δ deletion mutants conferred significant protection to C57Bl/6J mice (FIG. 14A) and A/Jcr (FIG. 14B). This is in contrast to the 100% mortality of H99-challenged mice that did not receive vaccination. Consistent with previous findings, vaccination with HK-H99 was unable to confer protection from infection with live H99 (FIG. 14C). HK-fbp1Δ vaccinated mice that survived without symptoms for more than 60 days contained a significant number of $CD4^+$ T-cells that remained in the airways (FIG. 14E and FIG. 4B). Moreover, airway $CD4^+$ T-cells recovered from vaccinated mice rapidly produced IFN-γ and IL-17A upon re-stimulation (FIG. 14F and FIG. 4C, 4D). *Cryptococcus*-specific $CD4^+$ T-cell responses were also sustained in the MLN of vaccinated mice (FIG. 14G, 14H, 14I and FIG. 4E, 4F, 4G). These observations suggest that enhanced adaptive immune responses might be responsible for protection in HK-fbp1Δ-vaccinated mice. To test the importance of adaptive immunity in vaccine-mediated protection RAG−/− mice were vaccinated with HK-fbp1Δ prior to a challenge with virulent H99. It was found that vaccination with HK-fbp1Δ could not protect lymphocyte-deficient mice from a challenge with virulent H99 (FIG. 14D) thus demonstrating that lymphocytes are responsible for vaccine-mediated protection in this model. Altogether, these findings demonstrate that the development of a robust host immune response can overcome the pathogenicity of H99.

Figure 7:
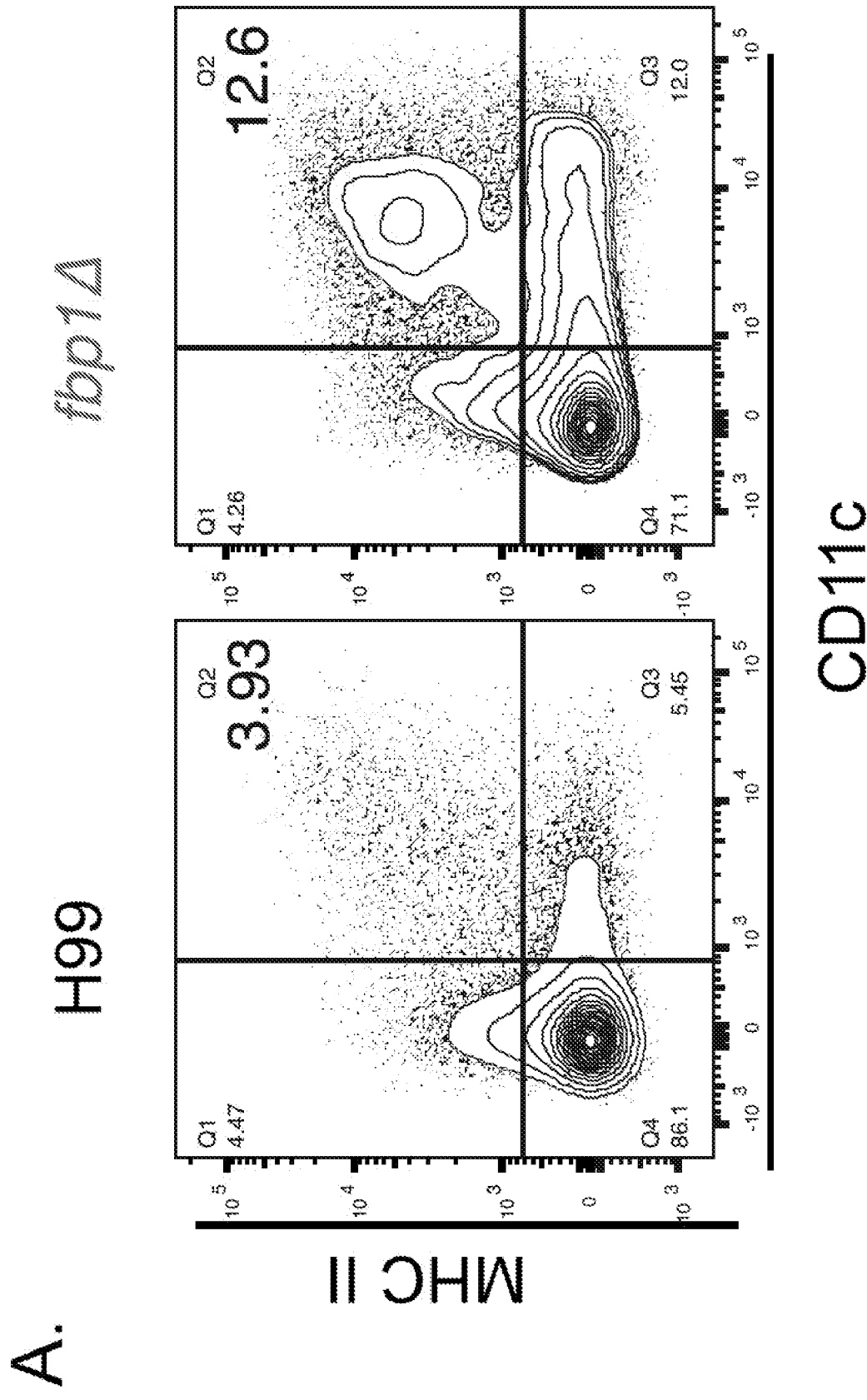
FIG. 7A through 7F represent effective maturation of $CCR2^+Ly6C^+$ monocytes into mo-DCs after Fbp1 infection. Mo-DC differentiation was analyzed at day 3 after i.n. infection with H99 or fbp1Δ. Data shown is cumulative of two independent experiments with 4-5 mice per group and is depicted as mean±SEM.
Figure 7:
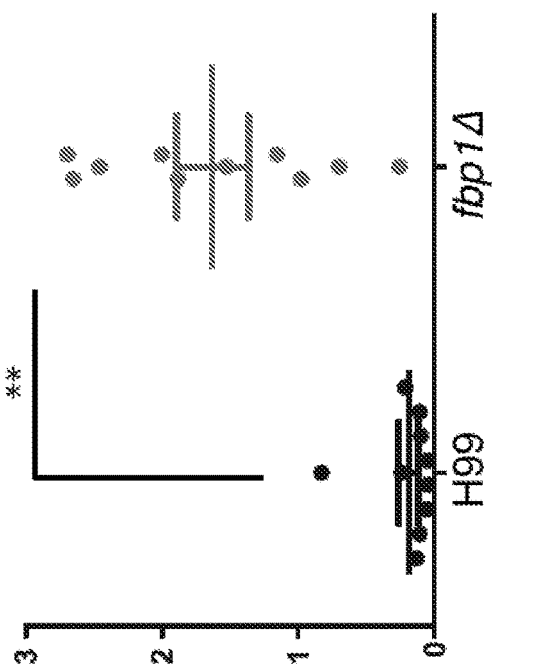
Figure 7:
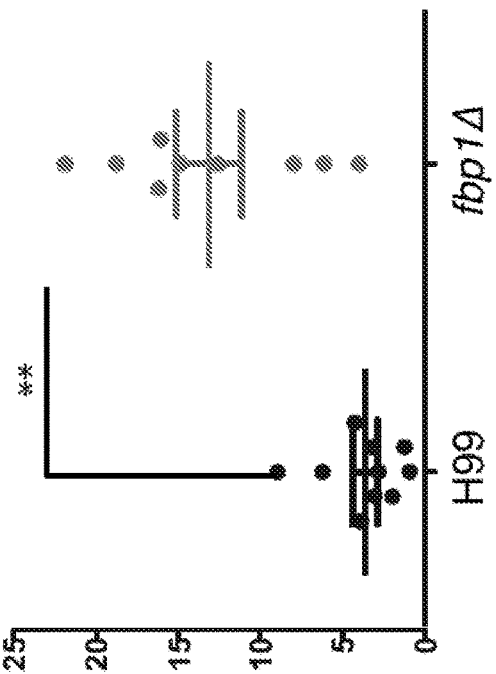
Figure 7:
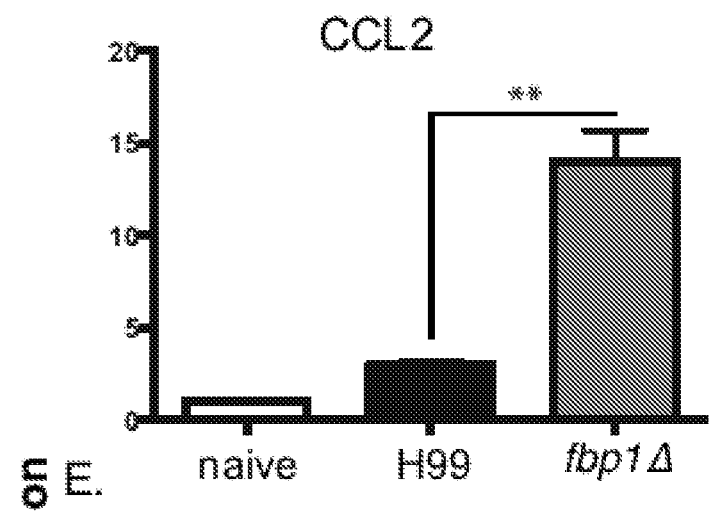
Figure 7:
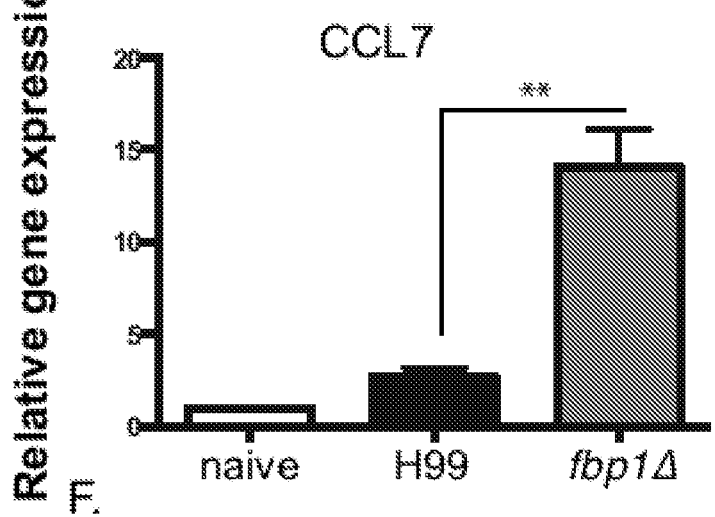
Figure 7:
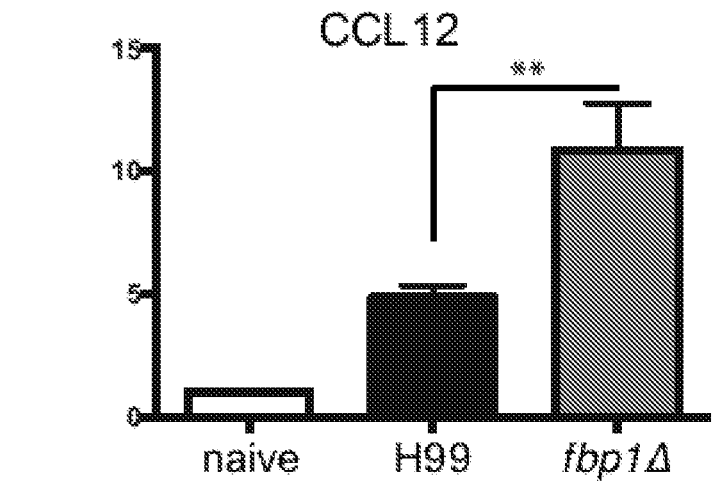
Figure 8:
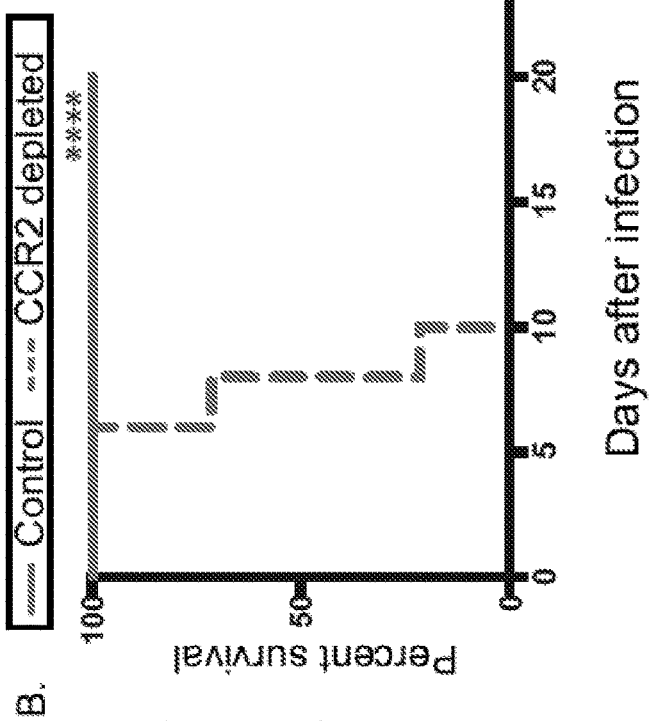
FIG. 8A through 8F represent that depletion of CCR2+ inflammatory monocytes impairs CD4+ T activation and leads to mortality of fbp1Δ infected mice. CCR2-depleter mice and control (DTR negative) littermates were treated with diphtheria toxin (DT) before and after infection with $10^6$ fbp1Δ as illustrated in FIG. 8A.
Figure 8:
Figure 8:
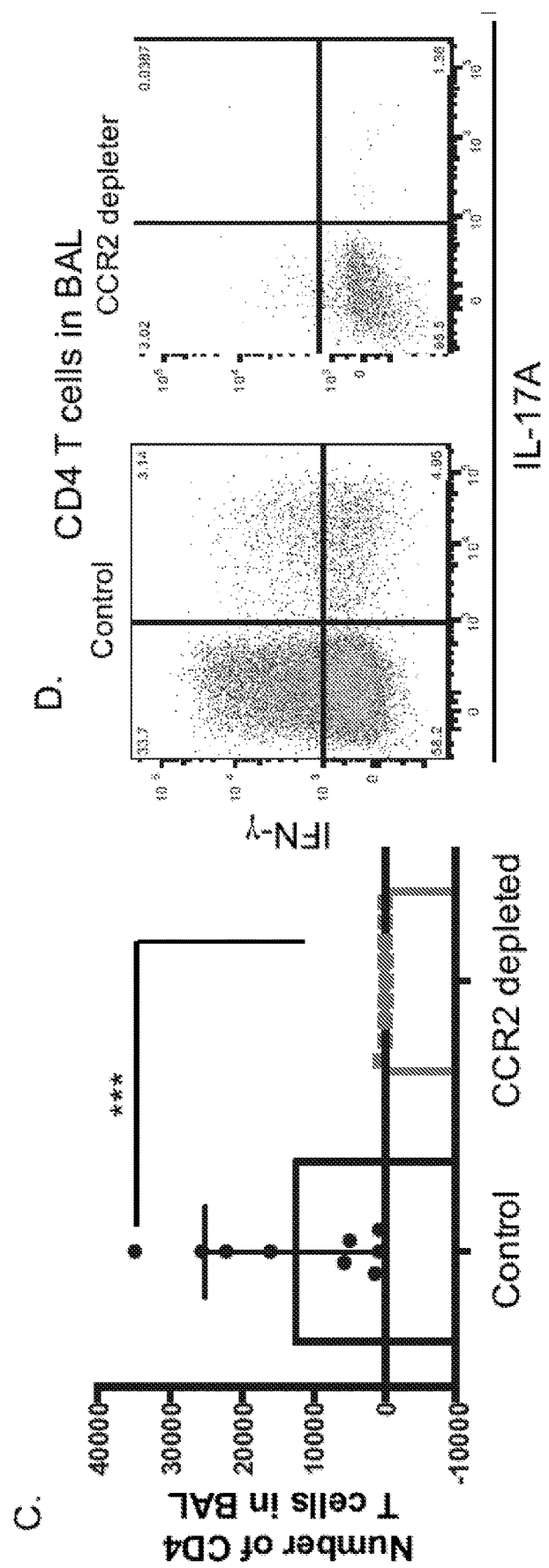
Figure 8:
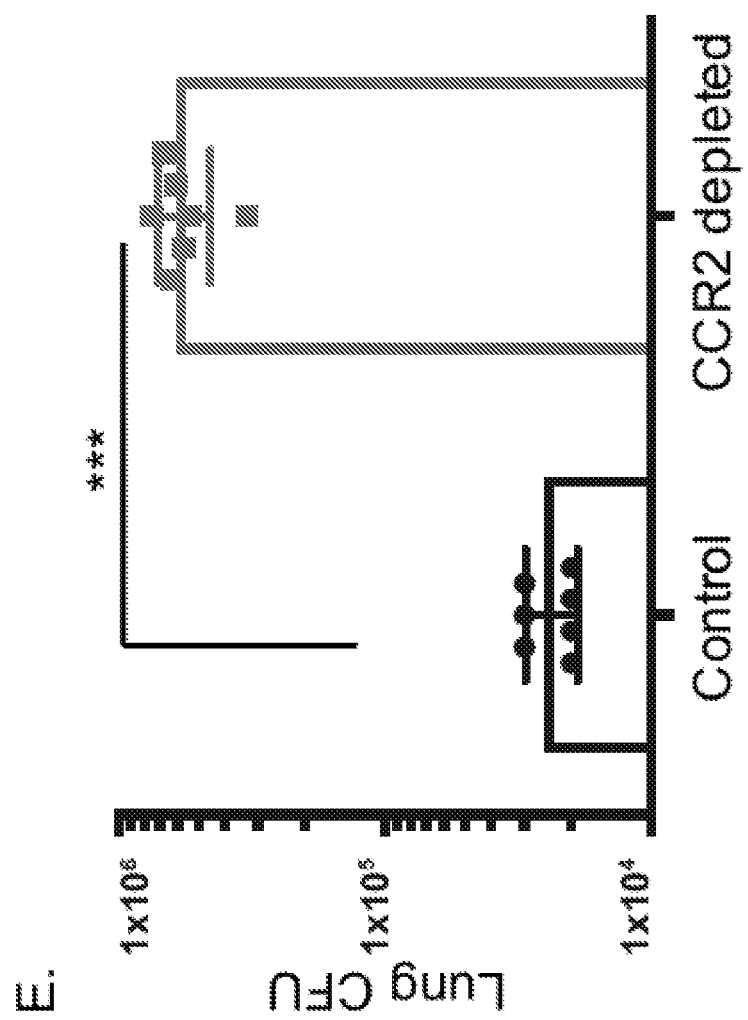
Figure 8:
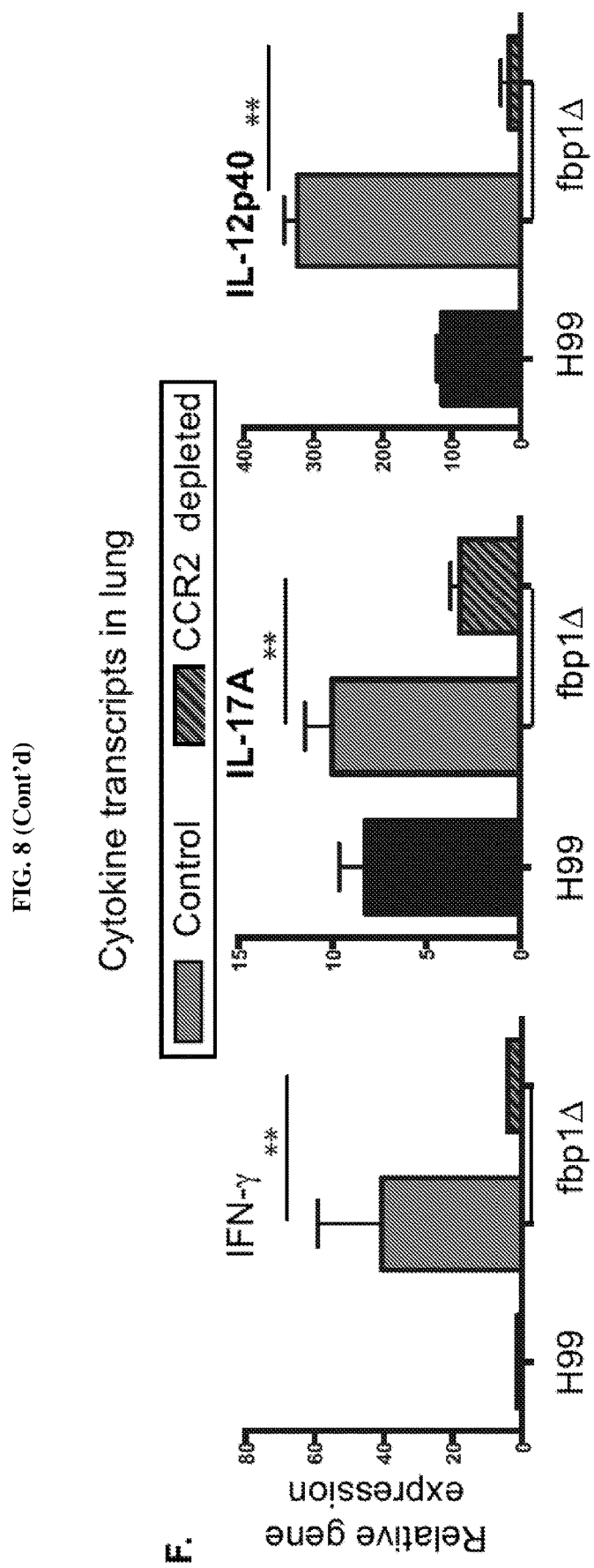
Figure 14:
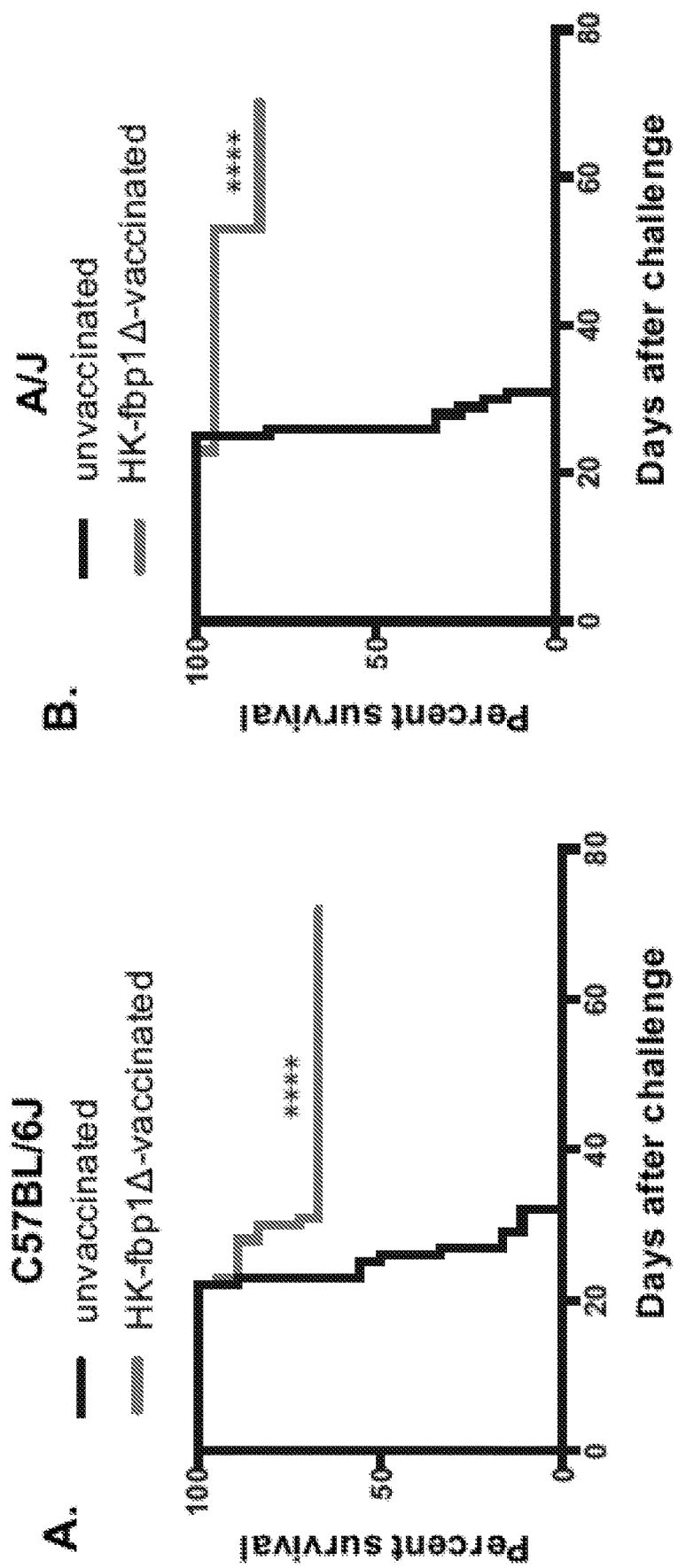
FIGS. 14A through 14I represent additional vaccination experiments, further illustrating that vaccination with inactivated fbp1Δ confers protection against H99 infection. Mice were vaccinated with heat-killed fbp1Δ yeast i.n. on days −32 and −7. At day 0 vaccinated and unvaccinated controls were infected with $10^4$ virulent H99.
Figure 14:
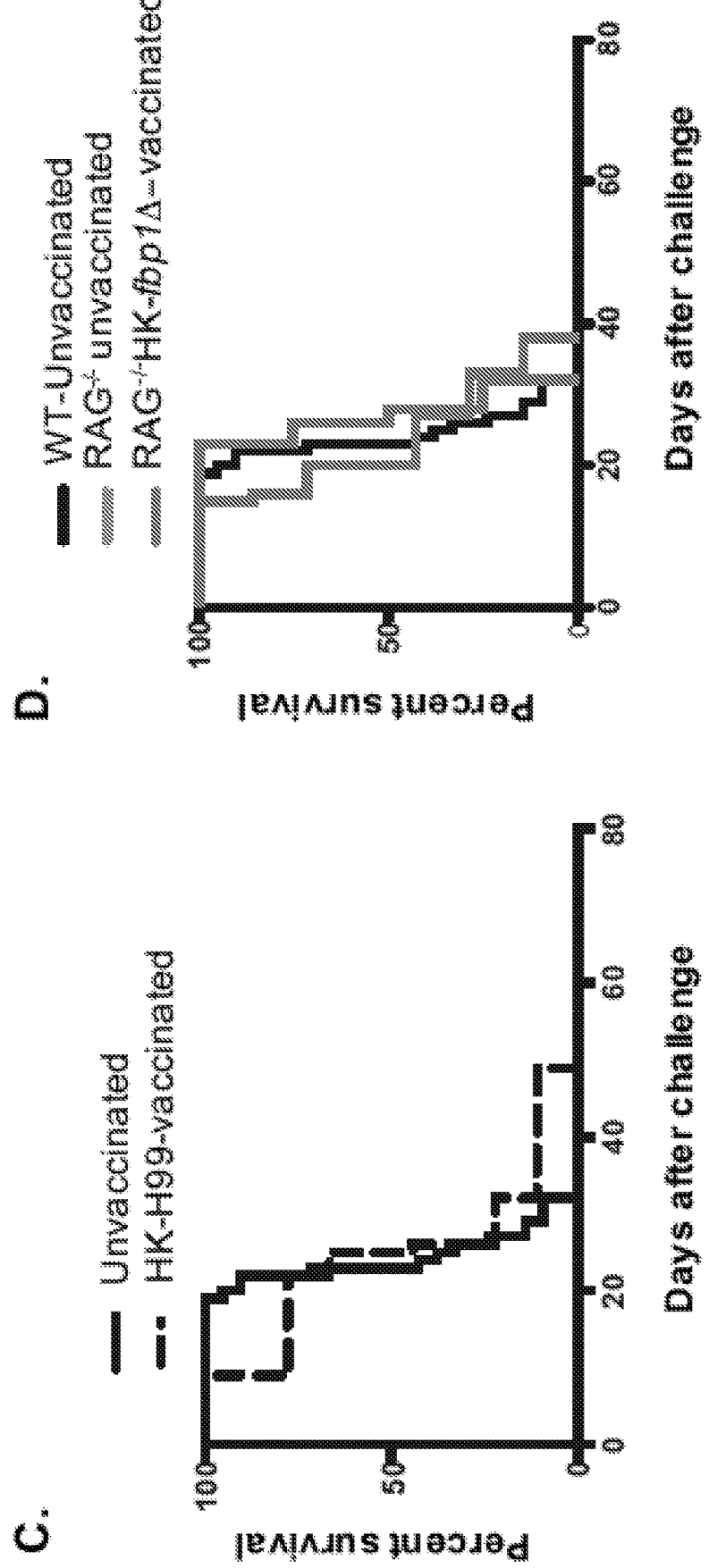
Figure 14:
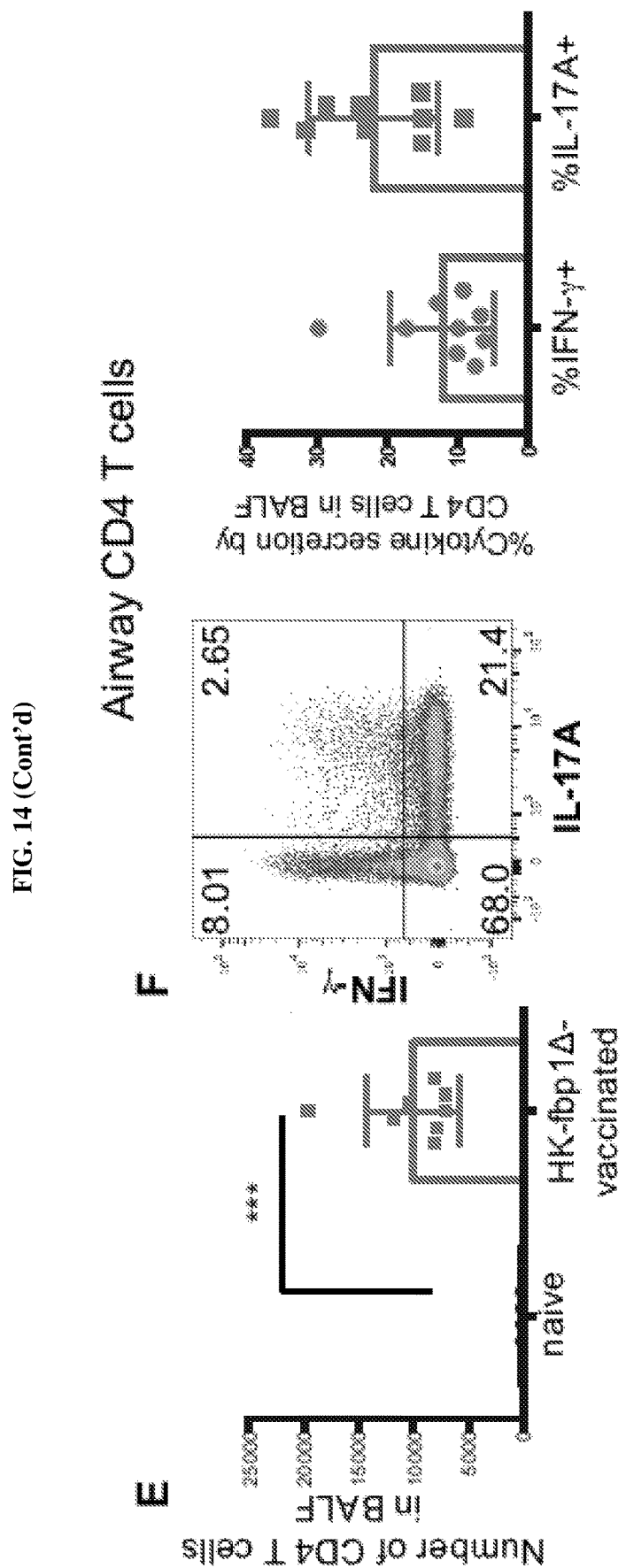
Figure 14:
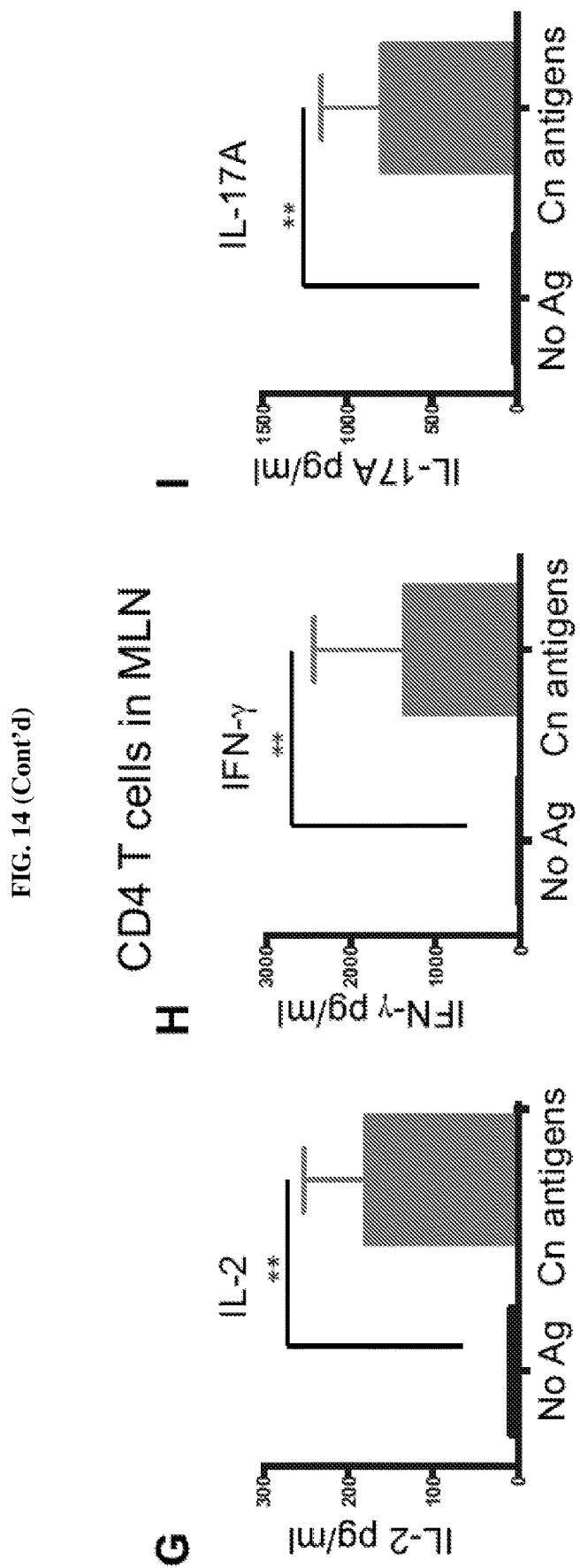

In aggregate, the vaccination results are consistent with the interpretation that the Fbp1-regulated pathway shapes the immunogenicity C. neoformans. The combined results of Example 3 and 4 illustrate that host immune responses are critical for the in vivo hypovirulent phenotype of fbp1Δ yeast. The data indicates that the long-term survival of mice infected with fbp1Δ (FIG. 3) is dependent on the activation of protective adaptive immunity (FIG. 5 and FIG. 6) and by increased recruitment and differentiation of $CCR2^+Ly6C^+$ monocytes (FIG. 7 and FIG. 8). It was found that enhanced innate and adaptive immune responses cooperate to help protect the host from infection with fbp1Δ. Surprisingly, it was discovered that mice which were inoculated with heat-killed fbp1Δ deletion mutant showed full immunity to H99 whereas live fbp1Δ deletion mutants do not confer immunity to infection with H99. Furthermore, heat-killed H99 does not confer immunity. Importantly, this protective immune response to inactivated (e.g. heat-killed) fbp1Δ deletion mutants can be harnessed in vaccination strategies to prevent mortality against challenge with the virulent parental strain H99 (FIG. 14).

Figure 15:
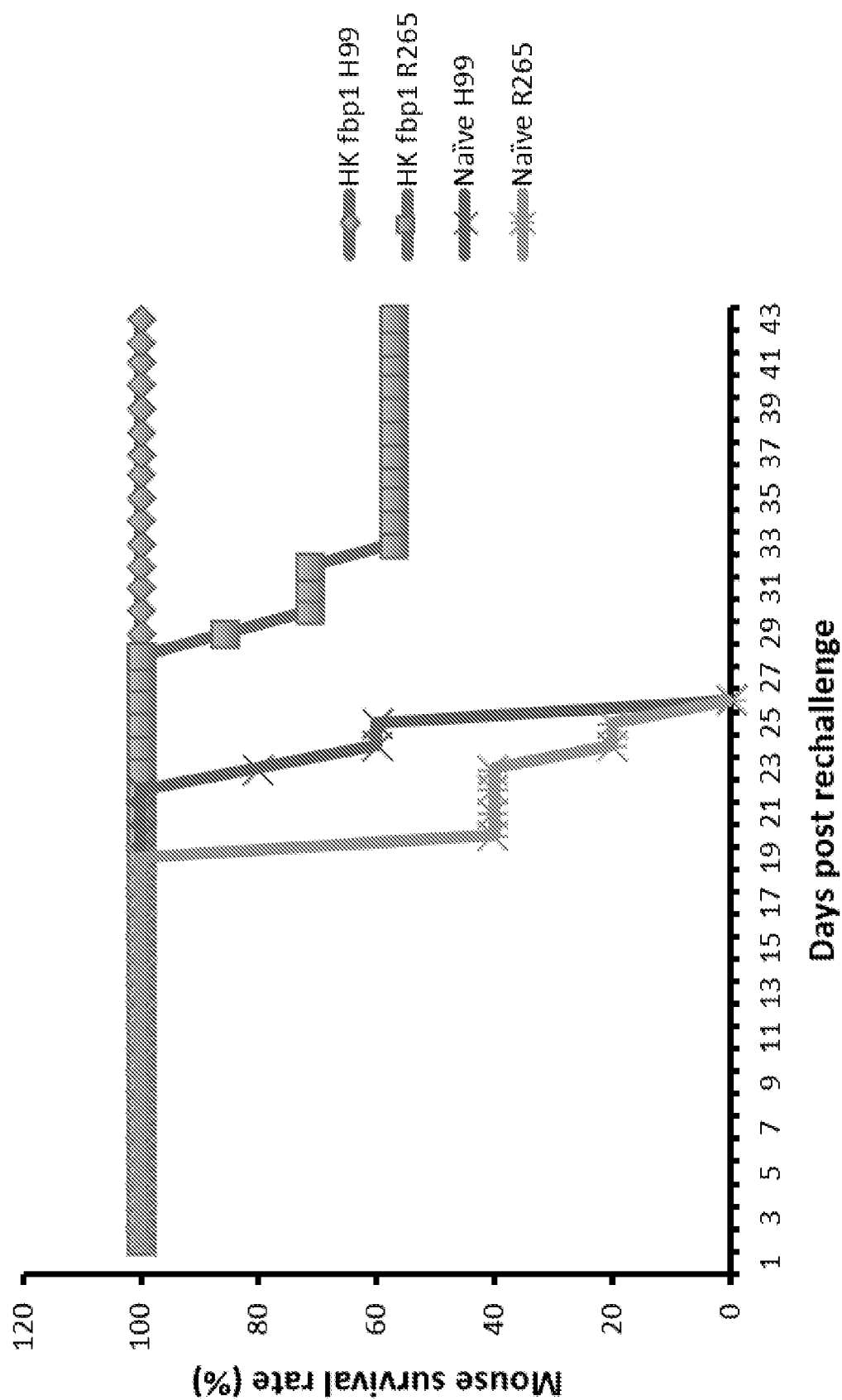
FIG. 15 represents the results of cross-protection tests using inactivated fbp1Δ deletion mutants. A/Jcr mice were vaccinated with heat-killed fbp1Δ deletion mutant cells. The results indicated that, in addition to protection against H99 strain, the inactivated fbp1Δ deletion mutants can protect mice from rechallenge of highly virulent *C. gattii* strain R265.

5. Vaccination with Inactivated (Heat-Killed) fbp1Δ Mutants Confers Cross-Protection Against Infection with Other Fungal Species Vaccination studies were undertaken utilizing the protocol set forth in Example 4 supra with the following modifications. Briefly, mice were immunized with heat-killed (HK) fbp1 A deletion mutants. After one month, the mice were infected with virulent *Cryptococcus gattii* (*C. gattii*) strain R265, a virulent sibling species of *C. neoformans* that often causes infection in immunocompetent individuals, or with *C. neoformans* strain H99. Mice not vaccinated (naïve) were also infected with both virulent strains R265 and H99 as control. The results are indicated in FIG. 15. Briefly, by 26 days post infection, 100% of the naïve mice had died, compared to 0% of the mice infected with H99 and 0% of the mice infected with R265. By day 43, survival among mice infected with H99 was still 100% and for mice infected with R265 the survival rate was approximately 60%. The results thus indicate that heat-killed (HK) fbp1Δ deletion mutants confer significant cross-protection against infection with fungus other than *C. neoformans* (*C. gattii* in this instance).

Additional vaccination studies are undertaken. Briefly, mice are immunized with heat-killed (HK) fbp1Δ and are infected with one of i) virulent *Candida albicans* (*C. albicans*) strain ATCC90028 or ii) virulent *Aspergillus fumigatus* (*A. fumigatus*) strain ATCC13073. Mice re-challenged with virulent *Cryptococcus neoformans* strain H99 are used as a control. Mouse survival rates are monitored to determine protection. Results indicate vaccination with inactivated (heat killed) fbp1Δ deletion mutants confer significant protection against infection with *C. albicans*. Results indicate vaccination with inactivated (heat killed) fbp1Δ deletion mutants confers significant protection against infection with *A. fumigatus*. Vaccination with inactivated (heat killed) fbp1Δ deletion mutants confer significant protection against infection with virulent H99.

6. Vaccination with Inactivated (Heat-Killed) fbp1Δ Mutants Confer Protection Against Infection in Immune Deficient Animals Vaccination studies are undertaken utilizing the protocol set forth in Example 4 supra with the following modifications. Briefly, mice are immunized with heat-killed (HK) fbp1Δ at days −32 and −7. Additionally at day −7, mice are intraperitoneally injected with 200 µg anti-CD4 antibody (GK1.5). Mice continue to be intraperitoneally injected with 200 µg anti-CD4 antibody on a weekly basis throughout the experiment. Depletion of $CD4^+$ T-cells in mice is determined by anti-CD4 antibody staining and flow cytometry analysis. At day 0, mice are infected with one of the following: i) virulent *Cryptococcus neoformans* strain H99; ii) parental *Cryptococcus gattii* (*C. gattii*) strain R265; iii) virulent *Candida albicans* (*C. albicans*) strain ATCC90028; iv) virulent *Aspergillus fumigatus* (*A. fumigatus*) strain ATCC13073. Results indicate vaccination with inactivated (heat killed) fbp1Δ deletion mutants confer significant protection against infection with virulent H99. Results indicate vaccination with inactivated (heat killed) fbp1Δ deletion mutants confer significant protection against infection with *C. gattii* strain R265. Results indicate vaccination with inactivated (heat killed) fbp1Δ deletion mutants confer significant protection against infection with *C. albicans*. Results indicate vaccination with inactivated (heat killed) fbp1Δ deletion mutants confer significant protection against infection with *A. fumigatus*.

TABLE 1

Primers utilized in the Examples

| Primer Sequence | SEQ ID NO: | Identifier | Reference/Notes |
| --- | --- | --- | --- |
| GTAAAACGACGGCCAG | SEQ ID NO: 1 | CX5 | M13F |
| CAGGAAACAGCTATGAC | SEQ ID NO: 2 | CX6 | M13R |
| CATGGGATCCACATGCCCGTACGACCGTCAAG | SEQ ID NO: 3 | CX34 | FBP1A YTH PGADT7/PGBKT7 |
| CATGGGATCCACATGCCCGTACGACCGTCAAG | SEQ ID NO: 4 | CX35 | FBP1A YTH PGBKT7 |
| CGACCTGCAGTCAACGTCCGTTACCGAATC | SEQ ID NO: 5 | CX36 | FBP1A YTH PGBKT7 |
| GAAATGTCATCGCCTGTGTGCCAA | SEQ ID NO: 6 | CX44 | FBP1 QRT-PCR |
| TGTCAAACTTGATCCTGCGGAGCA | SEQ ID NO: 7 | CX45 | FBP1 QRT-PCR |
| TGAGAAGGACCCTGCCAACA | SEQ ID NO: 8 | CX49 | GAPDH QRT-PCR |
| ACTCCGGCTTGTAGGCATCAA | SEQ ID NO: 9 | CX50 | GAPDH QRT-PCR |

TABLE 1-continued

Primers utilized in the Examples

| Primer Sequence | SEQ ID NO: | Identifier | Reference/Notes |
|---|---|---|---|
| CTAGCATATGATGGCCGAGAAGAAGCAGAC | SEQ ID NO: 10 | CX71 | SKP1 YTH PGADT7 |
| CTAGGAATTCTTAACGGTCCTCAGCCCACTC | SEQ ID NO: 11 | CX72 | SKP1 YTH PGADT7 |
| CCTGGGATCCATGTCGCAAGACTTTAGCGTCT | SEQ ID NO: 12 | CX78 | Cik2 YTH pGBKT7 |
| ATGGCCATGGAGGCCATGTCGCAAGACTTTAGCGTCT | SEQ ID NO: 13 | CX79 | Cik2 YTH pGBKT7 |
| CATATGGCCATGGAGGCCATGGTGACTTCTAATGTTGTC | SEQ ID NO: 14 | CX88 | ScSKP1 YTH pGADT7 |
| CGATGGATCCCTAACGGTCTTCAGCCCATTC | SEQ ID NO: 15 | CX89 | ScSKP1 YTH pGADT7 |
| GAGTTGCGTGATTGTGTTCTTAATTTCACCCCTTT | SEQ ID NO: 16 | CX198 | F-BOX deletion overlap PCR |
| GGTGAAATTAAGAACACAATCACGCAACTCGCCTC | SEQ ID NO: 17 | CX199 | F-BOX deletion overlap PCR |
| ATGCAGCAATGGACTGGTGTCAAC | SEQ ID NO: 18 | CX294 | HXT3 QRT-PCR |
| TGAACTCGCAGATGAGCATACCGA | SEQ ID NO: 19 | CX295 | HXT3 QRT-PCR |
| GTACTGAGCGATGCTGCAGTG | SEQ ID NO: 20 | CX278 | FBP1 KO left |
| CTGGCCGTCGTTTTACTACGGCGAGTGAGTTCGGAC | SEQ ID NO: 21 | CX279 | FBP1 KO left |
| GTCATAGCTGTTTCCTGCGATTCGGTAACGGACGTTG | SEQ ID NO: 22 | CX280 | FBP1 KO right |
| ACTTTCGGCGACGACATCAC | SEQ ID NO: 23 | CX281 | FBP1 KO right |
| GACCGTCAAGAAGCAACTCG | SEQ ID NO: 24 | CX282 | FBP1 KO negative |
| CAGATTGATAGCTTGCAGCTTC | SEQ ID NO: 25 | CX283 | FBP1 KO negative |
| GGAATCAACGAAGATCTGAAGG | SEQ ID NO: 26 | CX284 | FBP1 KO positive |
| CGATGGGCCCTCGTGCAGGGCTTCCAGCAG | SEQ ID NO: 27 | CX285 | Fbp1 complementation |
| GATCCTCGAGTCACATCATCATCATCATACGTCCGTTACCGAATCGTTG | SEQ ID NO: 28 | CX286 | Fbp1 complementation |
| TGTGGATGCTGGCGGAGGATA | SEQ ID NO: 29 | JH8994 | For positive screen |
| CATAAATACAGGATCCATGCCCGTACGACCGTCAAGAA | SEQ ID NO: 30 | CX225 | FBP1 in-fusion F1 |
| ACGCGGCCGCTTACTTATCGTCGTCATCCTTGTAATCACGTCCGTTACCGAATCGTTGT | SEQ ID NO: 31 | CX443 | FBP1-FLAG in-fusion R1 |
| GCAGCCCGGGGATCCATGTCTACTGTGACTTCTCCCG | SEQ ID NO: 32 | CX432 | PFK27HA F1 |
| ACGTCGTATGGGTAGGATCCCTCGTGATGCAATTGCGCAGCTAC | SEQ ID NO: 33 | CX542 | PFK27HA R1 |
| GTGGCGGCCGCTCTAGATTAAGCGTAATCTGGTACGTCGTATG | SEQ ID NO: 34 | CX541 | PFK27HA R2 |
| GCAGCCCGGGGATCCATGCCCGAAACGAATACCTCCG | SEQ ID NO: 35 | CX543 | CIR1HA F1 |
| TCGTATGGGTAGGATCCACTCCTAACGTCAAAACTCCAC | SEQ ID NO: 36 | CX433 | CIRHA R1 |
| GCAGCCCGGGGATCCATGAACTCACAATCTCCCCCTG | SEQ ID NO: 37 | CX551 | ISC1HA F1 |
| TCGTATGGGTAGGATCCACGATGTACATTCTCGTCCATC | SEQ ID NO: 38 | CX552 | ISC1HA R1 |

TABLE 1-continued

Primers utilized in the Examples

| Primer Sequence | SEQ ID NO: | Identifier | Reference/Notes |
|---|---|---|---|
| CAACATGTCTGGATCCATGAACTCACAATCTCCCCCTG | SEQ ID NO: 39 | CX586 | ISC1HA F2 |
| TTCTTTTACGCGGCCGCTTAAGCGTAATCTGGTACGTCG | SEQ ID NO: 40 | CX587 | ISC1HA R2 |
| CGAGCTGTACGGATCCATGAACTCACAATCTCCCCCTG | SEQ ID NO: 41 | CX588 | GFP-ISC1HA F1 |
| CGTTACTAGTGGATCCCTTAAGCGTAATCTGGTACGTCG | SEQ ID NO: 42 | CX589 | GFP-ISC1HA R1 |
| ACGCGGCCGCTTACTTATCGTCGTCATCCTTGTAATCCACTGATAGAGAGGT GAATAGC | SEQ ID NO: 43 | CX515 | F-BOX FLAG R1 |
| TAATCTGGTACGTCGTATGGGTAACGATGTACATTCTCGTCCATC | SEQ ID NO: 44 | CX630 | ISC1HA R1(native promoter) |
| ATCCACTAGTTCTAGAGTGGCATGCGGGGCTCAGGTATCG | SEQ ID NO: 45 | CX633 | ISC1HA F1(native promoter) |
| TGGCGGCCGCTCTAGATTAAGCGTAATCTGGTACGTCGTATGGG | SEQ ID NO: 46 | CX634 | ISC1HA R2(native promoter) |
| CGGTACCCGGGGATCCTCAATGATGATGATGATGATGACGTCCGTTACCGAATCGTT | SEQ ID NO: 47 | CX231 | F-box deletion infusion PCR |

TABLE 2

Fungal strains and plasmids utilized in the Examples

| Strains | Genotype |
|---|---|
| H99 | MATα |
| KNN99a | MATa |
| CDX40 | MATa gpa1::NAT ura5 P$_{GPD1}$-GPA1$^{Q284L}$:Flag-URA |
| CUX2 | MATα fbp1::NEO |
| CUX3 | MATa fbp1::NEO |
| CUX5 | MATα fbp1::NEO FBP1-NAT |
| CUX6 | MATa fbp1::NEO FBP1-NAT |
| CUX83 | MATα ura5 |
| CUX84 | MATa ura5 |
| CUX87 | MATα fbp1::NEO ura5 |
| CUX88 | MATa fbp1::NEO ura5 |
| CUX134 | MATα fbp1::NEO ura5 P$_{ACT}$-FBP1:FLAG-URA5 |
| CUX135 | MATα fbp1::NEO ura5 P$_{ACT}$-FBP1$^{AF}$:FLAG-URA5 |
| CUX138 | MATα fbp1::NEO ura5 P$_{ACT}$-FBP1:FLAG-URA5 |
| CUX142 | MATα fbp1::NEO ura5 P$_{ACT}$-F-BOX:FLAG-URA5 |
| CUX157 | MATα fbp1::NEO ura5 P$_{ACT}$-FBP1:FLAG-URA5 P$_{CTR4}$-PFK27:HA-NAT |
| CUX160 | MATα fbp1::NEO ura5 P$_{ACT}$-FBP1:FLAG-URA5 P$_{CTR4}$-ISC1:HA-NAT |
| CUX163 | MATα fbp1::NEO ura5 P$_{CTR4}$-PFK27:HA-URA5 |
| CUX167 | MATα fbp1::NEO P$_{CTR4}$-ISC1:HA-NAT |
| CUX168 | MATα P$_{HIS}$-GFP:ISC1:HA-NAT |
| CUX169 | MATa P$_{HIS}$-GFP:ISC1:HA-NAT |
| CUX170 | MATα ura5 P$_{ACT}$-ISC1:HA-URA5 |
| CUX172 | MATα ade2 isc1::ADE2 |
| CUX173 | MATα ade2 isc1::ADE2 ISC1-NAT |
| CUX209 | MATα fbp1::NEO ISC1:HA-NAT |
| CUX220 | MATα ISC1:HA-NAT |
| CUX221 | MATα fbp1::NEO CRK1:HA-NAT |
| CUX222 | MATα CRK1:HA-NAT |

| Plasmids | Description |
|---|---|
| pCTR4-2 | This vector contains the CTR4 inducible promoter |
| pCN19 | P$_{HIS}$-GFP |
| pCXU117 | P$_{ACT}$-FBP1$^{AF}$:FLAG (CX225/CX443, BamHI/NotI) |
| pCXU118 | P$_{ACT}$-FBP1:FLAG (CX225/CX443, BamHI/NotI) |
| pCXU155 | P$_{ACT}$-F-BOX:FLAG (CX225/CX515, BamHI/NotI) |
| pCXU166 | P$_{CTR4}$-PFK27:HA (CX432/CX531, BamHI/XbaI) |
| pCXU170 | P$_{CTR4}$-ISC1:HA (CX551/CX552, BamHI) |
| pCXU176 | pCN19 + ISC1:HA (CX588/CX589, BamHI) |
| pCXU177 | P$_{ACT}$-ISC1:HA (CX586/CX587, BamHI/NotI) |
| pCXU178 | pJAF13 + ISC1HA (CX633/CX634, XbaI) |
| pCXU189 | pJAF13 + CRK1HA (CX80/CX298, XbaI/XhoI) |

(SEQ ID NO: 48)
MPVRPSRSNSDSSIRHVANSSPASSYRPTSIRERETSPINAFNQLSLDRS

LTPPKAPRLAPQVTRDPKYTRHIRSQVLRNTSRTPSAASTDDEDDQDERG

RGGIDEEAKSWLELRDGRGWKRNGKYKGVNKRGEIKNDLTN<u>QLPPEILIQ</u>

<u>IFRYLPGNKDLLSVLLVSRFWCLCAFSLLWYKPTLPTITQ</u>LASIIRVIHS

PTRSLPYANAIRRLPLIQLGPTLTDELFTSLSVCSRLERLNISGADKLTS

GALRNVIACVPNLVSLDLTGVINTDDAVLVVVGETCKKLQAINLSECRLV

GDEGVLALAKESRVLRRIKFDKCHRITQKSLIPLIRACPLVLEYDLQDVI

SLSSSVLHTVFLHASHLRELRVNGCVSLDENCIPNLLDLSEMQDDWIAKV

-continued

SEDVGIKVEPAEGVTMLRPVTTTFEYLRVVDMTGCTDLGDKAVDNLITNA

PKLRQLTLNKCPALTDKSLESIGKLGKHLHNLHLGHVSLITDDGVINLAK

SCTRLRYLDLACCTLLTDACVAEIGENMPKLKRFGLVKVTNITDEAIYSL

VRKHTSLERVHLSYCDQLSVKAIAYLLNKLAHIKHLSLTGVSSFKVPELQ

EFCRPPPDFFNDHQRAAFCVFSGSRVVELRDYLNNHYLPSMEIDTSEDSG

HDGAASSTSSLTIPRAAPTPDHSSISNSILQHNNLVYRQSLSNLNDAWED

AAPPISPTPMSRPQPPHLFTTSIQYQSAQPGENAPFPIASTSTSPPAFMS

SSSARPTSNLTSATPSYFNISLSPSLHNRFAYGDTTLPPHLDYLVPPSQE

SSRSSSISSNGDRLPFIPHQGVSDRSRGPDAQGRRDRPSGPRVPSGSYNV

SPSYANEFTTYWPREGRLPRASDSGIGITRAHSAEEHMTQVANLSQRSSA

NGSLSSSAGAQREGGRGPRWLQRFGNGR.

Full length sequence (928 AA) of FBP1 protein in *C. neoformans*. F-box domain is underlined. The F-box domain precedes the 12 LRRs; see also FIG. 1 of Liu et al. Eukaryot Cell. 2011 June; 10(6):791-802, hereby incorporated by reference in its entirety.

(SEQ ID NO: 49)
LPPEILIQIFRYLPGNKDLLSVLLVSRFWCLCAFSLLWYKPTLPTITQL

Sequence of F-Box Domain.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

---

The invention claimed is:

1. A vaccine comprising an inactivated F-box protein 1 deletion (fbp1Δ) mutant *Cryptococcus neoformans* cell, wherein the inactivated fbp1Δ mutant cell is heat-killed, and wherein the fbp1Δ is a full deletion or a partial deletion.

2. The vaccine of claim 1 further comprising at least one adjuvant.

3. The vaccine of claim 1 further comprising a pharmaceutically acceptable carrier.

4. The vaccine of claim 1, wherein the fbp1Δ is a partial deletion.

5. The vaccine of claim 4 wherein the partial deletion is of an F-box domain.

6. The vaccine of claim 1 wherein the fbp1Δ occurs by homologous recombination.

7. The vaccine of claim 4 wherein the partial deletion occurs by homologous recombination.

8. The vaccine of claim 1, wherein the fbp1Δ is a full deletion.

9. A method of stimulating an immune response in a host organism comprising administering to said host organism the vaccine of claim 1.

10. The method of claim 9 further comprising administering at least one adjuvant.

11. The method of claim 9 wherein the administering step occurs more than once.

12. A method of treating or protecting against a fungal infection in a subject in need thereof comprising administering to said subject the vaccine of claim 1.

13. The method of claim 12, further comprising administering at least one antifungal agent to said subject.

14. The method of claim 12 wherein the administering step is repeated more than once.

15. The method of claim 12 wherein the fungal infection comprises an infection with a virulent strain of *C. neoformans*.

16. The method of claim 12 wherein the fungal infection comprises an infection with *C. albicans, A. fumigatus*, or *C. gattii*.

17. The method of claim 12 wherein the subject is an immunocompromised subject.

18. The method of claim 17 wherein the immunocomprised subject is infected with human immunodeficiency virus (HIV).

* * * * *

UNITED STATES PATENT AND TRADEMARK OFFICE
CERTIFICATE OF CORRECTION

PATENT NO. : 10,987,422 B2
APPLICATION NO. : 16/317186
DATED : April 27, 2021
INVENTOR(S) : Chaoyang Xue et al.

Page 1 of 1

It is certified that error appears in the above-identified patent and that said Letters Patent is hereby corrected as shown below:

In the Specification

Delete the paragraph under the STATEMENT REGARDING FEDERAL FUNDING on Column 1, Line number 16 and replace with the following:

--This invention was made with government support under grant number AI115204 awarded by the National Institutes of Health. The government has certain rights in the invention.--

Signed and Sealed this
Twenty-seventh Day of May, 2025

Coke Morgan Stewart
*Acting Director of the United States Patent and Trademark Office*

SEQUENCE LISTING

<160> NUMBER OF SEQ ID NOS: 49

<210> SEQ ID NO 1
<211> LENGTH: 16
<212> TYPE: DNA
<213> ORGANISM: Cryptococcus neoformans

<400> SEQUENCE: 1
gtaaaacgac ggccag                                                       16

<210> SEQ ID NO 2
<211> LENGTH: 17
<212> TYPE: DNA
<213> ORGANISM: Cryptococcus neoformans

<400> SEQUENCE: 2
caggaaacag ctatgac                                                      17

<210> SEQ ID NO 3
<211> LENGTH: 32
<212> TYPE: DNA
<213> ORGANISM: Cryptococcus neoformans

<400> SEQUENCE: 3
catgggatcc acatgcccgt acgaccgtca ag                                     32

<210> SEQ ID NO 4
<211> LENGTH: 32
<212> TYPE: DNA
<213> ORGANISM: Cryptococcus neoformans

<400> SEQUENCE: 4
catgggatcc acatgcccgt acgaccgtca ag                                     32

<210> SEQ ID NO 5
<211> LENGTH: 30
<212> TYPE: DNA
<213> ORGANISM: Cryptococcus neoformans

<400> SEQUENCE: 5
cgacctgcag tcaacgtccg ttaccgaatc                                        30

```
<210> SEQ ID NO 6
<211> LENGTH: 24
<212> TYPE: DNA
<213> ORGANISM: Cryptococcus neoformans

<400> SEQUENCE: 6
gaaatgtcat cgcctgtgtg ccaa                                           24

<210> SEQ ID NO 7
<211> LENGTH: 24
<212> TYPE: DNA
<213> ORGANISM: Cryptococcus neoformans

<400> SEQUENCE: 7
tgtcaaactt gatcctgcgg agca                                           24

<210> SEQ ID NO 8
<211> LENGTH: 20
<212> TYPE: DNA
<213> ORGANISM: Cryptococcus neoformans

<400> SEQUENCE: 8
tgagaaggac cctgccaaca                                                20

<210> SEQ ID NO 9
<211> LENGTH: 21
<212> TYPE: DNA
<213> ORGANISM: Cryptococcus neoformans

<400> SEQUENCE: 9
actccggctt gtaggcatca a                                              21

<210> SEQ ID NO 10
<211> LENGTH: 30
<212> TYPE: DNA
<213> ORGANISM: Cryptococcus neoformans

<400> SEQUENCE: 10
ctagcatatg atggccgaga agaagcagac                                     30

<210> SEQ ID NO 11
<211> LENGTH: 31
<212> TYPE: DNA
<213> ORGANISM: Cryptococcus neoformans

<400> SEQUENCE: 11
ctaggaattc ttaacggtcc tcagcccact c                                   31

<210> SEQ ID NO 12
<211> LENGTH: 32
<212> TYPE: DNA
<213> ORGANISM: Cryptococcus neoformans

<400> SEQUENCE: 12
cctgggatcc atgtcgcaag actttagcgt ct                                  32

<210> SEQ ID NO 13
<211> LENGTH: 37
<212> TYPE: DNA
<213> ORGANISM: Cryptococcus neoformans

<400> SEQUENCE: 13
atggccatgg aggccatgtc gcaagacttt agcgtct                             37
```

<210> SEQ ID NO 14
<211> LENGTH: 39
<212> TYPE: DNA
<213> ORGANISM: Cryptococcus neoformans

<400> SEQUENCE: 14
catatggcca tggaggccat ggtgacttct aatgttgtc                     39

<210> SEQ ID NO 15
<211> LENGTH: 31
<212> TYPE: DNA
<213> ORGANISM: Cryptococcus neoformans

<400> SEQUENCE: 15
cgatggatcc ctaacggtct tcagcccatt c                             31

<210> SEQ ID NO 16
<211> LENGTH: 35
<212> TYPE: DNA
<213> ORGANISM: Cryptococcus neoformans

<400> SEQUENCE: 16
gagttgcgtg attgtgttct taatttcacc ccttt                         35

<210> SEQ ID NO 17
<211> LENGTH: 35
<212> TYPE: DNA
<213> ORGANISM: Cryptococcus neoformans

<400> SEQUENCE: 17
ggtgaaatta agaacacaat cacgcaactc gcctc                         35

<210> SEQ ID NO 18
<211> LENGTH: 24
<212> TYPE: DNA
<213> ORGANISM: Cryptococcus neoformans

<400> SEQUENCE: 18
atgcagcaat ggactggtgt caac                                     24

<210> SEQ ID NO 19
<211> LENGTH: 24
<212> TYPE: DNA
<213> ORGANISM: Cryptococcus neoformans

<400> SEQUENCE: 19
tgaactcgca gatgagcata ccga                                     24

<210> SEQ ID NO 20
<211> LENGTH: 21
<212> TYPE: DNA
<213> ORGANISM: Cryptococcus neoformans

<400> SEQUENCE: 20
gtactgagcg atgctgcagt g                                        21

<210> SEQ ID NO 21
<211> LENGTH: 36
<212> TYPE: DNA
<213> ORGANISM: Cryptococcus neoformans

<400> SEQUENCE: 21

-continued ctggccgtcg ttttactacg gcgagtgagt tcggac         36

<210> SEQ ID NO 22
<211> LENGTH: 37
<212> TYPE: DNA
<213> ORGANISM: Cryptococcus neoformans

<400> SEQUENCE: 22
gtcatagctg tttcctgcga ttcggtaacg gacgttg        37

<210> SEQ ID NO 23
<211> LENGTH: 20
<212> TYPE: DNA
<213> ORGANISM: Cryptococcus neoformans

<400> SEQUENCE: 23
actttcggcg acgacatcac                           20

<210> SEQ ID NO 24
<211> LENGTH: 20
<212> TYPE: DNA
<213> ORGANISM: Cryptococcus neoformans

<400> SEQUENCE: 24
gaccgtcaag aagcaactcg                           20

<210> SEQ ID NO 25
<211> LENGTH: 22
<212> TYPE: DNA
<213> ORGANISM: Cryptococcus neoformans

<400> SEQUENCE: 25
cagattgata gcttgcagct tc                        22

<210> SEQ ID NO 26
<211> LENGTH: 22
<212> TYPE: DNA
<213> ORGANISM: Cryptococcus neoformans

<400> SEQUENCE: 26
ggaatcaacg aagatctgaa gg                        22

<210> SEQ ID NO 27
<211> LENGTH: 30
<212> TYPE: DNA
<213> ORGANISM: Cryptococcus neoformans

<400> SEQUENCE: 27
cgatgggccc tcgtgcaggg cttccagcag                30

<210> SEQ ID NO 28
<211> LENGTH: 52
<212> TYPE: DNA
<213> ORGANISM: Cryptococcus neoformans

<400> SEQUENCE: 28
gatcctcgag tcacatcatc atcatcatca tacgtccgtt accgaatcgt tg    52

<210> SEQ ID NO 29
<211> LENGTH: 21
<212> TYPE: DNA
<213> ORGANISM: Cryptococcus neoformans

<400> SEQUENCE: 29
tgtggatgct ggcggaggat a                                        21

<210> SEQ ID NO 30
<211> LENGTH: 38
<212> TYPE: DNA
<213> ORGANISM: Cryptococcus neoformans

<400> SEQUENCE: 30
cataaataca ggatccatgc ccgtacgacc gtcaagaa                      38

<210> SEQ ID NO 31
<211> LENGTH: 59
<212> TYPE: DNA
<213> ORGANISM: Cryptococcus neoformans

<400> SEQUENCE: 31
acgcggccgc ttacttatcg tcgtcatcct tgtaatcacg tccgttaccg aatcgttgt   59

<210> SEQ ID NO 32
<211> LENGTH: 38
<212> TYPE: DNA
<213> ORGANISM: Cryptococcus neoformans

<400> SEQUENCE: 32
gcagcccggg ggatccatgt ctactgtgac ttctcccg                      38

<210> SEQ ID NO 33
<211> LENGTH: 44
<212> TYPE: DNA
<213> ORGANISM: Cryptococcus neoformans

<400> SEQUENCE: 33
acgtcgtatg ggtaggatcc ctcgtgatgc aattgcgcag ctac               44

<210> SEQ ID NO 34
<211> LENGTH: 43
<212> TYPE: DNA
<213> ORGANISM: Cryptococcus neoformans

<400> SEQUENCE: 34
gtggcggccg ctctagatta agcgtaatct ggtacgtcgt atg                43

<210> SEQ ID NO 35
<211> LENGTH: 38
<212> TYPE: DNA
<213> ORGANISM: Cryptococcus neoformans

<400> SEQUENCE: 35
gcagcccggg ggatccatgc ccgaaacgaa tacctccg                      38

<210> SEQ ID NO 36
<211> LENGTH: 39
<212> TYPE: DNA
<213> ORGANISM: Cryptococcus neoformans

<400> SEQUENCE: 36
tcgtatgggt aggatccact cctaacgtca aaactccac                     39

<210> SEQ ID NO 37
<211> LENGTH: 38
<212> TYPE: DNA
<213> ORGANISM: Cryptococcus neoformans

<400> SEQUENCE: 37
gcagcccggg ggatccatga actcacaatc tcccctg                                38

<210> SEQ ID NO 38
<211> LENGTH: 39
<212> TYPE: DNA
<213> ORGANISM: Cryptococcus neoformans

<400> SEQUENCE: 38
tcgtatgggt aggatccacg atgtacattc tcgtccatc                              39

<210> SEQ ID NO 39
<211> LENGTH: 38
<212> TYPE: DNA
<213> ORGANISM: Cryptococcus neoformans

<400> SEQUENCE: 39
caacatgtct ggatccatga actcacaatc tcccctg                                38

<210> SEQ ID NO 40
<211> LENGTH: 39
<212> TYPE: DNA
<213> ORGANISM: Cryptococcus neoformans

<400> SEQUENCE: 40
ttcttttacg cggccgctta agcgtaatct ggtacgtcg                              39

<210> SEQ ID NO 41
<211> LENGTH: 38
<212> TYPE: DNA
<213> ORGANISM: Cryptococcus neoformans

<400> SEQUENCE: 41
cgagctgtac ggatccatga actcacaatc tcccctg                                38

<210> SEQ ID NO 42
<211> LENGTH: 39
<212> TYPE: DNA
<213> ORGANISM: Cryptococcus neoformans

<400> SEQUENCE: 42
cgttactagt ggatccctta agcgtaatct ggtacgtcg                              39

<210> SEQ ID NO 43
<211> LENGTH: 59
<212> TYPE: DNA
<213> ORGANISM: Cryptococcus neoformans

<400> SEQUENCE: 43
acgcggccgc ttacttatcg tcgtcatcct tgtaatccac tgatagagag gtgaatagc        59

<210> SEQ ID NO 44
<211> LENGTH: 45
<212> TYPE: DNA
<213> ORGANISM: Cryptococcus neoformans

<400> SEQUENCE: 44
taatctggta cgtcgtatgg gtaacgatgt acattctcgt ccatc                       45

<210> SEQ ID NO 45
<211> LENGTH: 40
<212> TYPE: DNA
<213> ORGANISM: Cryptococcus neoformans

<400> SEQUENCE: 45
atccactagt tctagagtgg catgcggggc tcaggtatcg                         40

<210> SEQ ID NO 46
<211> LENGTH: 44
<212> TYPE: DNA
<213> ORGANISM: Cryptococcus neoformans

<400> SEQUENCE: 46
tggcggccgc tctagattaa gcgtaatctg gtacgtcgta tggg                    44

<210> SEQ ID NO 47
<211> LENGTH: 57
<212> TYPE: DNA
<213> ORGANISM: Cryptococcus neoformans

<400> SEQUENCE: 47
cggtacccgg ggatcctcaa tgatgatgat gatgatgacg tccgttaccg aatcgtt      57

<210> SEQ ID NO 48
<211> LENGTH: 928
<212> TYPE: PRT
<213> ORGANISM: Cryptococcus neoformans

<400> SEQUENCE: 48

Met Pro Val Arg Pro Ser Arg Ser Asn Ser Asp Ser Ile Arg His
1               5                   10                  15

Val Ala Asn Ser Ser Pro Ala Ser Ser Tyr Arg Pro Thr Ser Ile Arg
            20                  25                  30

Glu Arg Glu Thr Ser Pro Ile Asn Ala Phe Asn Gln Leu Ser Leu Asp
        35                  40                  45

Arg Ser Leu Thr Pro Pro Lys Ala Pro Arg Leu Ala Pro Gln Val Thr
    50                  55                  60

Arg Asp Pro Lys Tyr Thr Arg His Ile Arg Ser Gln Val Leu Arg Asn
65                  70                  75                  80

Thr Ser Arg Thr Pro Ser Ala Ala Ser Thr Asp Asp Glu Asp Asp Gln
                85                  90                  95

Asp Glu Arg Gly Arg Gly Gly Ile Asp Glu Glu Ala Lys Ser Trp Leu
            100                 105                 110

Glu Leu Arg Asp Gly Arg Gly Trp Lys Arg Asn Gly Lys Tyr Lys Gly
        115                 120                 125

Val Asn Lys Arg Gly Glu Ile Lys Asn Asp Leu Thr Asn Gln Leu Pro
    130                 135                 140

Pro Glu Ile Leu Ile Gln Ile Phe Arg Tyr Leu Pro Gly Asn Lys Asp
145                 150                 155                 160

Leu Leu Ser Val Leu Leu Val Ser Arg Phe Trp Cys Leu Cys Ala Phe
                165                 170                 175

Ser Leu Leu Trp Tyr Lys Pro Thr Leu Pro Thr Ile Thr Gln Leu Ala
            180                 185                 190

Ser Ile Ile Arg Val Ile His Ser Pro Thr Arg Ser Leu Pro Tyr Ala
        195                 200                 205

Asn Ala Ile Arg Arg Leu Pro Leu Ile Gln Leu Gly Pro Thr Leu Thr
    210                 215                 220

Asp Glu Leu Phe Thr Ser Leu Ser Val Cys Ser Arg Leu Glu Arg Leu
225                 230                 235                 240

Asn Ile Ser Gly Ala Asp Lys Leu Thr Ser Gly Ala Leu Arg Asn Val

-continued

```
                    245                 250                 255
Ile Ala Cys Val Pro Asn Leu Val Ser Leu Asp Leu Thr Gly Val Ile
                260                 265                 270

Asn Thr Asp Asp Ala Val Leu Val Val Gly Glu Thr Cys Lys Lys
            275                 280                 285

Leu Gln Ala Ile Asn Leu Ser Glu Cys Arg Leu Val Gly Asp Glu Gly
        290                 295                 300

Val Leu Ala Leu Ala Lys Glu Ser Arg Val Leu Arg Arg Ile Lys Phe
305                 310                 315                 320

Asp Lys Cys His Arg Ile Thr Gln Lys Ser Leu Ile Pro Leu Ile Arg
                325                 330                 335

Ala Cys Pro Leu Val Leu Glu Tyr Asp Leu Gln Asp Val Ile Ser Leu
            340                 345                 350

Ser Ser Ser Val Leu His Thr Val Phe Leu His Ala Ser His Leu Arg
        355                 360                 365

Glu Leu Arg Val Asn Gly Cys Val Ser Leu Asp Glu Asn Cys Ile Pro
    370                 375                 380

Asn Leu Leu Asp Leu Ser Glu Met Gln Asp Asp Trp Ile Ala Lys Val
385                 390                 395                 400

Ser Glu Asp Val Gly Ile Lys Val Glu Pro Ala Glu Gly Val Thr Met
                405                 410                 415

Leu Arg Pro Val Thr Thr Thr Phe Glu Tyr Leu Arg Val Val Asp Met
            420                 425                 430

Thr Gly Cys Thr Asp Leu Gly Asp Lys Ala Val Asp Asn Leu Ile Thr
        435                 440                 445

Asn Ala Pro Lys Leu Arg Gln Leu Thr Leu Asn Lys Cys Pro Ala Leu
    450                 455                 460

Thr Asp Lys Ser Leu Glu Ser Ile Gly Lys Gly Lys His Leu His
465                 470                 475                 480

Asn Leu His Leu Gly His Val Ser Leu Ile Thr Asp Asp Gly Val Ile
                485                 490                 495

Asn Leu Ala Lys Ser Cys Thr Arg Leu Arg Tyr Leu Asp Leu Ala Cys
            500                 505                 510

Cys Thr Leu Leu Thr Asp Ala Cys Val Ala Glu Ile Gly Glu Asn Met
        515                 520                 525

Pro Lys Leu Lys Arg Phe Gly Leu Val Lys Val Thr Asn Ile Thr Asp
    530                 535                 540

Glu Ala Ile Tyr Ser Leu Val Arg Lys His Thr Ser Leu Glu Arg Val
545                 550                 555                 560

His Leu Ser Tyr Cys Asp Gln Leu Ser Val Lys Ala Ile Ala Tyr Leu
                565                 570                 575

Leu Asn Lys Leu Ala His Ile Lys His Leu Ser Leu Thr Gly Val Ser
            580                 585                 590

Ser Phe Lys Val Pro Glu Leu Gln Glu Phe Cys Arg Pro Pro Asp
        595                 600                 605

Phe Phe Asn Asp His Gln Arg Ala Ala Phe Cys Val Phe Ser Gly Ser
    610                 615                 620

Arg Val Val Glu Leu Arg Asp Tyr Leu Asn Asn His Tyr Leu Pro Ser
625                 630                 635                 640

Met Glu Ile Asp Thr Ser Glu Asp Ser Gly His Asp Gly Ala Ala Ser
                645                 650                 655

Ser Thr Ser Ser Leu Thr Ile Pro Arg Ala Ala Pro Thr Pro Asp His
            660                 665                 670
```

```
Ser Ser Ile Ser Asn Ser Ile Leu Gln His Asn Asn Leu Val Tyr Arg
        675                 680                 685

Gln Ser Leu Ser Asn Leu Asn Asp Ala Trp Glu Asp Ala Ala Pro Pro
    690                 695                 700

Ile Ser Pro Thr Pro Met Ser Arg Pro Gln Pro Pro His Leu Phe Thr
705                 710                 715                 720

Thr Ser Ile Gln Tyr Gln Ser Ala Gln Pro Gly Glu Asn Ala Pro Phe
            725                 730                 735

Pro Ile Ala Ser Thr Ser Thr Ser Pro Pro Ala Phe Met Ser Ser Ser
            740                 745                 750

Ser Ala Arg Pro Thr Ser Asn Leu Thr Ser Ala Thr Pro Ser Tyr Phe
        755                 760                 765

Asn Ile Ser Leu Ser Pro Ser Leu His Asn Arg Phe Ala Tyr Gly Asp
        770                 775                 780

Thr Thr Leu Pro Pro His Leu Asp Tyr Leu Val Pro Pro Ser Gln Glu
785                 790                 795                 800

Ser Ser Arg Ser Ser Ser Ile Ser Ser Asn Gly Asp Arg Leu Pro Phe
                805                 810                 815

Ile Pro His Gln Gly Val Ser Asp Arg Ser Arg Gly Pro Asp Ala Gln
                820                 825                 830

Gly Arg Arg Asp Arg Pro Ser Gly Pro Arg Val Pro Ser Gly Ser Tyr
        835                 840                 845

Asn Val Ser Pro Ser Tyr Ala Asn Glu Phe Thr Thr Tyr Trp Pro Arg
    850                 855                 860

Glu Gly Arg Leu Pro Arg Ala Ser Asp Ser Gly Ile Gly Ile Thr Arg
865                 870                 875                 880

Ala His Ser Ala Glu Glu His Met Thr Gln Val Ala Asn Leu Ser Gln
            885                 890                 895

Arg Ser Ser Ala Asn Gly Ser Leu Ser Ser Ser Ala Gly Ala Gln Arg
            900                 905                 910

Glu Gly Gly Arg Gly Pro Arg Trp Leu Gln Arg Phe Gly Asn Gly Arg
        915                 920                 925

<210> SEQ ID NO 49
<211> LENGTH: 49
<212> TYPE: PRT
<213> ORGANISM: Cryptococcus neoformans
<220> FEATURE:
<221> NAME/KEY: DOMAIN
<222> LOCATION: (1)..(49)
<223> OTHER INFORMATION: F-Box domain

<400> SEQUENCE: 49

Leu Pro Pro Glu Ile Leu Ile Gln Ile Phe Arg Tyr Leu Pro Gly Asn
1               5                   10                  15

Lys Asp Leu Leu Ser Val Leu Leu Val Ser Arg Phe Trp Cys Leu Cys
            20                  25                  30

Ala Phe Ser Leu Leu Trp Tyr Lys Pro Thr Leu Pro Thr Ile Thr Gln
        35                  40                  45

Leu
```